(12) United States Patent
Manoharan et al.

(10) Patent No.: US 10,913,767 B2
(45) Date of Patent: Feb. 9, 2021

(54) OLIGONUCLEOTIDES COMPRISING ACYCLIC AND ABASIC NUCLEOSIDES AND ANALOGS

(75) Inventors: Muthiah Manoharan, Cambridge, MA (US); Kallanthottathil G. Rajeev, Cambridge, MA (US); Jeremy Lackey, Cambridge, MA (US); Narayanannair K. Jayaprakash, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 738 days.

(21) Appl. No.: 13/642,772

(22) PCT Filed: Apr. 22, 2011

(86) PCT No.: PCT/US2011/033598
§ 371 (c)(1),
(2), (4) Date: Feb. 1, 2013

(87) PCT Pub. No.: WO2011/133876
PCT Pub. Date: Oct. 27, 2011

(65) Prior Publication Data
US 2013/0130378 A1     May 23, 2013

Related U.S. Application Data

(60) Provisional application No. 61/326,969, filed on Apr. 22, 2010.

(51) Int. Cl.
| | |
|---|---|
| C07H 21/02 | (2006.01) |
| C07H 21/00 | (2006.01) |
| C07F 9/6512 | (2006.01) |
| C07F 9/655 | (2006.01) |
| C07F 9/6558 | (2006.01) |
| C07H 19/20 | (2006.01) |
| C12N 15/11 | (2006.01) |

(52) U.S. Cl.
CPC .......... *C07H 21/02* (2013.01); *C07F 9/6512* (2013.01); *C07F 9/6552* (2013.01); *C07F 9/65583* (2013.01); *C07H 19/20* (2013.01); *C07H 21/00* (2013.01); *C12N 15/111* (2013.01); *C12N 2310/14* (2013.01); *C12N 2310/32* (2013.01); *C12N 2310/332* (2013.01)

(58) Field of Classification Search
CPC ........ C07H 21/00; C07H 21/02; C07H 19/20; C12N 15/111; C12N 2310/14; C12N 2310/32; C12N 2310/332; C07F 9/6512; C07F 9/6552; C07F 9/65583
See application file for complete search history.

(56) References Cited

U.S. PATENT DOCUMENTS

| 4,794,183 A * | 12/1988 | Nakamura | C07F 9/65515 540/542 |
|---|---|---|---|
| 4,891,363 A * | 1/1990 | Nakamura | C07D 307/20 514/101 |
| 5,367,066 A | 11/1994 | Urdea et al. | |
| 5,998,203 A * | 12/1999 | Matulic-Adamic | C07H 19/06 435/325 |
| 2002/0141952 A1 | 10/2002 | Brown et al. | |
| 2003/0013668 A1* | 1/2003 | Veerapanane | C12N 15/1136 514/44 A |
| 2005/0119214 A1* | 6/2005 | Manoharan | C12N 15/111 514/44 A |
| 2005/0130924 A1* | 6/2005 | Monia | C12N 15/113 514/44 A |

(Continued)

FOREIGN PATENT DOCUMENTS

| WO | 1992002528 A1 | 2/1992 |
|---|---|---|
| WO | 1992021655 A2 | 12/1992 |

(Continued)

OTHER PUBLICATIONS

Herdewijn, P., "Nucleic Acids with a Six-Membered 'Carbohydrate' Mimic in the Backbone," Chemistry & Biodiversity, 7, 1-59 (2010).*

(Continued)

*Primary Examiner* — Richard A Schnizer
(74) *Attorney, Agent, or Firm* — Jeffrey N. Townes; Cozen O'Connor

(57) ABSTRACT

This invention relates to an oligonucleotide comprising one or more abasic nucleoside monomers of formula V:

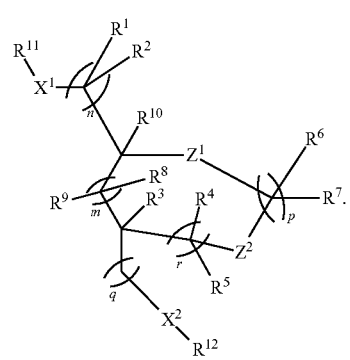

These monomers are useful for modifying of oligonucleotides at one or more positions. This invention also relates to a method of inhibiting the expression of a target gene in a cell. The method comprises contacting the cell with an oligonucleotide having one or more of the above formula (V).

25 Claims, 2 Drawing Sheets
Specification includes a Sequence Listing.

(56) References Cited

U.S. PATENT DOCUMENTS

| | | | | |
|---|---|---|---|---|
| 2007/0203084 | A1* | 8/2007 | Weiler | C12N 15/111 514/44 A |
| 2009/0239934 | A1* | 9/2009 | Schmitt-Milas | C12N 15/113 514/44 A |
| 2011/0207799 | A1* | 8/2011 | Rozema | A61P 31/12 514/44 A |

FOREIGN PATENT DOCUMENTS

| | | |
|---|---|---|
| WO | 1994022864 A1 | 10/1994 |
| WO | 1996040710 A1 | 12/1996 |
| WO | 2001085751 A1 | 11/2001 |
| WO | 2003037909 A1 | 5/2003 |
| WO | 20080138658 A2 | 11/2008 |
| WO | 2008147824 A2 | 12/2008 |
| WO | 2009061941 A2 | 5/2009 |

OTHER PUBLICATIONS

Adinolfi et al (Org. Biomol. Chem. 2:1879-1886, 2004) (Year: 2004).*
Adinolfi et al., (Synlett 2001 6: 745-748) (Year: 2001).*
D'Onofrio et al.,. (Bioconjugate Chem. 2008, 19, 607-616) (Year: 2008).*
Angle et al., "Stereoselective Synthesis of 3-Hydroxyproline Benzyl Esters from N-Protected beta-Aminoaldehydes and Benzyl Diazoacetate," J. Org. Chem. 69(13):4361-4368 (2004).
Ihara et al., "Asymmetric Syntheses of Chiral Propane-1,3-diols Starting from Malonic Acid," J. Chem. Soc. Perkin Trans. 1 5:897-903 (1989).
Cai et al., "The New Convenient Synthesis of Fluorinated Penciclovir Analogues 9-(4-Fluro-3-Hydroxymethylbutyl) Guanine (FHBG) and 2-amino-6-fluoro-9-(4-Hydroxy-3-Hydroxymethylbutyl) purine (6-Fluoropenciclovir)," J. Fluorine.Chem. 127(7):837-841(2006).
Harabe et al., "Conformational Analysis and Selective Hydrolysis of 2,5-disubstituted-1,3-Dioxane-2-Carboxylic Acid Esters," Tetrahedron Lett. 48(8):1443-1446 (2007).
Hirota et al., "Novel Synthesis of Purine Acyclonucleosides Possessing a Chiral 9-Hydroxyalkyl Group by Sugar Modication of 9-D-Ribitylpurines," J. Chem. Soc. Perkin Trans. 1 5:941-946 (1998).
Kim et al., "Acyclic Analogues of Deoxyadenosine 3',5'-Bisphophates as P2Y1 Receptor Antagonists," J. Med. Chem. 43(4):746-755 (2000).
Gin et al., "Helical Twist Sense Bias in Oligo(phenylene ethynylene)s Induced by an Optically Active Flexible Tether," Organic Letters 2(2):135-138 (2000).
Charette et al., "Enantioselective Synthesis of alpha, alpha-Disubstituted-alpha-Amino Acids by a Sequential Nucleophilic Addition to Nitriles," Tetrahedron 54(35):10525-10535 (1998).
Landais et al., "Oxidative Clevage of C—Si Bonds in Polyhydroxylated Silacyclopentanes," Tetrahedron Lett. 46(4):675-679 (2005).
Branalt et al., "Synthesis of [4, 5-Bis(hydroxymethyl)-1,3-oxathiolan-2-yl]nucleosides as Potential Inhibitors of HIV via Stereospecific Base-Induced Rearrangement of a 2,3-Epoxy Thioacetate," J. Org. Chem 61(11):3604-3610 (1996).
Marcia de Figueiredo et al., "N,N'-Carbonyldiimidazole-Mediated Cyclization of Amino Alcohols to Substituted Azetidines and Other N-Heterocycles," J. Org. Chem. 71(11):4147-4154 (2006).
Sasaki et al., "Synthesis of Hexopyranosyl Acetates and 2,3-Disubstituted Tetrahydropyrans via Chemoselective Hydrogenation of Hex-2-Enopyranosyl Acetates," Tetrahedron Lett. 47(47):8271-8274 (2006).
McLay et al., "The Discovery of RPR 200765A, a p38 MAP Kinase Inhibitor Displaying a Good Oral Anti-Arthritic Efficacy," Bioorg. Med. Chem. 9:537-554 (2001).
Koszytkowska-Stawinski et al., "Synthesis and Antiviral Properties of Aza-Analogues of Ganciclovir Derived from 5,5-Bis(hydroxymethyl)-Pyrrolidin-2-One," Tetrahedron 63(43):10587-10595 (2007).
Su et al., "Novel Non-Nucleosidic Phosphoramidites for Oligonucleotide Modification and Labeling," Bioorg. Med. Chem. Lett. 7(13):1639-1644 (1997).
Huang et al., "Synthesis and Analysis of Oligonucleotides Containing Abasic Site Analogues," J. Org. Chem. 73(7):2695-2703 (2008).
Wilson et al., "Oligodeoxyfluorosides: Strong Sequence Dependence of Fluorescence Emission," Tetrahedron 63 (17):3427-3433 (2007).
Ihara et al., "Photochemical Ligation of DNA Conjugates through Anthracene Cyclodimer Formation and Its Fidelity to the Template Sequences," J. Am. Chem. Soc. 126(29):8880-8881 (2004).
Peoc'h et al., "Efficient Chemical Synthesis of Oligodeoxynucleotides Containing a True Abasic Site," Tetrahedron Lett. 32(2):207-210 (1991).
Bertrand et al., "Synthesis, Thermal Stability and Reactivity Towards 9-Aminoellipticine of Double-Stranded Oligonucleotides Containing a True Abasic Site," Nucleic Acids Res. 17(24):10307-10319 (1989).
Vassuer et al., "Derivatization of Oligonucleotides Through Abasic Site Formation," Nucleosides & Nucleotides 10(1-3):107-117 (1991).
Hakala et al., "Oligonucleotide Conjugates Based on Acyclonucleosides and Their Use in DNA Hybridization Assays," Tetrahedron 58(43):8771-8777 (2002).
Benhida et al., "Incorporation of Serinol Derived Acyclic Nucleoside Analogues into Oligonucleotides: Influence on Duplex and Triplex Formation," Tetrahedron Lett. 39(34):6167-6170 (1998).
Vandendriessche et al., "Acyclic Oligonucleotides: Possibilities and Limitations," Tetrahedron 49(33):7223-7238 (1993).
Loakes et al., "Enzymatic Recognition of Acyclic Universal Base Analogues in Oligonucleotides," Nucleosides & Nucleotides 15(11-12):1891-1904 (1996).
Dreioe et al., "Synthesis and Evaluation of Oligodeoxynucleotides Containing 3'-O-Ethyl-4'-C-(Hydroxymethyl) Thymidine: Introduction of a Novel Class of Phosphodiester Internucleoside Linkages," Nucleosides & Nucleotides 13(9):1939-1952 (1994).
Rana et al., "Oligonucleotides with (N-Thymin-1-Ylacetyl) 1-Phenylserinol in Backbone: Chiral Acyclic Analogues that Form DNA Triplexes," Bioorg. Med. Chem. Lett. 7(22):2837-2842 (1997).
Kojima et al., "Generation of an Abasic Site in an Oligonucleotide by Using Acid-Labile 1-Deaza-2'-deoxyguanosine and Its Application to Postsynthetic Modification," Org. Lett. 7(4):709-712 (2005).
Obika et al., "Properties of Novel Oligonucleotide Analogues Containing an Acyclic Nucleoside and a Carbamate Linkage," Bioorg. Med. Chem. Lett. 6(12):1357-1360 (1996).
Fukui et al., "Oligonucleotides Covalently Linked to an Acridine at Artificial Abasic Site: Influence of Linker Length and the Base-Sequence," Tetrahedron Lett. 37(28):4983-4986 (1996).
Zhang et al., "Synthesis of Glycol Nucleic Acids," Synthesis 4:645-653 (2006).
Schlegel et al., "Improved Phosphoramidite Building Blocks for the Synthesis of the Simplified Nucleic Acid GNA," J. Org. Chem. 74(12): 4615-4618 (2009).

* cited by examiner

```
                              SEQUENCE LISTING

<160> NUMBER OF SEQ ID NOS: 58

<210> SEQ ID NO 1
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gccagguaag uau                                                          13

<210> SEQ ID NO 2
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ccagguaagu au                                                           12

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
tugucucugg uccuuacuua a                                                 21

<210> SEQ ID NO 4
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
cagguaagua u                                                            11

<210> SEQ ID NO 5
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5 cagguaagu                                                                9

<210> SEQ ID NO 6
<211> LENGTH: 8
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 6 cagguaag                                                                    8

<210> SEQ ID NO 7
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7 cagguaa                                                                     7

<210> SEQ ID NO 8
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
cagguaagua                                                                 10

<210> SEQ ID NO 9
<211> LENGTH: 29
<212> TYPE: PRT
<213> ORGANISM: Unknown
<220> FEATURE:
<223> OTHER INFORMATION: Description of Unknown: GALA
      peptide

<400> SEQUENCE: 9

Ala Ala Leu Glu Ala Leu Ala Glu Ala Leu Glu Ala Leu Glu Ala
1               5                   10                  15

Leu Glu Ala Leu Ala Glu Ala Ala Ala Gly Gly Cys
            20                  25

<210> SEQ ID NO 10
<211> LENGTH: 30
<212> TYPE: PRT
<213> ORGANISM: Unknown
<220> FEATURE:
<223> OTHER INFORMATION: Description of Unknown: EALA
      polypeptide

<400> SEQUENCE: 10

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Ala Gly Gly Cys
            20                  25                  30

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

```
Ala Leu Glu Ala Leu Ala Glu Ala Leu Glu Ala Leu Ala Glu Ala
1               5                   10                  15
```

<210> SEQ ID NO 12
<211> LENGTH: 22
<212> TYPE: PRT
<213> ORGANISM: Unknown
<220> FEATURE:
<223> OTHER INFORMATION: Description of Unknown: INF-7
      peptide

<400> SEQUENCE: 12

```
Gly Leu Phe Glu Ala Ile Glu Gly Phe Ile Glu Asn Gly Trp Glu Gly
1               5                   10                  15

Met Ile Trp Asp Tyr Gly
            20
```

<210> SEQ ID NO 13
<211> LENGTH: 23
<212> TYPE: PRT
<213> ORGANISM: Unknown
<220> FEATURE:
<223> OTHER INFORMATION: Description of Unknown: InfHA-2
      peptide

<400> SEQUENCE: 13

```
Gly Leu Phe Gly Ala Ile Ala Gly Phe Ile Glu Asn Gly Trp Glu Gly
1               5                   10                  15

Met Ile Asp Gly Trp Tyr Gly
            20
```

<210> SEQ ID NO 14
<211> LENGTH: 48
<212> TYPE: PRT
<213> ORGANISM: Unknown
<220> FEATURE:
<223> OTHER INFORMATION: Description of Unknown: diINF-7
      polypeptide

<400> SEQUENCE: 14

```
Gly Leu Phe Glu Ala Ile Glu Gly Phe Ile Glu Asn Gly Trp Glu Gly
1               5                   10                  15

Met Ile Asp Gly Trp Tyr Gly Cys Gly Leu Phe Glu Ala Ile Glu Gly
            20                  25                  30

Phe Ile Glu Asn Gly Trp Glu Gly Met Ile Asp Gly Trp Tyr Gly Cys
        35                  40                  45
```

<210> SEQ ID NO 15
<211> LENGTH: 44
<212> TYPE: PRT
<213> ORGANISM: Unknown
<220> FEATURE:
<223> OTHER INFORMATION: Description of Unknown: diINF-3
      polypeptide

<400> SEQUENCE: 15

```
Gly Leu Phe Glu Ala Ile Glu Gly Phe Ile Glu Asn Gly Trp Glu Gly
1               5                   10                  15

Met Ile Asp Gly Gly Cys Gly Leu Phe Glu Ala Ile Glu Gly Phe Ile
            20                  25                  30

Glu Asn Gly Trp Glu Gly Met Ile Asp Gly Gly Cys
        35                  40
```

```
<210> SEQ ID NO 16
<211> LENGTH: 35
<212> TYPE: PRT
<213> ORGANISM: Unknown
<220> FEATURE:
<223> OTHER INFORMATION: Description of Unknown: GLF
      polypeptide

<400> SEQUENCE: 16

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
            20                  25                  30

Gly Ser Cys
        35

<210> SEQ ID NO 17
<211> LENGTH: 34
<212> TYPE: PRT
<213> ORGANISM: Unknown
<220> FEATURE:
<223> OTHER INFORMATION: Description of Unknown: GALA-INF3
      polypeptide

<400> SEQUENCE: 17

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
            20                  25                  30

Ser Cys

<210> SEQ ID NO 18
<211> LENGTH: 41
<212> TYPE: PRT
<213> ORGANISM: Unknown
<220> FEATURE:
<223> OTHER INFORMATION: Description of Unknown: INF-5
      polypeptide
<220> FEATURE:
<221> NAME/KEY: MOD_RES
<222> LOCATION: (17)..(17)
<223> OTHER INFORMATION: NorLeu
<220> FEATURE:
<221> NAME/KEY: MOD_RES
<222> LOCATION: (38)..(38)
<223> OTHER INFORMATION: NorLeu

<400> SEQUENCE: 18

Gly Leu Phe Glu Ala Ile Glu Gly Phe Ile Glu Asn Gly Trp Glu Gly
1               5                   10                  15

Leu Ile Asp Gly Lys Gly Leu Phe Glu Ala Ile Glu Gly Phe Ile Glu
            20                  25                  30

Asn Gly Trp Glu Gly Leu Ile Asp Gly
            35                  40

<210> SEQ ID NO 19
<211> LENGTH: 19
<212> TYPE: PRT
<213> ORGANISM: Unknown
<220> FEATURE:
<223> OTHER INFORMATION: Description of Unknown: JTS-1
      peptide

<400> SEQUENCE: 19

Leu Phe Glu Ala Leu Leu Glu Leu Leu Glu Ser Leu Trp Glu Leu Leu
1               5                   10                  15
```

Leu Glu Ala

<210> SEQ ID NO 20
<211> LENGTH: 20
<212> TYPE: PRT
<213> ORGANISM: Unknown
<220> FEATURE:
<223> OTHER INFORMATION: Description of Unknown: ppTG1
      peptide

<400> SEQUENCE: 20

Gly Leu Phe Lys Ala Leu Leu Lys Leu Leu Lys Ser Leu Trp Lys Leu
1               5                   10                  15

Leu Leu Lys Ala
            20

<210> SEQ ID NO 21
<211> LENGTH: 20
<212> TYPE: PRT
<213> ORGANISM: Unknown
<220> FEATURE:
<223> OTHER INFORMATION: Description of Unknown: ppTG20
      peptide

<400> SEQUENCE: 21

Gly Leu Phe Arg Ala Leu Leu Arg Leu Leu Arg Ser Leu Trp Arg Leu
1               5                   10                  15

Leu Leu Arg Ala
            20

<210> SEQ ID NO 22
<211> LENGTH: 30
<212> TYPE: PRT
<213> ORGANISM: Unknown
<220> FEATURE:
<223> OTHER INFORMATION: Description of Unknown: KALA
      polypeptide

<400> SEQUENCE: 22

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 23
<211> LENGTH: 22
<212> TYPE: PRT
<213> ORGANISM: Unknown
<220> FEATURE:
<223> OTHER INFORMATION: Description of Unknown: HA
      peptide

<400> SEQUENCE: 23

Gly Leu Phe Phe Glu Ala Ile Ala Glu Phe Ile Glu Gly Gly Trp Glu
1               5                   10                  15

Gly Leu Ile Glu Gly Cys
            20

<210> SEQ ID NO 24
<211> LENGTH: 26
<212> TYPE: PRT
<213> ORGANISM: Unknown
<220> FEATURE:
<223> OTHER INFORMATION: Description of Unknown: Melittin
      peptide

```
<400> SEQUENCE: 24

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

His His His His His Trp Tyr Gly
1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys His Lys Lys Lys Lys Lys Lys His Cys
1               5                   10

<210> SEQ ID NO 27
<211> LENGTH: 16
<212> TYPE: PRT
<213> ORGANISM: Unknown
<220> FEATURE:
<223> OTHER INFORMATION: Description of Unknown: penetratin
      peptide

<400> SEQUENCE: 27

Arg Gln Ile Lys Ile Trp Phe Gln Asn Arg Arg Met Lys Trp Lys Lys
1               5                   10                  15

<210> SEQ ID NO 28
<211> LENGTH: 14
<212> TYPE: PRT
<213> ORGANISM: Human immunodeficiency virus

<400> SEQUENCE: 28

Gly Arg Lys Lys Arg Arg Gln Arg Arg Arg Pro Pro Gln Cys
1               5                   10

<210> SEQ ID NO 29
<211> LENGTH: 27
<212> TYPE: PRT
<213> ORGANISM: Unknown
<220> FEATURE:
<223> OTHER INFORMATION: Description of Unknown: signal sequence based
      peptide

<400> SEQUENCE: 29

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25
```

```
<210> SEQ ID NO 30
<211> LENGTH: 18
<212> TYPE: PRT
<213> ORGANISM: Unknown
<220> FEATURE:
<223> OTHER INFORMATION: Description of Unknown: PVEC
      peptide

<400> SEQUENCE: 30

Leu Leu Ile Ile Leu Arg Arg Arg Ile Arg Lys Gln Ala His Ala His
1               5                   10                  15

Ser Lys

<210> SEQ ID NO 31
<211> LENGTH: 26
<212> TYPE: PRT
<213> ORGANISM: Unknown
<220> FEATURE:
<223> OTHER INFORMATION: Description of Unknown: transportan
      peptide

<400> SEQUENCE: 31

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 32
<211> LENGTH: 18
<212> TYPE: PRT
<213> ORGANISM: Unknown
<220> FEATURE:
<223> OTHER INFORMATION: Description of Unknown: amphiphilic model
      peptide

<400> SEQUENCE: 32

Lys Leu Ala Leu Lys Leu Ala Leu Lys Ala Leu Lys Ala Ala Leu Lys
1               5                   10                  15

Leu Ala

<210> SEQ ID NO 33
<211> LENGTH: 9
<212> TYPE: PRT
<213> ORGANISM: Unknown
<220> FEATURE:
<223> OTHER INFORMATION: Description of Unknown: "Arg9" motif
      peptide

<400> SEQUENCE: 33

Arg Arg Arg Arg Arg Arg Arg Arg Arg
1               5

<210> SEQ ID NO 34
<211> LENGTH: 10
<212> TYPE: PRT
<213> ORGANISM: Unknown
<220> FEATURE:
<223> OTHER INFORMATION: Description of Unknown: Bacterial cell wall
      permeating peptide

<400> SEQUENCE: 34

Lys Phe Phe Lys Phe Phe Lys Phe Phe Lys
1               5                   10

<210> SEQ ID NO 35
```

```
<211> LENGTH: 37
<212> TYPE: PRT
<213> ORGANISM: Unknown
<220> FEATURE:
<223> OTHER INFORMATION: Description of Unknown: LL-37
      polypeptide

<400> SEQUENCE: 35

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 36
<211> LENGTH: 31
<212> TYPE: PRT
<213> ORGANISM: Unknown
<220> FEATURE:
<223> OTHER INFORMATION: Description of Unknown: cecropin P1
      polypeptide

<400> SEQUENCE: 36

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 37
<211> LENGTH: 30
<212> TYPE: PRT
<213> ORGANISM: Unknown
<220> FEATURE:
<223> OTHER INFORMATION: Description of Unknown: alpha-defensin
      polypeptide

<400> SEQUENCE: 37

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 38
<211> LENGTH: 36
<212> TYPE: PRT
<213> ORGANISM: Unknown
<220> FEATURE:
<223> OTHER INFORMATION: Description of Unknown: beta-defensin
      polypeptide

<400> SEQUENCE: 38

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35

<210> SEQ ID NO 39
<211> LENGTH: 42
<212> TYPE: PRT
<213> ORGANISM: Unknown
<220> FEATURE:
<223> OTHER INFORMATION: Description of Unknown: PR-39
``` polypeptide

<400> SEQUENCE: 39

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40

<210> SEQ ID NO 40
<211> LENGTH: 13
<212> TYPE: PRT
<213> ORGANISM: Unknown
<220> FEATURE:
<223> OTHER INFORMATION: Description of Unknown: indolicidin
      peptide

<400> SEQUENCE: 40

Ile Leu Pro Trp Lys Trp Pro Trp Trp Pro Trp Arg Arg
1               5                   10

<210> SEQ ID NO 41
<211> LENGTH: 16
<212> TYPE: PRT
<213> ORGANISM: Unknown
<220> FEATURE:
<223> OTHER INFORMATION: Description of Unknown: RFGF
      peptide

<400> SEQUENCE: 41

Ala Ala Val Ala Leu Leu Pro Ala Val Leu Leu Ala Leu Leu Ala Pro
1               5                   10                  15

<210> SEQ ID NO 42
<211> LENGTH: 11
<212> TYPE: PRT
<213> ORGANISM: Unknown
<220> FEATURE:
<223> OTHER INFORMATION: Description of Unknown: RFGF analogue
      peptide

<400> SEQUENCE: 42

Ala Ala Leu Leu Pro Val Leu Leu Ala Ala Pro
1               5                   10

<210> SEQ ID NO 43
<211> LENGTH: 12
<212> TYPE: PRT
<213> ORGANISM: Unknown
<220> FEATURE:
<223> OTHER INFORMATION: Description of Unknown: bactenecin
      peptide

<400> SEQUENCE: 43

Arg Lys Cys Arg Ile Val Val Ile Arg Val Cys Arg
1               5                   10

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 44
tugucucugg uccuuacuua a                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
uugucucugg uccuuacuut t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
uugucucugg uccuuacuut t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
tugucucugg uccuuacuua a                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
tugucucugg uccuuacuua a                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
    Synthetic oligonucleotide

<400> SEQUENCE: 49
utgucucugg uccuuacuua a                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 50
uugtcucugg uccuuacuua a                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 51
uuguctcugg uccuuacuua a                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 52
uugucuctgg uccuuacuua a                                              21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (20)..(21)
<223> OTHER INFORMATION: abasic DNA
    (2-hydroxymethyl-tetrahydropyrane-3-phosphate (abasic pyrannose)

<400> SEQUENCE: 53
uugucucugg uccuuacuun n                                              21

<210> SEQ ID NO 54
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: abasic DNA
      (2-hydroxymethyl-tetrahydropyrane-3-phosphate (abasic pyrannose)

<400> SEQUENCE: 54
nugucucugg uccuuacuua a                                            21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: abasic DNA
      (2-hydroxymethyl-tetrahydropyrane-3-phosphate (abasic pyrannose)

<400> SEQUENCE: 55
ungucucugg uccuuacuua a                                            21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: abasic DNA
      (2-hydroxymethyl-tetrahydropyrane-3-phosphate (abasic pyrannose)

<400> SEQUENCE: 56
uugncucugg uccuuacuua a                                            21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: abasic DNA
      (2-hydroxymethyl-tetrahydropyrane-3-phosphate (abasic pyrannose)

<400> SEQUENCE: 57
uugucncugg uccuuacuua a                                            21
```

```
<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: abasic DNA
      (2-hydroxymethyl-tetrahydropyrane-3-phosphate (abasic pyrannose)

<400> SEQUENCE: 58
uugucucngg uccuuacuua a                                              21
```

OLIGONUCLEOTIDES COMPRISING ACYCLIC AND ABASIC NUCLEOSIDES AND ANALOGS

PRIORITY CLAIM

This application claims priority to PCT Application No. PCT/US2011/033598, filed Apr. 22, 2011, which claims benefit of priority to U.S. Provisional Application No. 61/326,969, filed Apr. 22, 2010, all of which are incorporated herein by reference in their entirety.

TECHNICAL FIELD

Provided herein acyclic and abasic nucleosides and oligonucleotides prepared therefrom.

BACKGROUND

Oligonucleotides and their analogs have been developed for various uses in molecular biology, including use as probes, primers, linkers, adapters, and gene fragments. In a number of these applications, the oligonucleotides specifically hybridize to a target nucleic acid.

In certain instances, chemical modifications have been introduced into oligonucleotides to increase their usefulness in diagnostics, as research reagents and as therapeutic entities. Such modifications include those designed for a variety of purposes, for example: to increase binding to a target nucleic acid (i.e., increase their melting temperature, $T_m$), to assist in identification of the oligonucleotide or an oligonucleotide-target complex, to increase cell penetration, to stabilize against nucleases and other enzymes that degrade or interfere with the structure or activity of the oligonucleotide, to provide a mode of disruption (a terminating event) once sequence-specifically bound to a target, and to improve the pharmacokinetic properties of the oligonucleotide.

SUMMARY

In one aspect, the invention provides acyclic and abasic nucleosides having the structure of formula (I), formula (II), formula (III) or isomers thereof. These monomers are useful for modifying of oligonucleotides at one or more positions.

In another aspect, the invention provides oligonucleotides comprising conformationally locked dinucleotide monomers having the structure of formula (IV)-formula (VI), or isomers thereof. The said oligonucleotides can be single-stranded RNAi agent (single-stranded siRNA), double-stranded RNAi agent (double-stranded siRNA), micro RNA, antimicroRNA, aptamer, ribozyme, decoy oligonucleotide, triplex forming oligonucleotide, U1 addaptor, or antisense oligonucleotides. In some embodiments, the invention provides single-stranded and double-stranded oligonucleotides that cleave a target RNA sequence by a RISC mediated pathway.

In yet another aspect, the invention provides methods of inhibiting the expression of a target gene in cell, the method comprising: contacting a cell with an oligonucleotide described herein.

DETAILED DESCRIPTION

Figure 1:
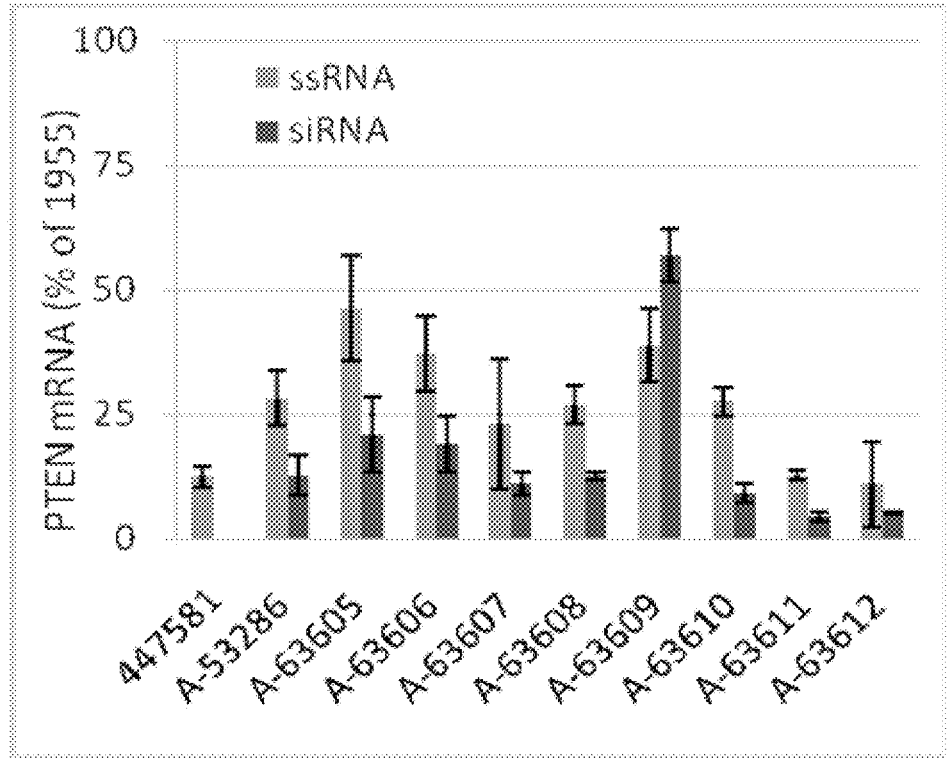
FIG. 1 shows the in vitro activity of N1, internal and 3'-end acyclic GNA modified ssRNA siRNA in a PTEN assay.
Figure 2:
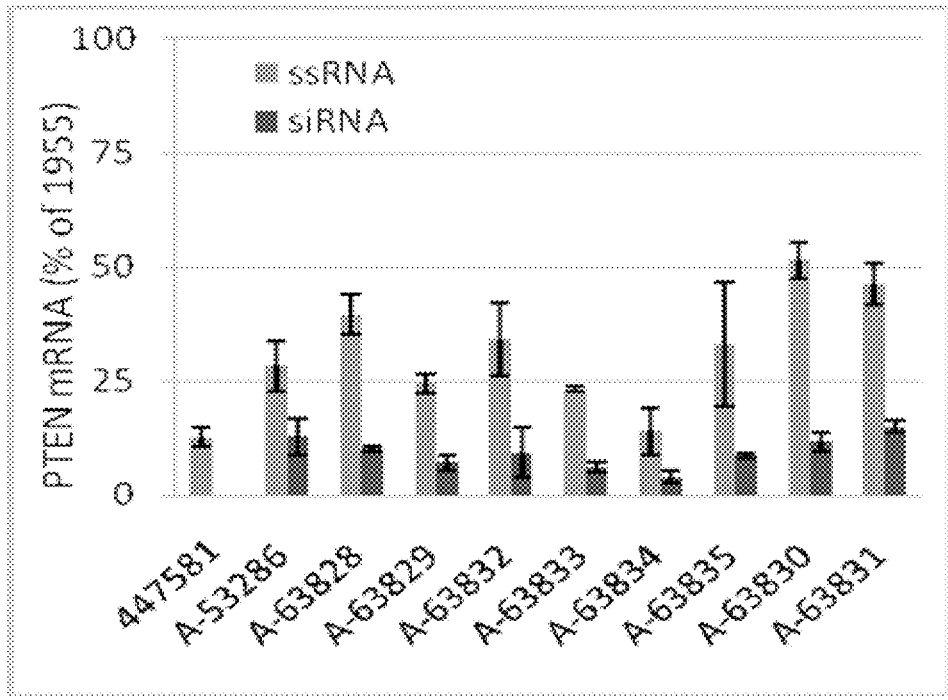
FIG. 2 shows the in vitro activity of N1, internal and 3'-end acyclic GNA modified ssRNA siRNA in a PTEN assay.

In one aspect, the invention provides acyclic and abasic nucleoside monomers having the structure of formula (I), formula (II), formula (III):

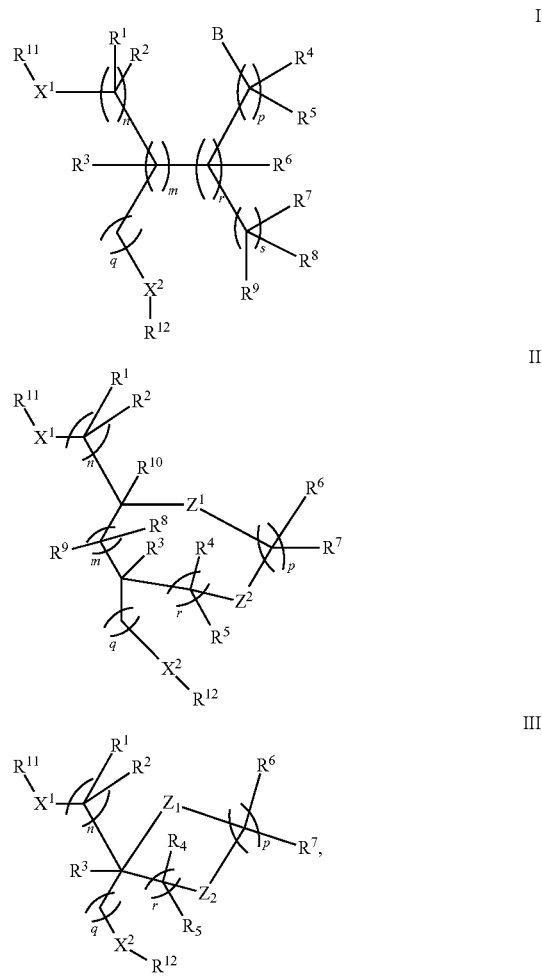

or isomers thereof, wherein: each B is independently H or a nucleobase; $X^1$ and $X^2$ are independently for each occurrence absent, O, S, or NR'; each of $R^1$, $R^2$, $R^3$, $R^4$, $R^5$, $R^6$, $R^7$, $R^8$, $R^9$ and $R^{10}$ is independently for each occurrence H, halo, $OR^{13}$, $N(R')(R'')$, alkyl, alkenyl, alkynyl, aryl, heteroaryl, cyclyl, heterocyclyl, ω-amino alkyl, ω-hydroxy alkyl, ω-hydroxy alkenyl, or ω-hydroxy alkynyl each of which can be optionally substituted; $R^{11}$ and $R^{12}$ are independently for each occurrence H, protecting group, a reactive phosphorus group, or solid support; $R^{13}$ is independently for each occurrence H, alkyl, alkenyl, alkynyl, cycloalkyl, heterocyclyl, aryl, heteroaryl, heteroaryl, aralkyl, ω-amino alkyl, ω-hydroxy alkyl, or ω-hydroxy alkenyl, each of which can be optionally substituted; $R^{13}$ is independently for each occurrence H, alkyl, alkenyl, alkynyl, cycloalkyl, heterocyclyl, aryl, heteroaryl, heteroaryl, aralkyl, ω-amino alkyl, ω-hydroxy alkyl, or ω-hydroxy alkenyl, each of which can be optionally substituted; $Z^1$ and $Z^2$ are each independently O, S, N(R'), $C(R^9)(R^{10})$, $C(R^9)(OR^{13})$, C(O), or C(S); each of R' and R" is independently for each occurrence H, alkyl, alkenyl, alkynyl, aryl, heteroaryl, cyclyl, heterocyclyl, ω-amino alkyl, ω-hydroxy alkyl, ω-hydroxy alkenyl, or ω-hydroxy alkynyl, each of which can be optionally substituted; and each of m, n, p, q, r, and s is independently for each occurrence 0-10.

When B is a nucleobase, any known nucleobase in the art can be employed. A detailed description of the nucleobases amenable to the invention is provided below in the oligonucleotide section. Thus, it is to be understood that each B is selected independently from the nucleobases disclosed herein.

The monomers provided herein are useful for modification of oligonucleotides at one or more positions. Accordingly, in some embodiments monomers having reactive phosphorus groups are provided that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, alkylphosphonate, phosphate triesters and phosphorus containing chiral auxiliaries. Generally, solid phase synthesis of oligonucleotides utilizes phosphoramidites ($P^{III}$ chemistry) as reactive phosphites. The intermediate phosphite compounds are subsequently oxidized to the Pv state using known methods to yield, in preferred embodiments, phosphodiester or phosphorothioate internucleotide linkages. In some embodiments, the reactive phosphorous group is a diisopropylcyanoethoxy phosphoramidite group.

In some embodiments, one of $R^{11}$ and $R^{12}$ is a protecting group and the other is a reactive phosphorus group or a solid support. In one preferred embodiment, $R^{11}$ is a protecting group and $R^{12}$ is a reactive phosphorus group or a solid support.

Representative protecting groups are disclosed in Greene and Wuts, *Protective Groups in Organic Synthesis*, Chapter 2, 2d ed., John Wiley & Sons, New York, 1991; *Oligonucleotides And Analogues A Practical Approach*, Ekstein, F. Ed., IRL Press, N.Y, 1991; and Beaucage et al. *Tetrahedron* 1992, 48, 2223-2311.

Exemplary hydroxyl protecting groups include, but are not limited to acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl, 9-phenylxanthine-9-yl (Pixyl) or 9-(p-methoxyphenyl)xanthine-9-yl (MOX). In a preferred embodiment, each of the hydroxyl protecting groups is, independently, acetyl, benzyl, t-butyldimethylsilyl, t-butyldiphenylsilyl or 4,4'-dimethoxytrityl. In some embodiments, the hydroxyl protecting group is selected from the group consisting of trityl, monomethoxytrityl and 4,4'-dimethoxytrityl group.

In some embodiments, $X^1$ and $X^2$ are each independently O or S.

In some embodiments, the monomer of formula (I) is:

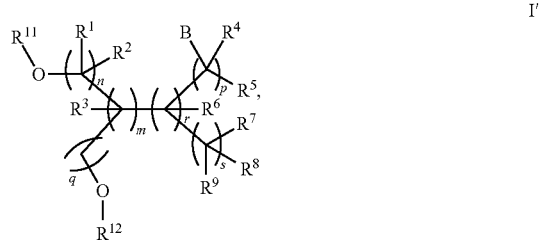

I' wherein: each B is independently H or a nucleobase; each of $R^1$, $R^2$, $R^3$, $R^4$, $R^5$, $R^6$, $R^7$, $R^8$, $R^9$ and $R^{10}$ is independently for each occurrence H, halo, $OR^{13}$, N(R')(R"), alkyl, alkenyl, alkynyl, aryl, heteroaryl, cyclyl, heterocyclyl, ω-amino alkyl, ω-hydroxy alkyl, ω-hydroxy alkenyl, or ω-hydroxy alkynyl each of which can be optionally substituted; $R^{11}$ and $R^{12}$ are independently for each occurrence H, protecting group, a reactive phosphorus group, or solid support; $R^{13}$ is independently for each occurrence H, alkyl, alkenyl, alkynyl, cycloalkyl, heterocyclyl, aryl, heteroaryl, heteroaryl, aralkyl, ω-amino alkyl, ω-hydroxy alkyl, or ω-hydroxy alkenyl, each of which can be optionally substituted; $R^{13}$ is independently for each occurrence H, alkyl, alkenyl, alkynyl, cycloalkyl, heterocyclyl, aryl, heteroaryl, heteroaryl, aralkyl, ω-amino alkyl, ω-hydroxy alkyl, or ω-hydroxy alkenyl, each of which can be optionally substituted; $Z^1$ and $Z^2$ are each independently O, S, N(R'), $C(R^9)(R^{10})$, $C(R^9)(OR^{13})$, C(O), or C(S); each of R' and R" is independently for each occurrence H, alkyl, alkenyl, alkynyl, aryl, heteroaryl, cyclyl, heterocyclyl, ω-amino alkyl, ω-hydroxy alkyl, ω-hydroxy alkenyl, or ω-hydroxy alkynyl, each of which can be optionally substituted; and each of m, n, p, q, r, and s is independently for each occurrence 0-10.

In some embodiments, the monomer of formula (II) is:

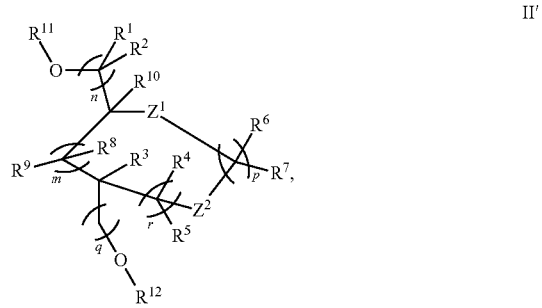

II' wherein: each B is independently H or a nucleobase; each of $R^1$, $R^2$, $R^3$, $R^4$, $R^5$, $R^6$, $R^7$, $R^8$, $R^9$ and $R^{10}$ is independently for each occurrence H, halo, $OR^{13}$, N(R')(R"), alkyl, alkenyl, alkynyl, aryl, heteroaryl, cyclyl, heterocyclyl, ω-amino alkyl, ω-hydroxy alkyl, ω-hydroxy alkenyl, or ω-hydroxy alkynyl each of which can be optionally substituted; $R^{11}$ and $R^{12}$ are independently for each occurrence H, protecting group, a reactive phosphorus group, or solid support; $R^{13}$ is independently for each occurrence H, alkyl, alkenyl, alkynyl, cycloalkyl, heterocyclyl, aryl, heteroaryl, heteroaryl, aralkyl, ω-amino alkyl, ω-hydroxy alkyl, or ω-hydroxy alkenyl, each of which can be optionally substituted; $R^{13}$ is independently for each occurrence H, alkyl, alkenyl, alkynyl, cycloalkyl, heterocyclyl, aryl, heteroaryl, heteroaryl, aralkyl, ω-amino alkyl, ω-hydroxy alkyl, or ω-hydroxy alkenyl, each of which can be optionally substituted; $Z^1$ and $Z^2$ are each independently O, S, N(R'), C(R$^9$)(R$^{10}$), C(R$^9$)(OR$^{13}$), C(O), or C(S); each of R' and R" is independently for each occurrence H, alkyl, alkenyl, alkynyl, aryl, heteroaryl, cyclyl, heterocyclyl, ω-amino alkyl, ω-hydroxy alkyl, ω-hydroxy alkenyl, or ω-hydroxy alkynyl, each of which can be optionally substituted; and each of m, n, p, q, r, and s is independently for each occurrence 0-10.

In some embodiments, the monomer of formula (III) is:

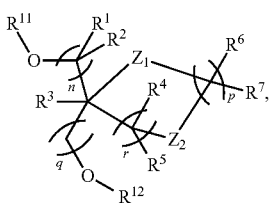

III' wherein: each B is independently H or a nucleobase; each of R$^1$, R$^2$, R$^3$, R$^4$, R$^5$, R$^6$, R$^7$, R$^8$, R$^9$ and R$^{10}$ is independently for each occurrence H, halo, OR$^{13}$, N(R')(R"), alkyl, alkenyl, alkynyl, aryl, heteroaryl, cyclyl, heterocyclyl, ω-amino alkyl, ω-hydroxy alkyl, ω-hydroxy alkenyl, or ω-hydroxy alkynyl each of which can be optionally substituted; R$^{11}$ and R$^{12}$ are independently for each occurrence H, protecting group, a reactive phosphorus group, or solid support; R$^{13}$ is independently for each occurrence H, alkyl, alkenyl, alkynyl, cycloalkyl, heterocyclyl, aryl, heteroaryl, heteroaryl, aralkyl, ω-amino alkyl, ω-hydroxy alkyl, or ω-hydroxy alkenyl, each of which can be optionally substituted; R$^{13}$ is independently for each occurrence H, alkyl, alkenyl, alkynyl, cycloalkyl, heterocyclyl, aryl, heteroaryl, heteroaryl, aralkyl, ω-amino alkyl, ω-hydroxy alkyl, or ω-hydroxy alkenyl, each of which can be optionally substituted; $Z^1$ and $Z^2$ are each independently O, S, N(R'), C(R$^9$)(R$^{10}$), C(R$^9$)(OR$^{13}$), C(O), or C(S); each of R' and R" is independently for each occurrence H, alkyl, alkenyl, alkynyl, aryl, heteroaryl, cyclyl, heterocyclyl, ω-amino alkyl, ω-hydroxy alkyl, ω-hydroxy alkenyl, or ω-hydroxy alkynyl, each of which can be optionally substituted; and each of m, n, p, q, r, and s is independently for each occurrence 0-10.

In another aspect the invention provides oligonucleotides comprising at least one (e.g., 1, 2, 3, 4, 5, 6, 7, 8, 9, 10, 11, 12, 13, 14, 15, 16, 17, 18, 19, 20 or more) monomer described in the above formulas. The monomers described herein can be placed at any position in an oligonucleotide. For example, the monomers described herein can be placed the last position on the 5'-end (5'-end terminal position), the last position on 3'-end (3'-end terminal position), at an internal position. Accordingly, the invention provides an oligonucleotide comprising at least one modified nucleoside of formula (I), (II), (III), (I'), (II'), or (III'), optionally in combination with natural base and derivatives thereof, or modified nucleobase. The modified base includes high affinity modification such as G-clamp and analogs, phenoxazines and analogs; bi- and tricyclic non-natural nucleoside bases. The invention further provides said modified oligonucleotides with 3', 5' or both 3' and 5' terminal phosphate or phosphate mimics. The phosphate or phosphate mimics includes α- and/or β-configuration with respect to the sugar ring or combinations thereof. The phosphate or phosphate mimics include but not limited to: natural phosphate, -phosphorothioate, phosphorodithioate, borano phosphate, borano thiophospahte, phosphonate, halogen substituted phosphoantes, phosphoramidates, phosphodiester, phosphotriester, thiophosphodiester, thiophosphotriester, diphosphates and triphosphates. The invention also provides sugar modified purine dimers at 3' and 5'-terminals (i.e. 5'/3'-GG, AA, AG, GA, GI, IA etc.), wherein the purine bases are natural or chemically modified preferably at 2, 6 and 7 positions of the base or combinations thereof. The invention also provides nucleoside at postion 1 (5'-end) with 2' and/or 4'-sugar modified natural and modified nucleobase, purine or pyrimidine nucleobase mimics or combinations thereof. The said modified oligonucleotides could be single stranded siRNA, double stranded siRNA, micro RNA, antimicroRNA, aptamer or antisense oligonucleotide containing a motif selected from the modifications described herein and combinations of modifications thereof. The invention provides that the said modified oligonucleotide is one of the strands or constitue for both strands of a double strands siRNA. In one occurence the modified oligonucleotide is the guide or antisense strand and in another occurence the modified oligonucleotide is sense or passenger strand of the double stranded siRNA or both the strands of ds siRNA bear modified oligoncleotides.

The oligonucleotides containing the monomers of any of the above formulas can also be used in a method of inhibiting the expression of a target gene in a cell. Such method comprises contacting the cell with the oligonucleotide comprising the monomers of any of the above formulas.

In some embodiments the oligonucleotide comprises at least one monomer of formula (IV), (V) or (VI):

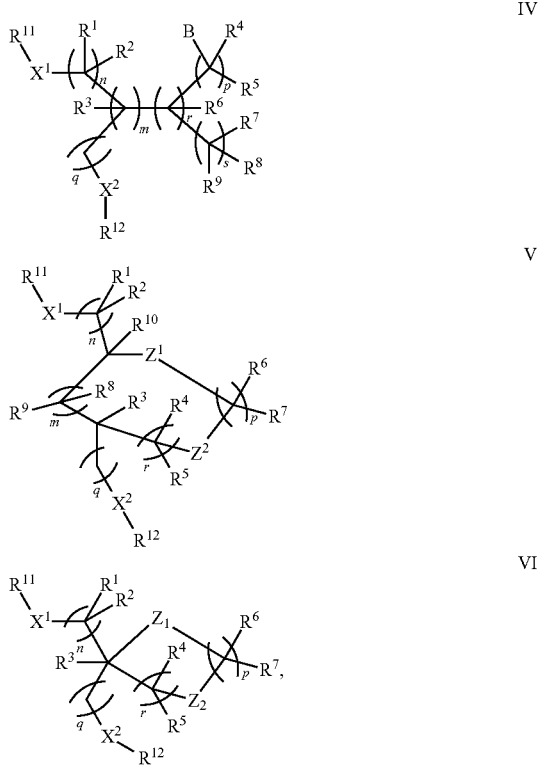

or isomers thereof, wherein: each B is independently H or a nucleobase; $X^1$ and $X^2$ are independently for each occurrence absent, O, S, or NR'; each of R$^1$, R$^2$, R$^3$, R$^4$, R$^5$, R$^6$, R$^7$, R$^8$, R$^9$ and R$^{10}$ is independently for each occurrence H, halo, OR$^{13}$, N(R')(R"), alkyl, alkenyl, alkynyl, aryl, heteroaryl, cyclyl, heterocyclyl, ω-amino alkyl, ω-hydroxy alkyl, ω-hydroxy alkenyl, or ω-hydroxy alkynyl each of which can be optionally substituted; $R^{11}$ and $R^{12}$ are independently for each occurrence H,

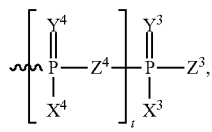

nucleoside, oligonucleotide,

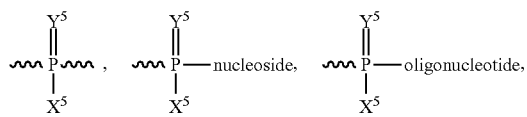

—O-oligonucleotide, —S-oligonucleotide, —S—S-oligonucleotide, —N(R')—C($Z^6$)-oligonucleotide, —C($Z^6$)—N(R')-oligonucleotide, —N(R')—C($Z^6$)$Z^6$-oligonucleotide, —$Z^6$C($Z^6$)—N(R')-oligonucleotide, N(R')C($Z^6$)N(R')-oligonucleotide,

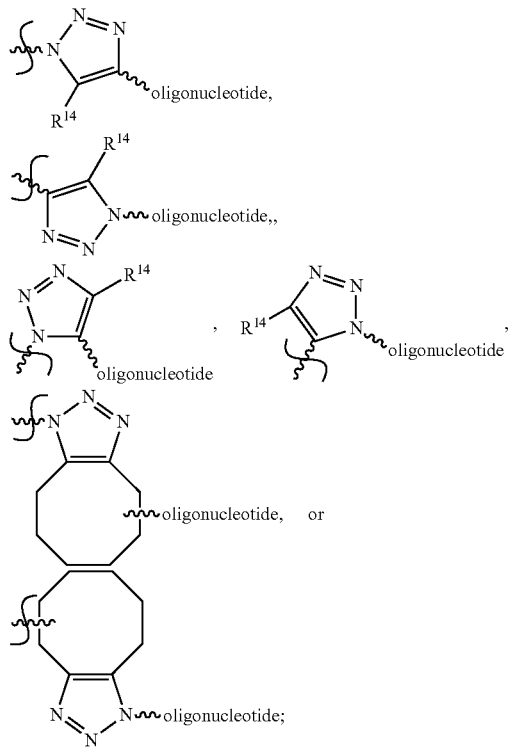

$R^{13}$ is independently for each occurrence H, alkyl, alkenyl, alkynyl, cycloalkyl, heterocyclyl, aryl, heteroaryl, heteroaryl, aralkyl, ω-amino alkyl, ω-hydroxy alkyl, or ω-hydroxy alkenyl, each of which can be optionally substituted; $R^{14}$ is independently for each occurrence H, halo, $OR^{12}$, N(R')(R''), alkyl, alkenyl, alkynyl, aryl, heteroaryl, cyclyl, heterocyclyl, ω-amino alkyl, ω-hydroxy alkyl, or ω-hydroxy alkenyl, each of which can be optionally substituted; $X^3$, $X^4$, $X^5$, and $Z^3$ are each independently for each occurrence H, O⁻, OM, $OR^{13}$, S⁻, $SR^{13}$, SM, N(R')(R''), B($R^{13}$)$_3$, $BH_3^-$, or Se; $Z^1$ and $Z^2$ are each independently O, S, N(R'), C($R^9$)($R^{10}$), C($R^9$)($OR^{13}$), C(O), or C(S); $Y^3$, $Y^4$, $Y^5$, and $Z^6$ are each independently for each occurrence O or S; $Z^4$ is independently for each occurrence O, S, $CH_2$, NR'; each of R' and R'' is independently for each occurrence H, alkyl, alkenyl, alkynyl, aryl, heteroaryl, cyclyl, heterocyclyl, ω-amino alkyl, ω-hydroxy alkyl, ω-hydroxy alkenyl, or ω-hydroxy alkynyl, each of which can be optionally substituted; each of m, n, p, q, r, and s is independently for each occurrence 0-10; t is 0-2; and M is an organic or inorganic cation.

Several studies have found the presence of a phosphate at the 5'-end siRNAs and microRNAs to be crucial for the efficient assembly of these small RNAs into the RISC (Nykanen, A., Haley, B. & Zamore, P. D. ATP requirements and small interfering RNA structure in the RNA interference pathway. Cell 107, 309-321 (2001); Elbashir, S. M., Martinez, J., Patkaniowska, A., Lendeckel, W. & Tuschl, T. Functional anatomy of siRNAs for mediating efficient RNAi in *Drosophila melanogaster* embryo lysate. EMBO J. 20, 6877-6888 (2001); Chiu, Y. L. & Rana, T. M. RNAi in human cells: basic structural and functional features of small interfering RNA. Mol. Cell. 10, 549-561 (2002); and Liu, J. et al. Argonaute2 is the catalytic engine of mammalian RNAi. Science 305, 1437-1441 (2004)). Moreover, the 5' phosphate group is seen to be essential for slicing fidelity, because the position of the cleavage site in the target RNA strand is determined by its distance from the 5' phosphate group of the guide RNA strand (Elbashir, S. M., Martinez, J., Patkaniowska, A., Lendeckel, W. & Tuschl, T. Functional anatomy of siRNAs for mediating efficient RNAi in *Drosophila melanogaster* embryo lysate. EMBO J. 20, 6877-6888 (2001); Rivas, F. V. et al. Purified Argonaute2 and an siRNA form recombinant human RISC. Nature Struct. Mol. Biol. 12, 340-349 (2005); and Elbashir, S. M. et al. Duplexes of 21-nucleotide RNAs mediate RNA interference in cultured mammalian cells. Nature 411, 494-498 (2001).

Accordingly, in some embodiments, when an abasic and/or acyclic nucleotide monomer described herein is present at the 5'-end terminal position, $R^{11}$ is

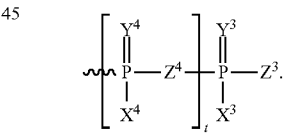

In some further embodiments of this, t is 0.

In some embodiments, $R^{11}$ is

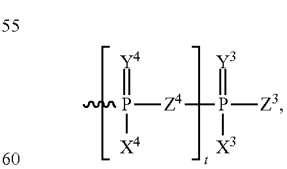

wherein t is 0; $X^3$ and $Z3^4$ are independently O, S, or N(R')(R''); and $Y^3$ is O.

When, an abasic and/or acyclic nucleotide monomer described herein is present at the 3'-end terminal position, $R^{12}$ is H.

In some embodiments, the oligonucleotide comprises at least one monomer of formula (IV'):

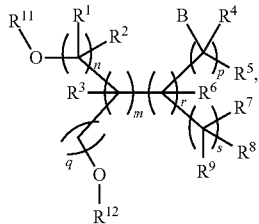

IV' wherein the variables are as defined above.

In some embodiments, the oligonucleotide comprises at least one monomer of formula (V'):

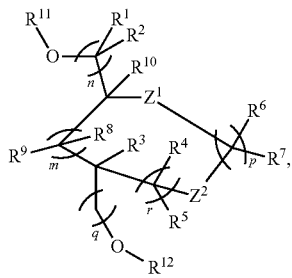

V' wherein the variables are as defined above.

In some embodiments, the oligonucleotide comprises at least one monomer of formula (VI'):

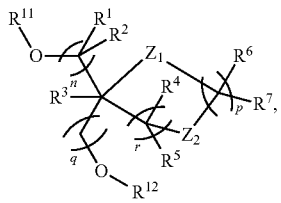

VI' wherein the variables are as defined above.

In some embodiments, the oligonucleotide comprises at least one monomer of formula (VII), (VIII), or (IX):

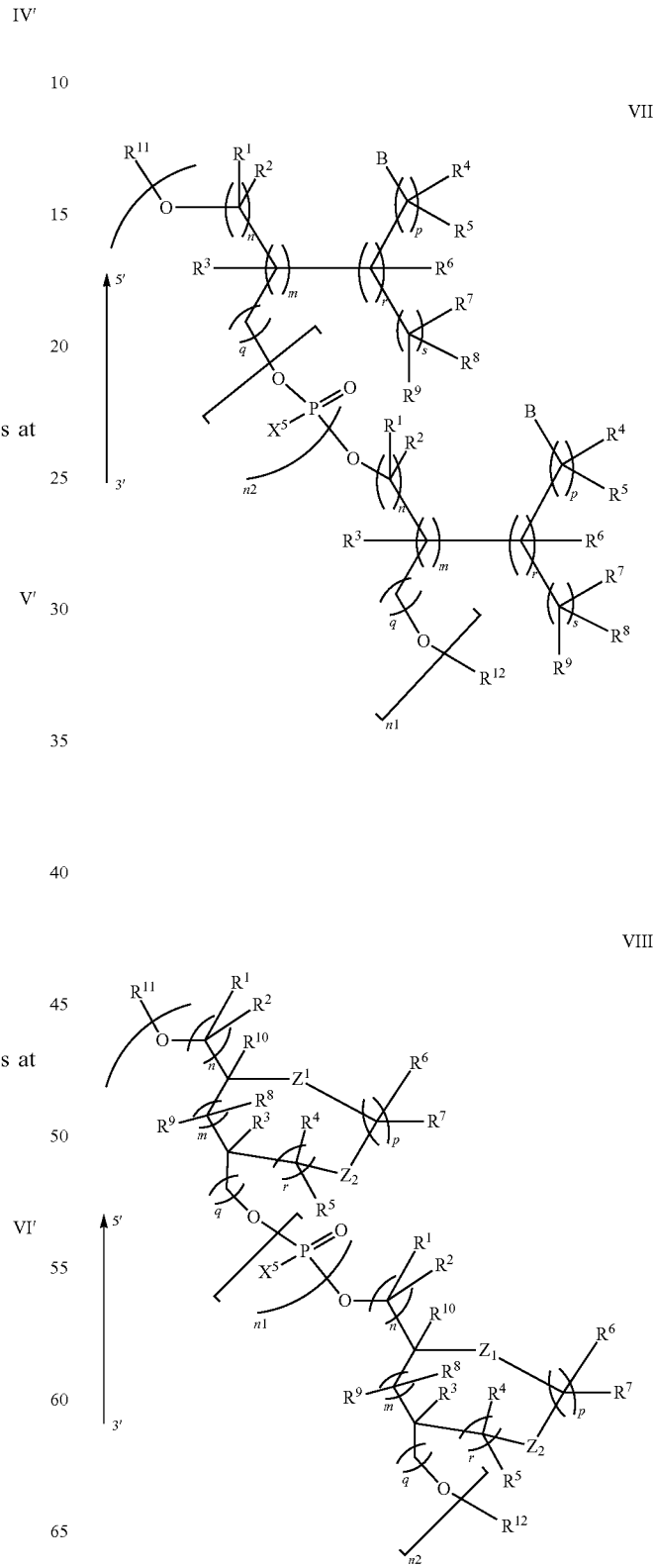

VII

VIII

-continued

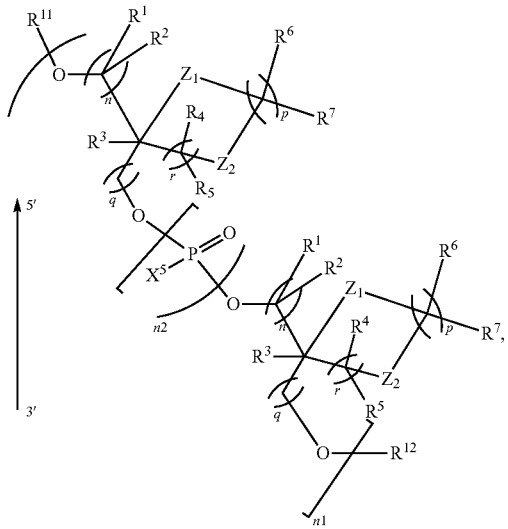

IX or isomers thereof,
wherein:
each B is independently H or a nucleobase; each of $R^1$, $R^2$, $R^3$, $R^4$, $R^5$, $R^6$, $R^7$, $R^8$, $R^9$ and $R^{10}$ is independently for each occurrence H, halo, $OR^{13}$, $N(R')(R'')$, alkyl, alkenyl, alkynyl, aryl, heteroaryl, cyclyl, heterocyclyl, ω-amino alkyl, ω-hydroxy alkyl, ω-hydroxy alkenyl, or ω-hydroxy alkynyl each of which can be optionally substituted; $R^{11}$ and $R^{12}$ are independently for each occurrence H,

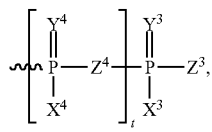

nucleoside, oligonucleotide,

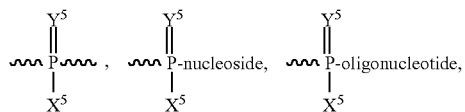

—O-oligonucleotide, —S-oligonucleotide, —S—S-oligonucleotide, —N(R')—C($Z^6$)-oligonucleotide, —C($Z^6$)—N(R')-oligonucleotide, —N(R')—C($Z^6$)$Z^6$-oligonucleotide, —$Z^6$C($Z^6$)—N(R')-oligonucleotide, N(R')C($Z^6$)N(R')-oligonucleotide,

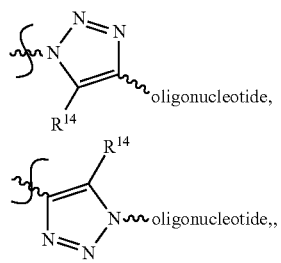

-continued

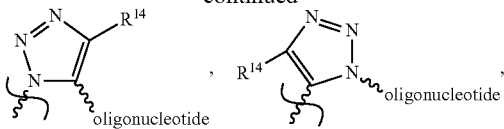

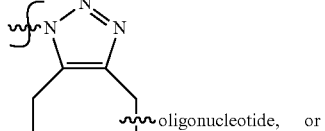

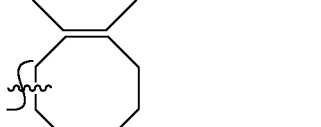

$R^{13}$ is independently for each occurrence H, alkyl, alkenyl, alkynyl, cycloalkyl, heterocyclyl, aryl, heteroaryl, heteroaryl, aralkyl, ω-amino alkyl, ω-hydroxy alkyl, or ω-hydroxy alkenyl, each of which can be optionally substituted; $R^{14}$ is independently for each occurrence H, halo, $OR^{12}$, $N(R')(R'')$, alkyl, alkenyl, alkynyl, aryl, heteroaryl, cyclyl, heterocyclyl, ω-amino alkyl, ω-hydroxy alkyl, or ω-hydroxy alkenyl, each of which can be optionally substituted $X^3$, $X^4$, $X^5$, and $Z^3$ are each independently for each occurrence H, $O^-$, OM, $OR^{13}$, $S^-$, $SR^{13}$, SM, $N(R')(R'')$, $B(R^{13})_3$, $BH_3^-$, or Se; $Z^1$ and $Z^2$ are each independently O, S, N(R'), C($R^9$)($R^{10}$), C($R^9$)($OR^{13}$), C(O), or C(S); $Y^3$, $Y^4$, $Y^5$, and $Z^6$ are each independently for each occurrence O or S; $Z^4$ is independently for each occurrence O, S, $CH_2$, NR'; each of R' and R" is independently for each occurrence H, alkyl, alkenyl, alkynyl, aryl, heteroaryl, cyclyl, heterocyclyl, ω-amino alkyl, ω-hydroxy alkyl, ω-hydroxy alkenyl, or ω-hydroxy alkynyl, each of which can be optionally substituted; each of m, n, p, q, r, and s is independently for each occurrence 0-10; t is 0-2; n1 and n2 are independently 0-49, provided that if n1 is present then n2 is absent and if n2 is present then n1 is absent; and M is an organic or inorganic cation.

In some embodiments n1 and n2 are independently 0-20.

In some embodiments, the oligonucleotides comprising the monomers of the above formulas (IV), (V), (VI), (IV'), (V'), (VI'), (VII), (VIII), or (IX) can be single stranded siRNA, double stranded siRNA, micro RNA, antimicroRNA, aptamer or antisense oligonucleotide containing a motif selected from the modifications described herein and combinations of modifications thereof. The oligonucleotide is one of the strands or constitutes both strands of a double-stranded siRNA. In one occurence the oligonucleotide is the guide or antisense strand and in another occurence the oligonucleotide is the sense or passenger strand of the double stranded siRNA.

The oligonucleotides containing the monomers of any of the above formulas can also be used in a method of inhibiting the expression of a target gene in a cell. Such method comprises contacting the cell with the oligonucleotide comprising the monomers of any of the above formulas.

When an oligonucleotide comprises two or more acyclic and/or abasic monomers described herein, they can be the same, different or any combination thereof. Such two or more monomers can be located at any position within the oligonucleotide. For example one at the 5'-end terminal position and at one or more internal positions; one at the 3'-end terminal position and at one or more internal positions; one at the 5'-end terminal position, one at the 3'-end terminal position and at one or more internal positions.

In some embodiments, the oligonucleotide comprises at least one (e.g., 1, 2, 3, 4, 5) acyclic and/or abasic monomers described herein at the 5'-end, e.g., within the first 5, 6, 7, 8, 9 or 10 positions from said end.

In some embodiments, the oligonucleotide comprises at least one (e.g., 1, 2, 3, 4, 5) acyclic and/or abasic monomers described herein at the 3'-end, e.g., within the first 5, 6, 7, 8, 9 or 10 positions from said end.

In some embodiments, the oligonucleotide comprises two acyclic and/or abasic monomers described herein within the first two positions at the 3'-end. In some further embodiments of this the intersugar linkage between the two acyclic and/or abasic monomers is non-phosphodiester linkage, e.g., a non-phosphodiester internucleoside linkage selected from the group consisting of phosphorothioate, phosphorodithioate, H-phosphonate, alkyl-phosphonate, phosphoramidate internucleoside linkages, and any combinations thereof.

In some embodiments, the monomers described herein are linked to the rest of the oligonucleotide via a non-phosphodiester intersugar linkage, e.g. a non-phosphodiester internucleoside linkage selected from the group consisting of phosphorothioate, phosphorodithioate, H-phosphonate, alkyl-phosphonate, phosphoramidate internucleoside linkages, and any combinations thereof.

Furthermore when two or more acyclic and/or abasic monomers described herein, they can be in a continuous chain, alternate with one or more other non acyclic and/or abasic nucleosides, or any combination thereof.

In some embodiments, an oligonucleotide of the invention comprises: (a) 1-20 first-type regions, each first-type region independently comprising 1-20 contiguous nucleosides wherein each nucleoside of each first-type region comprises a first-type modification; (b) 0-20 second-type regions, each second-type region independently comprising 1-20 contiguous nucleosides wherein each nucleoside of each second-type region comprises a second-type modification; and (c) 0-20 third-type regions, each third-type region independently comprising 1-20 contiguous nucleosides wherein each nucleoside of each third-type region comprises a third-type modification; wherein the first-type modification, the second-type modification, and the third-type modification are each independently selected from 2'-F, 2'-OCH$_3$, 2'-O(CH$_2$)2OCH$_3$, BNA, F—HNA, 2'-H and 2'-OH.

The monomers and oligonucleotides described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms.

Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

In some embodiments, an oligonucleotide of the invention comprises 5' phosphorothioate or 5'-phosphorodithioate, nucleotides 1 and 2 having cationic modifications via C-5 position of pyrimidines, 2-Position of Purines, N2-G, G-clamp, 8-position of purines, 6-position of purines, internal nucleotides having a 2'-F sugar with base modifications (Pseudouridine, G-clamp, phenoxazine, pyridopyrimidines, gem2'-Me-up/2'-F-down), 3'-end with two purines with novel 2'-substituted MOE analogs, 5'-end nucleotides with novel 2'-substituted MOE analogs, 5'-end having a 3'-F and a 2'-5'-linkage, 4'-substituted nucleoside at the nucleotide 1 at 5'-end and the substituent is cationic, alkyl, alkoxyalkyl, thioether and the like, 4'-substitution at the 3'-end of the strand, and combinations thereof.

In some embodiments, the oligonucleotide is a single-stranded oligonucleotide.

In some embodiments, the oligonucleotide is a double-stranded oligonucleotide.

In some embodiments, the oligonucleotide has a hairpin structure.

In some embodiments, the oligonucleotide has a dumbbell structure.

In some embodiments, the oligonucleotide is an RNAi agent, an antisense, a microRNA, a pre-microRNA, a supermir, an antimir, an antagomir, a ribozyme, a decoy oligonucleotide, an immunostimulatory oligonucleotide, RNA activator, U1 adaptor or an aptamer oligonucleotide.

In some embodiments, the oligonucleotide is a single-stranded RNAi agent.

In some embodiments, the oligonucleotide is a double-stranded RNAi agent.

In some embodiments, the oligonucleotide comprises at least one modification. In some embodiments, the modification is selected from the group consisting of a sugar modification, a non-phosphodiester intersugar (or internucleoside) linkage, nucleobase modification, and ligand conjugation.

In some embodiments, the oligonucleotide comprises at least two different modifications selected from the group consisting of a sugar modification, a non-phosphodiester intersugar linkage, nucleobase modification, and ligand conjugation. In some embodiments, the at least two different modifications are present in the same subunit of the oligonucleotide, e.g. present in the same nucleotide.

In some embodiments, the oligonucleotide is a double-stranded oligonucleotide and at least one strand comprises at least one modification. In some embodiments, sense strand comprises at least one modification. In another embodiment, antisense strand comprises at least one modification. In yet another embodiment, only the sense strand comprises at least one modification. In still yet another embodiment, only the antisense strand comprises at least one modification.

In some embodiments, sense strand comprises at least one acyclic and/or abasic nucleoside described herein. In another embodiment, antisense strand comprises at least one acyclic and/or abasic nucleoside described herein. In yet another embodiment, both the sense and the antisense strands each comprise at least one acyclic and/or abasic nucleoside described herein.

When the oligonucleotide is double-stranded and each strand comprises at least one at least one acyclic and/or abasic nucleoside described herein, such nucleosides can both be located on one end of the duplex (5'-end of one strand and 3'-end of the other strand), at opposite ends (5'-end of both strands or 3'-end of both strands), one at the end and one in the middle (5' or 3' end of one strand and an internal position of the other strand).

In some embodiments, both strands of the double-stranded oligonucleotide comprise at least one modification each. In another embodiment, both strands of the double-stranded oligonucleotide comprise at least one modification that is the same in both strands. In yet another embodiment, both strands of the double-stranded oligonucleotide comprise the same modification.

In some embodiment, the oligonucleotide comprises at least one ligand conjugate. In some embodiments, the oligonucleotide is a double-stranded oligonucleotide and only one strand comprises the ligand conjugate. In a further embodiment, the strand is sense strand. In another embodiment, the strand is antisense strand.

In yet another embodiment, both strands of a double-stranded oligonucleotide comprise at least one ligand conjugate. In some embodiments, the ligand conjugate is same in both strands. In another embodiment, the ligand is different between the two strands.

In some embodiments, the oligonucleotide comprises two or more ligand conjugates. When two or more ligands are present, the two or more ligands can be same ligand, different ligands, same type of ligand (e.g., targeting ligand, endosomolytic ligand, PK modulator), different types of ligands, or a combination thereof.

In some embodiments, the RNAi agent is double stranded and only the sense strand comprises the acyclic and/or abasic monomer described herein.

In one embodiment, the RNAi agent is double stranded and only the antisense strand comprises the acyclic and/or abasic monomer described herein.

In one embodiment, the RNAi agent is double-stranded and both the sense and the antisense strands comprise at least one acyclic and/or abasic monomer described herein. When both the sense and the antisense strands comprise a acyclic and/or abasic monomer of the invention, such monomers can be same or different. Accordingly, in one embodiment, the acyclic and/or abasic monomer described herein is the same in both the sense and the antisense strands. In another embodiment, the acyclic and/or abasic monomer is different in the sense and the antisense strands Oligonucleotides In the context of this invention, the term "oligonucleotide" refers to a polymer or oligomer of nucleotide or nucleoside monomers consisting of naturally occurring bases, sugars and intersugar linkages. The term "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

The oligonucleotide as used herein can be single-stranded or double-stranded. A single-stranded oligonucleotide can have double-stranded regions and a double-stranded oligonucleotide can have single-stranded regions. Exemplary oligonucleotides include, but are not limited to structural genes, genes including control and termination regions, self-replicating systems such as viral or plasmid DNA, single-stranded and double-stranded siRNAs and other RNA interference reagents (RNAi agents or iRNA agents), shRNA, antisense oligonucleotides, ribozymes, microRNAs, microRNA mimics, supermirs, aptamers, antimirs, antagomirs, U1 adaptors, triplex-forming oligonucleotides, RNA activators, immuno-stimulatory oligonucleotides, and decoy oligonucleotides.

Double-stranded and single-stranded oligonucleotides that are effective in inducing RNA interference are also referred to as siRNA, RNAi agent, or iRNA agent, herein. These RNA interference inducing oligonucleotides associate with a cytoplasmic multi-protein complex known as RNAi-induced silencing complex (RISC). In many embodiments, single-stranded and double-stranded RNAi agents are sufficiently long that they can be cleaved by an endogenous molecule, e.g. by Dicer, to produce smaller oligonucleotides that can enter the RISC machinery and participate in RISC mediated cleavage of a target sequence, e.g. a target mRNA.

Oligonucleotides of the present invention can be of various lengths. In particular embodiments, oligonucleotides can range from about 10 to 100 nucleotides in length. In various related embodiments, oligonucleotides, single-stranded, double-stranded, and triple-stranded, can range in length from about 10 to about 50 nucleotides, from about 20 to about 50 nucleotides, from about 15 to about 30 nucleotides, from about 20 to about 30 nucleotides in length. In some embodiments, oligonucleotide is from about 9 to about 39 nucleotides in length. In some other embodiments, oligonucleotide is at least 30 nucleotides in length.

The oligonucleotides of the invention can comprise any oligonucleotide modification described herein and below. In certain instances, it can be desirable to modify one or both strands of a double-stranded oligonucleotide. In some cases, the two strands will include different modifications. In other instances, multiple different modifications can be included on each of the strands. The various modifications on a given strand can differ from each other, and can also differ from the various modifications on other strands. For example, one strand can have a modification, e.g., a modification described herein, and a different strand can have a different modification, e.g., a different modification described herein. In other cases, one strand can have two or more different modifications, and the another strand can include a modification that differs from the at least two modifications on the first strand.

Double-Stranded Oligonucleotides

The skilled person is well aware that double-stranded oligonucleotides comprising a duplex structure of between 20 and 23, but specifically 21, base pairs have been hailed as particularly effective in inducing RNA interference (Elbashir et al., EMBO 2001, 20:6877-6888). However, others have found that shorter or longer double-stranded oligonucleotides can be effective as well.

The double-stranded oligonucleotides comprise two oligonucleotide strands that are sufficiently complementary to hybridize to form a duplex structure. Generally, the duplex structure is between 15 and 30, more generally between 18 and 25, yet more generally between 19 and 24, and most generally between 19 and 21 base pairs in length. In some embodiments, longer double-stranded oligonucleotides of between 25 and 30 base pairs in length are preferred. In some embodiments, shorter double-stranded oligonucleotides of between 10 and 15 base pairs in length are preferred. In another embodiment, the double-stranded oligonucleotide is at least 21 nucleotides long.

In some embodiments, the double-stranded oligonucleotide comprises a sense strand and an antisense strand, wherein the antisense RNA strand has a region of complementarity which is complementary to at least a part of a target sequence, and the duplex region is 14-30 nucleotides in length. Similarly, the region of complementarity to the target sequence is between 14 and 30, more generally between 18 and 25, yet more generally between 19 and 24, and most generally between 19 and 21 nucleotides in length.

The phrase "antisense strand" as used herein, refers to an oligonucleotide that is substantially or 100% complementary to a target sequence of interest. The phrase "antisense strand" includes the antisense region of both oligonucleotides that are formed from two separate strands, as well as unimolecular oligonucleotides that are capable of forming hairpin or dumbbell type structures. The terms "antisense strand" and "guide strand" are used interchangeably herein.

The phrase "sense strand" refers to an oligonucleotide that has the same nucleoside sequence, in whole or in part, as a target sequence such as a messenger RNA or a sequence of DNA. The terms "sense strand" and "passenger strand" are used interchangeably herein.

By "target sequence" is meant any nucleic acid sequence whose expression or activity is to be modulated. The target nucleic acid can be DNA or RNA, such as endogenous DNA or RNA, viral DNA or viral RNA, or other RNA encoded by a gene, virus, bacteria, fungus, mammal, or plant.

By "specifically hybridizable" and "complementary" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al, 1987, *CSH Symp. Quant. Biol. LII pp.* 123-133; Frier et al., 1986, *Proc. Nat. Acad. Sci. USA* 83:9373-9377; Turner et al., 1987, *J. Am. Chem. Soc.* 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleoside units of two strands can hydrogen bond with each other. "Substantial complementarity" refers to polynucleotide strands exhibiting 90% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

In many embodiments, the double-stranded oligonucleotide is sufficiently large that it can be cleaved by an endogenous molecule, e.g., by Dicer, to produce smaller double-stranded oligonucleotides, e.g., RNAi agents. In some embodiments, the double-stranded oligonucleotide modulates the expression of a target gene via RISC mediated cleavage of the target sequence.

In some embodiments, the double-stranded region of a double-stranded oligonucleotide is equal to or at least, 10, 11, 12, 13, 14, 15, 16, 17, 18, 19, 20, 21, 22, 23, 23, 24, 25, 26, 27, 28, 29, or 30 nucleotide pairs in length.

In some embodiments, the antisense strand of a double-stranded oligonucleotide is equal to or at least 14, 15, 16, 17, 18, 19, 20, 21, 22, 23, 23, 24, 25, 26, 27, 28, 29, or 30 nucleotides in length.

In some embodiments, the sense strand of a double-stranded oligonucleotide is equal to or at least 10, 11, 12, 13, 14, 15, 16, 17, 18, 19, 20, 21, 22, 23, 23, 24, 25, 26, 27, 28, 29, or 30 nucleotides in length.

In some embodiments, one strand has at least one stretch of 1-5 single-stranded nucleotides in the double-stranded region. By "stretch of single-stranded nucleotides in the double-stranded region" is meant that there is present at least one nucleotidebase pair at both ends of the single-stranded stretch. In some embodiments, both strands have at least one stretch of 1-5 (e.g., 1, 2, 3, 4, or 5) single-stranded nucleotides in the double stranded region. When both strands have a stretch of 1-5 (e.g., 1, 2, 3, 4, or 5) single-stranded nucleotides in the double stranded region, such single-stranded nucleotides can be opposite to each other (e.g., a stretch of mismatches) or they can be located such that the second strand has no single-stranded nucleotides opposite to the single-stranded oligonucleotides of the first strand and vice versa (e.g., a single-stranded loop). In some embodiments, the single-stranded nucleotides are present within 8 nucleotides from either end, for example 8, 7, 6, 5, 4, 3, or 2 nucleotide from either the 5' or 3' end of the region of complementarity between the two strands.

In some embodiments, each strand of the double-stranded oligonucleotide has a ZXY structure, such as is described in International Application No. PCT/US2004/07070 filed on Mar. 8, 2004, contents of which are hereby incorporated in their entireties.

Hairpins and Dumbbells

The present invention also includes double-stranded oligonucleotide wherein the two strands are linked together. The two strands can be linked to each other at both ends, or at one end only. By linking at one end is meant that 5'-end of first strand is linked to the 3'-end of the second strand or 3'-end of first strand is linked to 5'-end of the second strand. When the two strands are linked to each other at both ends, 5'-end of first strand is linked to 3'-end of second strand and 3'-end of first strand is linked to 5'-end of second strand. The two strands can be linked together by an oligonucleotide linker including, but not limited to, $(N)_n$; wherein N is independently a modified or unmodified nucleotide and n is 3-23. In some embodimentns, n is 3-10, e.g., 3, 4, 5, 6, 7, 8, 9, or 10. In some embodiments, the oligonucleotide linker is selected from the group consisting of GNRA, $(G)_4$, $(U)_4$, and $(dT)_4$, wherein N is a modified or unmodified nucleotide and R is a modified or unmodified purine nucleotide. Some of the nucleotides in the linker can be involved in base-pair interactions with other nucleotides in the linker. The two strands can also be linked together by a non-nucleosidic linker, e.g. a linker described herein. It will be appreciated by one of skill in the art that any oligonucleotide chemical modifications or variations describe herein can be used in the oligonucleotide linker.

Hairpin and dumbbell type RNAi agents will have a duplex region equal to or at least 14, 15, 15, 16, 17, 18, 19, 29, 21, 22, 23, 24, or 25 nucleotide pairs. The duplex region can be equal to or less than 200, 100, or 50, in length. In some embodiments, ranges for the duplex region are 15-30, 17 to 23, 19 to 23, and 19 to 21 nucleotides pairs in length.

In some embodiments, the hairpin oligonucleotides can mimic the natural precursors of microRNAs.

The hairpin RNAi agents can have a single strand overhang or terminal unpaired region, in some embodiments at the 3', and in some embodiments on the antisense side of the hairpin. In some embodiments, the overhangs are 1-4, more generally 2-3 nucleotides in length.

In some embodiments of hairpin RNAi agents, 3'-end of antisense is linked to 5'-end of sense strand. In some embodiments of hairpin RNAi agents, 5'-end of antisense is linked to 3'-end of sense strand.

The hairpin oligonucleotides are also referred to as "shRNA" herein.

Single-Stranded Oligonucleotides

The single-stranded oligonucleotides of the present invention also comprise nucleotide sequence that is substantially complementary to a "sense" nucleic acid encoding a gene expression product, e.g., complementary to the coding strand of a double-stranded cDNA molecule or complementary to an RNA sequence, e.g., a pre-mRNA, mRNA, miRNA, or pre-miRNA. The single-stranded oligonucleotides of the invention include antisense oligonucleotides and single-stranded RNAi agents. The region of complementarity is less than 30 nucleotides in length, and at least 15 nucleotides in length. Generally, the single stranded oligonucleotides are 10 to 25 nucleotides in length (e.g., 11, 12, 13, 14, 15, 16, 18, 19, 20, 21, 22, 23, or 24 nucleotides in length). In some embodiments the strand is 25-30 nucleotides. In some embodiments, the single-stranded oligonucleotide is 15-29 nucleotides in length. Single strands having less than 100% complementarity to the mRNA, RNA or DNA are also embraced by the present invention. In some embodiments, the single-stranded oligonucleotide has a ZXY structure, such as is described in International Application No. PCT/US2004/07070 filed on Mar. 8, 2004.

The single-stranded oligonucleotide can hybridize to a complementary RNA, e.g., mRNA, pre-mRNA, and prevent access of the translation machinery to the target RNA transcript, thereby preventing protein synthesis. The single-stranded oligonucleotide can also hybridize to a complementary RNA and the RNA target can be subsequently cleaved by an enzyme such as RNase H and thus preventing translation of target RNA. In other embodiments, the single-stranded oligonucleotide modulates the expression of a target gene via RISC mediated cleavage of the target sequence.

A "single-stranded RNAi agent" as used herein, is an RNAi agent which is made up of a single molecule. A single-stranded RNAi agent can include a duplexed region, formed by intra-strand pairing, e.g., it can be, or include, a hairpin or pan-handle structure. Single-stranded RNAi agents can be antisense with regard to the target molecule. A single-stranded RNAi agent can be sufficiently long that it can enter the RISC and participate in RISC mediated cleavage of a target mRNA. Single-straned siRNAs (ss siRNAs) are knonw and are described in U.S. Pat. Pub. No. 2006/0166901, contents of which are herein incoporated by reference in its entirety.

A single-strand RNAi agent is at least 14, and in other embodiments at least 15, at least 20, at least 25, at least 29, at least 35, at least 40, or at least 50 nucleotides in length. In some embodiments, it is less than 200, 100, or 60 nucleotides in length. In some embodiments single-stranded RNAi agents are 5' phosphorylated or include a phosphoryl analog at the 5' prime terminus. Preferably, the single-stranded RNAi agent has length from 15-29 nucleotides.

In some embodiments, single-stranded RNAi agents or at least one strand of the double-stranded RNAi agent, includes at least one of the following motifs: (a) 5'-phosphorothioate or 5'-phosphorodithioate; (b) a cationic modification of nucleotides 1 and 2 on the 5' terminal, wherein the cationic modification is at C5 position of pyrimidines and C2, C6, C8, exocyclic N2 or exocyclic N6 of purines; (c) at least one G-clamp nucleotide in the first two terminal nucleotides at the 5' end and the other nucleotide having a cationic modification, wherein the cationic modification is at C5 position of pyrimidines or C2, C6, C8, exocyclic N2 or exocyclic N6 position of purines; (d) at least one 2'-F modified nucleotide comprising a nucleobase base modification; (e) at least one gem-2'-O-methyl/2'-F modified nucleotide comprising a nucleobase modification, preferably the methyl substituent is in the up configuration, e.g. in the arabinose configuration; (f) a 5'-PuPu-3' dinucleotide at the 3' terminal wherein both nucleotides comprise a modified MOE at 2'-position as described in U.S. Provisional App. No. 61/226,017 filed Jul. 16, 2009; (g) a 5'-PuPu-3' dinucleotide at the 5' terminal wherein both nucleotides comprise a modified MOE at 2'-position as described in U.S. Provisional Appl. No. 61/226,017 filed Jul. 16, 2009; (h) nucleotide at the 5' terminal having a modified MOE at 2'-position as described in U.S. Provisional Appl. No. 61/226,017 filed Jul. 16, 2009; (i) nucleotide at the 5' terminal having a 3'-F modification; (j) 5' terminal nucleotide comprising a 4'-substituent; (k) 5' terminal nucleotide comprising a O4' modification; (l) 3' terminal nucleotide comprising a 4'-substituent; and (m) combinations thereof.

In some embodiments, both strands of a double stranded oligonucleotide independently comprise at least one of the above described motifs. In some other embodiments, both strands of a double stranded oligonucleotide comprise at least one Single-stranded oligonucleotides, including those described and/or identified as single stranded siRNAs, microRNAs or mirs which may be used as targets or may serve as a template for the design of oligonucleotides of the invention are taught in, for example, Esau, et al. US Publication #20050261218 (U.S. Ser. No. 10/909,125) entitled "Oligonucleotides and compositions for use in modulation small non-coding RNAs" the entire contents of which is incorporated herein by reference. It will be appreciated by one of skill in the art that any oligonucleotide chemical modifications or variations describe herein also apply to single stranded oligonucleotides.

MicroRNAs

MicroRNAs (miRNAs or mirs) are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

MicroRNAs have also been implicated in modulation of pathogens in hosts. For example, see Jopling, C. L., et al., *Science* (2005) vol. 309, pp 1577-1581. Without wishing to be bound by theory, administration of a microRNA, microRNA mimic, and/or anti microRNA oligonucleotide, leads to modulation of pathogen viability, growth, development, and/or replication. In some embodiments, the oligonucleotide is a microRNA, microRNA mimic, and/or anti microRNA, wherein microRNA is a host microRNA.

The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. NAR, 2006, 34, Database Issue, D140-D144; "*The microRNA Registry*" Griffiths-Jones S, NAR, 2004, 32, Database Issue, D109-D111; and also on the worldwide web at http://microrna.dot-.sanger.dot.ac.dot.uk/sequences/.

Ribozymes

Ribozymes are oligonucleotides having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes can be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Aptamers

Aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9 (1999), and Hermann and Patel, Science 287:820-5 (2000). Aptamers can be RNA or DNA based. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer can be prepared by any known method, including synthetic, recombinant, and purification methods, and can be used alone or in combination with other aptamers specific for the same target. Further, as described more fully herein, the term "aptamer" specifically includes "secondary aptamers" containing a consensus sequence derived from comparing two or more known aptamers to a given target.

Decoy Oligonucleotides

Because transcription factors recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to up-regulate genes that are suppressed by the binding of a transcription factor. Examples of the utilization of decoy oligonucleotides can be found in Mann et al., J. Clin. Invest., 2000, 106: 1071-1075, which is expressly incorporated by reference herein, in its entirety.

miRNA Mimics miRNA mimics represent a class of molecules that can be used to imitate the gene modulating activity of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs).

In one design, miRNA mimics are double stranded molecules (e.g., with a duplex region of between about 16 and about 31 nucleotides in length) and contain one or more sequences that have identity with the mature strand of a given miRNA. Double-stranded miRNA mimics have designs similar to as described above for double-stranded oligonucleotides.

In some embodiments, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

Supermirs

A supermir refers to an oligonucleotide, e.g., single stranded, double stranded or partially double stranded, which has a nucleotide sequence that is substantially identical to an miRNA and that is antisense with respect to its target. This term includes oligonucleotides which comprise at least one non-naturally-occurring portion which functions similarly. In a preferred embodiment, the supermir does not include a sense strand, and in another preferred embodiment, the supermir does not self-hybridize to a significant extent. An supermir featured in the invention can have secondary structure, but it is substantially single-stranded under physiological conditions. A supermir that is substantially single-stranded is single-stranded to the extent that less than about 50% (e.g., less than about 40%, 30%, 20%, 10%, or 5%) of the supermir is duplexed with itself. The supermir can include a hairpin segment, e.g., sequence, preferably at the 3' end can self hybridize and form a duplex region, e.g., a duplex region of at least 1, 2, 3, or 4 and preferably less than 8, 7, 6, or 5 nucleotides, e.g., 5 nucleotides. The duplexed region can be connected by a linker, e.g., a nucleotide linker, e.g., 3, 4, 5, or 6 dTs, e.g., modified dTs. In another embodiment the supermir is duplexed with a shorter oligo, e.g., of 5, 6, 7, 8, 9, or 10 nucleotides in length, e.g., at one or both of the 3' and 5' end or at one end and in the non-terminal or middle of the supermir.

Antimirs or miRNA Inhibitors

The terms "antimir" "microRNA inhibitor" or "miR inhibitor" are synonymous and refer to oligonucleotides or modified oligonucleotides that interfere with the activity of specific miRNAs. Inhibitors can adopt a variety of configurations including single stranded, double stranded (RNA/RNA or RNA/DNA duplexes), and hairpin designs, in general, microRNA inhibitors comprise one or more sequences or portions of sequences that are complementary or partially complementary with the mature strand (or strands) of the miRNA to be targeted, in addition, the miRNA inhibitor can also comprise additional sequences located 5' and 3' to the sequence that is the reverse complement of the mature miRNA. The additional sequences can be the reverse complements of the sequences that are adjacent to the mature miRNA in the pri-miRNA from which the mature miRNA is derived, or the additional sequences can be arbitrary sequences (having a mixture of A, G, C, U, or dT). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. MicroRNA inhibitors, when double stranded, can include mismatches between nucleotides on opposite strands. Furthermore, microRNA inhibitors can be linked to conjugate moieties in order to facilitate uptake of the inhibitor into a cell.

MicroRNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in WO2007/095387 and WO 2008/036825 each of which is incorporated herein by reference in its entirety. A person of ordinary skill in the art can select a sequence from the database for a desired miRNA and design an inhibitor useful for the methods disclosed herein.

Antagomirs

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate intersugar linkage and, for example, a cholesterol-moiety at 3'-end. In a preferred embodiment, antagomir comprises a 2'-O-methyl-modification at all nucleotides, a cholesterol moiety at 3'-end, two phosphorothioate intersugar linkages at the first two positions at the 5'-end and four phosphorothioate linkages at the 3'-end of the molecule. Antagomirs can be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein in its entirety.

U1 Adaptors

U1 adaptors inhibit polyA sites and are bifunctional oligonucleotides with a target domain complementary to a site in the target gene's terminal exon and a 'U1 domain' that binds to the U1 smaller nuclear RNA component of the U1 snRNP. See for example, Int. Pat. App. Pub. No. WO2008/121963 and Goraczniak, et al., 2008, Nature Biotechnology, 27(3), 257-263, each of which is expressly incorporated by reference herein, in its entirety. U1 snRNP is a ribonucleoprotein complex that functions primarily to direct early steps in spliceosome formation by binding to the pre-mRNA exon-intron boundary, Brown and Simpson, 1998, Annu Rev Plant Physiol Plant Mol Biol 49:77-95.

In some embodiments, the oligonucleotide of the invention is a U1 adaptor, wherein the oligonucleotide comprises at least one annealing domain (targeting domain) linked to at least one effector domain (U1 domain), wherein the annealing domain hybridizes to a target gene sequence and the effector domain hybridizes to the U1 snRNA of U1 snRNP. In some embodiments, the U1 adaptor comprises one annealing domain. In some embodiments, the U1 adaptor comprises one effector domain.

Without wishing to be bound by theory, the annealing domain will typically be from about 10 to about 50 nucleotides in length, more typically from about 10 to about 30 nucleotides or about 10 to about 20 nucleotides. In some preferred embodiments, the annealing domain is 10, 11, 12, 13, 14, 15, 16, 17, 18, 19, 20, or 21 nucleotides in length. The annealing domain may be at least 75%, at least 80%, at least 85%, at least 90%, at least 95%, at least 97%, or, more preferably, 100% complementary to the target gene. In one embodiment, the annealing domain hybridizes with a target site within the 3' terminal exon of a pre-mRNA, which includes the terminal coding region and the 3'UTR and polyadenylation signal sequences (e.g., through the polyadenylation site). In another embodiment, the target sequence is within about 500 basepair, about 250 basepair, about 100 basepair, or about 50 basepair of the poly (A) signal sequence of the pre-mRNA. In some embodiments, the annealing domain comprises 1, 2, 3, or 4, mismatches with the target gene sequence.

The effector domain may be from about 8 nucleotides to about 30 nucleotides, from about 10 nucleotides to about 20 nucleotides, or from about 10 to about 15 nucleotides in length. The U1 domain can hybridize with U1 snRNA, particularly the 5'-end and more specifically nucleotides 2-11, another embodiment, the U1 domain is perfectly complementary to nucleotides 2-11 of endogenous U1 snRNA. In some embodiments, the U1 domain comprises a nucleotide sequence selected from the group consisting of SEQ ED NO: 1 (5'-GCCAGGUAAGUAU-3'), SEQ NO: 2 (5'-CCAGGUAAGUAU-3'), SEQ ID NO: 4 (5'-CAGGYA-AGUAU-3'), SEQ ID NO: 5 (5'-CAGGUAAGU-3'), SEQ ID NO: 6 (5'-CAGGUAAG-3'), and SEQ ID NO: 7 (5'-CAGGUAA-3'), In some embodiments, the U1 domain comprises a nucleotide sequence SEQ ID NO: 8 (5'-CAG-GUAAGUA-3'). Without wishing to be bound by theory, increasing the length of the U1 domain to include basepairing, into stem 1 and/or basepairing to position 1 of U1 snRNA improves the U1 adaptors affinity to U1 snRNA.

The annealing and effector domains of the U1 adaptor can be linked such that the effector domain is at the 5' end and/or 3' end of the annealing domain. The two domains can be linked by such that the 3' end of one domain is linked to 5' end of the other domain, or 3' end of one domain is linked to 3' end of the other domain, or 5' end of one domain is linked to 5' end of the other domain. The annealing and effector domains can be linked directly to each other or by a nucleotide based or non-nucleotide based linker. When the linker is nucleotide based, the linker can comprise comprise 1, 2, 3, 4, 5, 6, 7, 8, 9, 10, up to 15, up to 20, or up to 25 nucleotides.

In some embodiments, the linker between the annealing domain and the effector domain is multivalent, e.g., trivalent, tetravalent or pentavalent. Without wishing to be bound by theory, a multivalent linker can be used to link together a single annealing domain with a plurality of adaptor domains.

It is to be understood that the U1 adaptor can comprise any oligonucleotide modification described herein. Exemplary modifications for U1 adaptors include those that increase annealing affinity, specificity, bioavailability in the cell and organism, cellular and/or nuclear transport, stability, and/or resistance to degradation.

In some embodiments, the U1 adaptor can be administered in combination with at least one other RNAi agent.

Immunostimulatory Oligonucleotides

Nucleic acids of the present invention can be immunostimulatory, including immunostimulatory oligonucleotides (single- or double-stranded) capable of inducing an immune response when administered to a subject, which can be a mammal or other patient. The immune response can be an innate or an adaptive immune response. The immune system is divided into a more innate immune system, and acquired adaptive immune system of vertebrates, the latter of which is further divided into humoral cellular components. In particular embodiments, the immune response can be mucosal.

Immunostimulatory nucleic acids are considered to be non-sequence specific when it is not required that they specifically bind to and reduce the expression of a target polynucleotide in order to provoke an immune response. Thus, certain immunostimulatory nucleic acids can comprise a sequence corresponding to a region of a naturally occurring gene or mRNA, but they can still be considered non-sequence specific immunostimulatory nucleic acids.

In some embodiments, the immunostimulatory nucleic acid or oligonucleotide comprises at least one CpG dinucleotide. The oligonucleotide or CpG dinucleotide can be unmethylated or methylated. In another embodiment, the immunostimulatory nucleic acid comprises at least one CpG dinucleotide having a methylated cytosine. In some embodiments, the nucleic acid comprises a single CpG dinucleotide, wherein the cytosine in said CpG dinucleotide is methylated.

In another embodiment, the immunostimulatory oligonucleotide comprises a phosphate or a phosphate modification at the 5'-end. Without wishing to be bound by theory, oligonucleotides with modified or unmodified 5'-phosphates induce an anti-viral or an antibacterial response, in particular, the induction of type I IFN, IL-18 and/or IL-1β by modulating RIG-I.

RNA Activators

Recent studies have found that dsRNA can also activate gene expression, a mechanism that has been termed "small RNA-induced gene activation" or RNAa. See for example Li, L. C. et al. *Proc Natl Acad Sci USA*. (2006), 103(46): 17337-42 and Li L. C. (2008). "Small RNA-Mediated Gene Activation". RNA and the Regulation of Gene Expression: A Hidden Layer of Complexity. Caister Academic Press. ISBN 978-1-904455-25-7. It has been shown that dsRNAs targeting gene promoters induce potent transcriptional activation of associated genes. Endogenous miRNA that cause RNAa has also been found in humans. Check E. Nature (2007). 448 (7156): 855-858.

Another surprising observation is that gene activation by RNAa is long-lasting. Induction of gene expression has been seen to last for over ten days. The prolonged effect of RNAa could be attributed to epigenetic changes at dsRNA target sites.

In some embodiments, the oligonucleotide is an RNA activator, wherein oligonucleotide increases the expression of a gene. In some embodiments, increased gene expression inhibits viability, growth development, and/or reproduction.

Triplex Forming Oligonucleotides

Recent studies have shown that triplex forming oligonucleotides (TFO) can be designed which can recognize and bind to polypurine/polypyrimidine regions in double-stranded helical DNA in a sequence-specific manner. These recognition rules are outline by Maher III, L. J., et al., *Science* (1989) vol. 245, pp 725-730; Moser, H. E., et al., *Science* (1987) vol. 238, pp 645-630; Beal, P. A., et al., *Science* (1992) vol. 251, pp 1360-1363; Conney, M., et al., *Science* (1988) vol. 241, pp 456-459 and Hogan, M. E., et al., EP Publication 375408. Modification of the oligonucleotides, such as the introduction of intercalators and inter-sugar linkage substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 1 12:487-94). In general, the triplex-forming oligonucleotide has the sequence correspondence:

```
oligo      3'-A G G T
duplex     5'-A G C T
duplex     3'-T C G A
```

However, it has been shown that the A-AT and G-GC triplets have the greatest triple helical stability (Reither and Jeltsch, BMC Biochem, 2002, September 12, Epub). The same authors have demonstrated that TFOs designed according to the A-AT and G-GC rule do not form non-specific triplexes, indicating that the triplex formation is indeed sequence specific.

Thus for any given sequence a triplex forming sequence can be devised. Triplex-forming oligonucleotides preferably are at least 15, more preferably 25, still more preferably 30 or more nucleotides in length, up to 50 or 100 nucleotides.

Formation of the triple helical structure with the target DNA induces steric and functional changes, blocking transcription initiation and elongation, allowing the introduction of desired sequence changes in the endogenous DNA and resulting in the specific down-regulation of gene expression. Examples of such suppression of gene expression in cells treated with TFOs include knockout of episomal supFG1 and endogenous HPRT genes in mammalian cells (Vasquez et al., Nucl Acids Res. 1999; 27: 1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both down-regulation and up-regulation of expression of endogenous genes (Seidman and Glazer, J Clin Invest 2003; 112:487-94), Detailed description of the design, synthesis and administration of effective TFOs can be found in U.S. Pat. App. Nos. 2003 017068 and 2003 0096980 to Froehler et al, and 2002

0128218 and 2002 0123476 to Emanuele et al, and U.S. Pat. No. 5,721,138 to Lawn, contents of which are herein incorporated in their entireties.

Oligonucleotide Modifications

Unmodified oligonucleotides can be less than optimal in some applications, e.g., unmodified oligonucleotides can be prone to degradation by e.g., cellular nucleases. However, chemical modifications to one or more of the subunits of oligonucleotide can confer improved properties, e.g., can render oligonucleotides more stable to nucleases. Typical oligonucleotide modifications can include one or more of: (i) alteration, e.g., replacement, of one or both of the non-linking phosphate oxygens and/or of one or more of the linking phosphate oxygens in the phosphodiester intersugar linkage; (ii) alteration, e.g., replacement, of a constituent of the ribose sugar, e.g., of the 2' hydroxyl on the ribose sugar; (iii) wholesale replacement of the phosphate moiety with "dephospho" linkers; (iv) modification or replacement of a naturally occurring base with a non-natural base; (v) replacement or modification of the ribose-phosphate backbone, e.g. peptide nucleic acid (PNA); (vi) modification of the 3' end or 5' end of the oligonucleotide, e.g., removal, modification or replacement of a terminal phosphate group or conjugation of a moiety, e.g., conjugation of a ligand, to either the 3' or 5' end of oligonucleotide; and (vii) modification of the sugar, e.g., six membered rings.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule. As described below, modifications, e.g., those described herein, can be provided as asymmetrical modifications.

A modification described herein can be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein.

The Phosphate Group

The phosphate group in the intersugar linkage can be modified by replacing one of the oxygens with a different substituent. One result of this modification to RNA phosphate intersugar linkages can be increased resistance of the oligonucleotide to nucleolytic breakdown. Examples of modified phosphate groups include phosphorothioate, phosphoroselenates, borano phosphates, borano phosphate esters, hydrogen phosphonates, phosphoroamidates, alkyl or aryl phosphonates and phosphotriesters. In some embodiments, one of the non-bridging phosphate oxygen atoms in the intersugar linkage can be replaced by any of the following: S, Se, $BR_3$ (R is hydrogen, alkyl, aryl), C (i.e. an alkyl group, an aryl group, etc. . . . ), H, $NR_2$ (R is hydrogen, optionally substituted alkyl, aryl), or OR (R is optionally substituted alkyl or aryl). The phosphorous atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligonucleotides diastereomers. Thus, while not wishing to be bound by theory, modifications to both non-bridging oxygens, which eliminate the chiral center, e.g. phosphorodithioate formation, can be desirable in that they cannot produce diastereomer mixtures. Thus, the non-bridging oxygens can be independently any one of O, S, Se, B, C, H, N, or OR (R is alkyl or aryl).

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either one of the linking oxygens or at both linking oxygens. When the bridging oxygen is the 3'-oxygen of a nucleoside, replacement with carbon is preferred. When the bridging oxygen is the 5'-oxygen of a nucleoside, replacement with nitrogen is preferred.

Modified phosphate linkages where at least one of the oxygen linked to the phosphate has been replaced or the phosphate group has been replaced by a non-phosphorous group, are also referred to as "non-phosphodiester intersugar linkage" or "non-phosphodiester linker."

Replacement of the Phosphate Group

The phosphate group can be replaced by non-phosphorus containing connectors, e.g. dephospho linkers. Dephospho linkers are also referred to as non-phosphodiester linkers herein. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include, but are not limited to, amides (for example amide-3 (3'-$CH_2$—C(=O)—N(H)-5') and amide-4 (3'-$CH_2$—N(H)—C(=O)-5')), hydroxylamino, siloxane (dialkylsiloxxane), carboxamide, carbonate, carboxymethyl, carbamate, carboxylate ester, thioether, ethylene oxide linker, sulfide, sulfonate, sulfonamide, sulfonate ester, thioformacetal (3'-S—$CH_2$—O-5'), formacetal (3'-O—$CH_2$—O-5'), oxime, methyleneimino, methykenecarbonylamino, methylenemethylimino (MMI, 3'-$CH_2$—N($CH_3$)—O-5'), methylenehydrazo, methylenedimethylhydrazo, methyleneoxymethylimino, ethers (C3'-O—C5'), thioethers (C3'-S—C5'), thioacetamido (C3'-N(H)—C(=O)—$CH_2$—S—C5', C3'-O—P(O)—O—SS—C5', C3'-$CH_2$—NH—NH—C5', 3'-NHP(O)(O$CH_3$)—O-5' and 3'-NHP(O)(O$CH_3$)—O-5' and nonionic linkages containing mixed N, O, S and $CH_2$ component parts. See for example, Carbohydrate Modifications in Antisense Research; Y. S. Sanghvi and P. D. Cook Eds. ACS Symposium Series 580; Chapters 3 and 4, (pp. 40-65). Preferred embodiments include methylenemethylimino (MMI), methylenecarbonylamino, amides, carbamate and ethylene oxide linker.

One skilled in the art is well aware that in certain instances replacement of a non-bridging oxygen can lead to enhanced cleavage of the intersugar linkage by the neighboring 2'-OH, thus in many instances, a modification of a non-bridging oxygen can necessitate modification of 2'-OH, e.g., a modification that does not participate in cleavage of the neighboring intersugar linkage, e.g., arabinose sugar, 2'-O-alkyl, 2'-F, LNA and ENA.

Preferred non-phosphodiester intersugar linkages include phosphorothioates, phosphorothioates with an at least 1%, 5%, 10%, 20%, 30%, 40%, 50%, 60%, 70%, 80%, 90% 95% or more enantiomeric excess of Sp isomer, phosphorothioates with an at least 1%, 5%, 10%, 20%, 30%, 40%, 50%, 60%, 70%, 80%, 90% 95% or more enantiomeric excess of Rp isomer, phosphorodithioates, phsophotriesters, aminoalkylphosphotrioesters, alkyl-phosphonaters (e.g., methylphosphonate), selenophosphates, phosphoramidates (e.g., N-alkylphosphoramidate), and boranophosphonates.

Replacement of Ribophosphate Backbone

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the morpholino, cyclobutyl, pyrrolidine, peptide nucleic acid (PNA), aminoethylglycyl PNA (aegPNA) and backnone-extended pyrrolidine PNA (bepPNA) nucleoside surrogates. A preferred surrogate is a PNA surrogate.

Sugar Modifications

An oligonucleotide can include modification of all or some of the sugar groups of the nucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH$_2$CH$_2$O)$_n$CH$_2$CH$_2$OR, n=1-50; "locked" nucleic acids (LNA) in which the oxygen at the 2' position is connected by (CH$_2$)$_n$, wherein n=1-4, to the 4' carbon of the same ribose sugar, preferably n is 1 (LNA) or 2 (ENA); O-AMINE or O—(CH$_2$)$_n$AMINE (n=1-10, AMINE=NH$_2$; alkylamino, dialkylamino, heterocyclyl, arylamino, diaryl amino, heteroaryl amino, diheteroaryl amino, ethylene diamine or polyamino); and O—CH$_2$CH$_2$(NCH$_2$CH$_2$NMe$_2$)$_2$.

"Deoxy" modifications include hydrogen (i.e. deoxyribose sugars, which are of particular relevance to the single-strand overhangs); halo (e.g., fluoro); amino (e.g. NH$_2$; alkylamino, dialkylamino, heterocyclyl, arylamino, diaryl amino, heteroaryl amino, diheteroaryl amino, or amino acid); NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino); —NHC(O)R (R=alkyl, cycloalkyl, aryl, aralkyl, heteroaryl or sugar); cyano; mercapto; alkyl-thio-alkyl; thioalkoxy; thioalkyl; alkyl; cycloalkyl; aryl; alkenyl and alkynyl, which can be optionally substituted with e.g., an amino functionality.

Other suitable 2'-modifications, e.g., modified MOE, are described in U.S. Provisional Application No. 61/226,017 filed Jul. 16, 2009, contents of which are herein incorporated by reference.

A modification at the 2' position can be present in the arabinose configuration The term "arabinose configuration" refers to the placement of a substituent on the C2' of ribose in the same configuration as the 2'-OH is in the arabinose.

The sugar group can comprise two different modifications at the same carbon in the sugar, e.g., gem modification. The sugar group can also contain one or more carbons that possess the opposite stereochemical configuration than that of the corresponding carbon in ribose. Thus, an oligonucleotide can include nucleotides containing e.g., arabinose, as the sugar. The monomer can have an alpha linkage at the 1' position on the sugar, e.g., alpha-nucleosides. The monomer can also have the opposite configuration at the 4'-position, e.g., C5' and H4' or substituents replacing them are interchanged with each other. When the C5' and H4' or substituents replacing them are interchanged with each other, the sugar is said to be modified at the 4' position.

Oligonucleotides can also include abasic sugars, which lack a nucleobase at C-1' or has other chemical groups in place of a nucleobase at C1'. See for example U.S. Pat. No. 5,998,203, contents of which are herein incorporated in their entirety. These abasic sugars can also be further containing modifications at one or more of the constituent sugar atoms. Oligonucleotides can also contain one or more sugars that are the L isomer, e.g. L-nucleosides. Modification to the sugar group can also include replacement of the 4'-O with a sulfur, optionally substituted nitrogen or CH$_2$ group. In some embodiments, linkage between C1' and nucleobase is in the a configuration.

Modifications can also include acyclic nucleotides, wherein a C—C bonds between ribose carbons (e.g., C1'-C2', C2'-C3', C3'-C4', C4'-O4', C1'-O4') is absent and/or at least one of ribose carbons or oxygen (e.g., C1', C2', C3', C4' or O4') are independently or in combination absent from the nucleotide. In some embodiments, acyclic nucleotide is

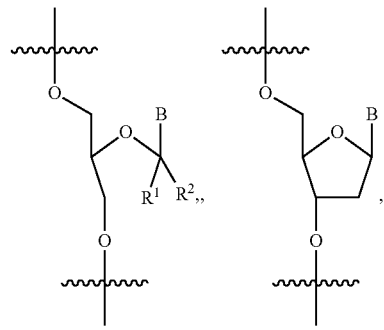

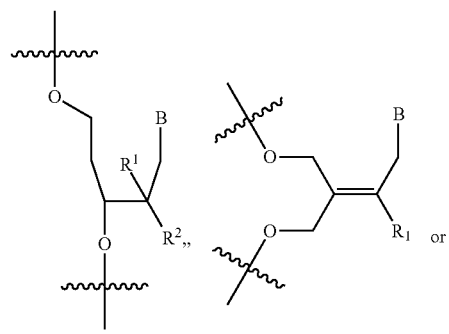

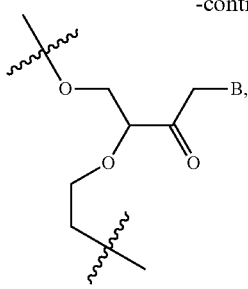

wherein B is a modified or unmodified nucleobase, $R_1$ and $R_2$ independently are H, halogen, $OR_3$, or alkyl; and $R_3$ is H, alkyl, cycloalkyl, aryl, aralkyl, heteroaryl or sugar).

Preferred sugar modifications are 2'-H, 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—$CH_2$-(4'-C) (LNA), 2'-O—$CH_2CH_2$-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE) and gem 2'-OMe/2'F with 2'-O-Me in the arabinose configuration.

It is to be understood that when a particular nucleotide is linked through its 2'-position to the next nucleotide, the sugar modifications described herein can be placed at the 3'-position of the sugar for that particular nucleotide, e.g., the nucleotide that is linked through its 2'-position. A modification at the 3' position can be present in the xylose configuration The term "xylose configuration" refers to the placement of a substituent on the C3' of ribose in the same configuration as the 3'-OH is in the xylose sugar.

The hydrogen attached to C4' and/or C1' can be replaced by a straight- or branched-optionally substituted alkyl, optionally substituted alkenyl, optionally substituted alkynyl, wherein backbone of the alkyl, alkenyl and alkynyl can contain one or more of O, S, S(O), $SO_2$, N(R'), C(O), N(R')C(O)O, OC(O)N(R'), CH(Z'), phosphorous containing linkage, optionally substituted aryl, optionally substituted heteroaryl, optionally substituted heterocyclic or optionally substituted cycloalkyl, where R' is hydrogen, acyl or optionally substituted aliphatic, Z' is selected from the group consisting of $OR_{11}$, $COR_{11}$, $CO_2R_{11}$,

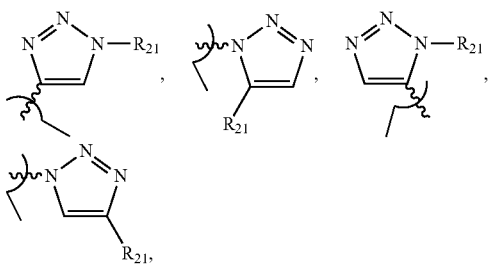

$NR_{21}R_{31}$, $CONR_{21}R_{31}$, CON(H)$NR_{21}R_{31}$, $ONR_{21}R_{31}$, CON(H)N=$CR_{41}R_{51}$, N($R_{21}$)C(=$NR_{31}$)$NR_{21}R_{31}$, N($R_{21}$C(O)$NR_{21}R_{31}$, N($R_{21}$)C(S)$NR_{21}$, OC(O)$NR_{21}R_{31}$, SC(O)$NR_{21}R_{31}$, N($R_{21}$)C(S)$OR_{11}$, N($R_{21}$)C(O)$OR_{11}$, $NR_{21}$C(O)$SR_{11}$, N($R_{21}$)N=$CR_{41}R_{51}$, ON=$CR_{41}R_{51}$, $SO_2R_{11}$, $SR_{11}$, and substituted or unsubstituted heterocyclic; $R_{21}$ and $R_{31}$ for each occurrence are independently hydrogen, acyl, unsubstituted or substituted aliphatic, aryl, heteroaryl, heterocyclic, $OR_{11}$, $COR_{11}$, $CO_2R_{11}$, or $NR_{11}R_{11}'$, or $R_{21}$ and $R_{31}$, taken together with the atoms to which they are attached, form a heterocyclic ring; $R_{41}$ and $R_{51}$ for each occurrence are independently hydrogen, acyl, unsubstituted, or substituted aliphatic, aryl, heteroaryl, heterocyclic, $OR_{11}$, $COR_{11}$, or $CO_2R_{11}$, or $NR_{11}R_{11}'$; and $R_{11}$ and $R_{11}'$ are independently hydrogen, aliphatic, substituted aliphatic, aryl, heteroaryl, or heterocyclic. In some embodiments, the hydrogen attached to the C4' of the 5' terminal nucleotide is replaced.

In some embodiments, C4' and C5' together form an optionally substituted heterocyclic, preferably comprising at least one —PX(Y)—, wherein X is H, OH, OM, SH, optionally substituted alkyl, optionally substituted alkoxy, optionally substituted alkylthio, optionally substituted alkylamino or optionally substituted dialkylamino, where M is independently for each occurrence an alki metal or transition metal with an overall charge of +1; and Y is O, S, or NR', where R' is hydrogen, optionally substituted aliphatic. Preferably this modification is at the 5 terminal of the oligonucleotide.

Terminal Modifications

The 3' and 5' ends of an oligonucleotide can be modified. Such modifications can be at the 3' end, 5' end or both ends of the molecule. For example, the 3' and/or 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a dsRNA, this array can substitute for a hairpin RNA loop in a hairpin-type RNA agent.

Terminal modifications useful for modulating activity include modification of the 5' end with phosphate or phosphate analogs. For example, in some embodiments antisense strands of dsRNAs, are 5' phosphorylated or include a phosphoryl analog at the 5' terminus. 5'-phosphate modifications include those which are compatible with RISC mediated gene silencing. Modifications at the 5'-terminal end can also be useful in stimulating or inhibiting the immune system of a subject. In some embodiments, the 5'-end of the oligonucleotide comprises the modification

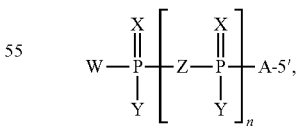

wherein W, X and Y are each independently selected from the group consisting of O, OR(R is hydrogen, alkyl, aryl), S, Se, $BR_3$ (R is hydrogen, alkyl, aryl), $BH_3^-$, C (i.e. an alkyl group, an aryl group, etc. . . . ), H, $NR_2$ (R is hydrogen, alkyl, aryl), or OR(R is hydrogen, alkyl or aryl); A and Z are each independently for each occurrence absent, O, S, $CH_2$, NR(R is hydrogen, alkyl, aryl), or optionally substituted alkylene, wherein backbone of the alkylene can comprise one or more of O, S, SS and NR(R is hydrogen, alkyl, aryl) internally and/or at the end; and n is 0-2. In some embodiments n is 1 or 2. It is understood that A is replacing the oxygen linked to 5' carbon of sugar. When n is 0, W and Y together with the P to which they are attached can form an optionally substituted 5-8 membered heterocyclic, wherein W an Y are each independently O, S, NR' or alkylene. Preferably the heterocyclic is substituted with an aryl or heteroaryl. In some embodiments, one or both hydrogen on C5' of the 5'-terminal nucleotides are replaced with a halogen, e.g., F.

Exemplary 5'-modificaitons include, but are not limited to, 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); 5'-alpha-thiotriphosphate; 5'-beta-thiotriphosphate; 5'-gamma-thiotriphosphate; 5'-phosphoramidates ((HO)$_2$(O)P—NH-5', (HO)(NH$_2$)(O)P—O-5'). Other 5'-modification include 5'-alkylphosphonates (R(OH)(O)P—O-5', R=alkyl, e.g., methyl, ethyl, isopropyl, propyl, etc. . . . ), 5'-alkyletherphosphonates (R(OH)(O)P—O-5', R=alkylether, e.g., methoxymethyl (CH$_2$OMe), ethoxymethyl, etc. . . . ). Other exemplary 5'-modifications include where Z is optionally substituted alkyl at least once, e.g., ((HO)$_2$(X)P—O[—(CH$_2$)$_a$—O—P(X)(OH)—O]$_b$-5', ((HO)$_2$(X)P—O[—(CH$_2$)$_a$—P(X)(OH)—O]$_b$-5', ((HO)$_2$(X)P—[—(CH$_2$)$_a$—O—P(X)(OH)—O]$_b$-5; dialkyl terminal phosphates and phosphate mimics: HO[—(CH$_2$)$_a$—O—P(X)(OH)—O]$_b$-5', H$_2$N[—(CH$_2$)$_a$—O—P(X)(OH)—O]$_b$-5', H[—(CH$_2$)$_a$—O—P(X)(OH)—O]$_b$-5', Me$_2$N[—(CH$_2$)$_a$—O—P(X)(OH)—O]$_b$-5', HO[—(CH$_2$)$_a$—P(X)(OH)—O]$_b$-5', H$_2$N[—(CH$_2$)$_a$—P(X)(OH)—O]$_b$-5', H[—(CH$_2$)$_a$—P(X)(OH)—O]$_b$-5', Me$_2$N[—(CH$_2$)$_a$—P(X)(OH)—O]$_b$-5', wherein a and b are each independently 1-10. Other embodiments, include replacement of oxygen and/or sulfur with BH$_3$, BH$_3^-$ and/or Se.

Terminal modifications can also be useful for monitoring distribution, and in such cases the preferred groups to be added include fluorophores, e.g., fluorescein or an Alexa dye, e.g., Alexa 488. Terminal modifications can also be useful for enhancing uptake, useful modifications for this include targeting ligands. Terminal modifications can also be useful for cross-linking an oligonucleotide to another moiety; modifications useful for this include mitomycin C, psoralen, and derivatives thereof.

Nucleobases

Adenine, cytosine, guanine, thymine and uracil are the most common bases (or nucleobases) found in nucleic acids. These bases can be modified or replaced to provide oligonucleotides having improved properties. For example, nuclease resistant oligonucleotides can be prepared with these bases or with synthetic and natural nucleobases (e.g., inosine, xanthine, hypoxanthine, nubularine, isoguanisine, or tubercidine) and any one of the above modifications. Alternatively, substituted or modified analogs of any of the above bases and "universal bases" can be employed. When a natural base is replaced by a non-natural and/or universal base, the nucleotide is said to comprise a modified nucleobase and/or a nucleobase modification herein. Modified nucleobase and/or nucleobase modifications also include natural, non-natural and universal bases, which comprise conjugated moieties, e.g. a ligand described herein. Preferred conjugate moieties for conjugation with nucleobases include cationic amino groups which can be conjugated to the nucleobase via an appropriate alkyl, alkenyl or a linker with an amide linkage.

An oligonucleotide can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as inosine, xanthine, hypoxanthine, nubularine, isoguanisine, tubercidine, 2-(halo)adenine, 2-(alkyl)adenine, 2-(propyl)adenine, 2-(amino)adenine, 2-(aminoalkyll)adenine, 2-(aminopropyl)adenine, 2-(methylthio)-N$^6$-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino)adenine, 8-(halo)adenine, 8-(hydroxyl)adenine, 8-(thioalkyl)adenine, 8-(thiol)adenine, N$^6$-(isopentyl)adenine, N$^6$-(methyl)adenine, N$^6$,N$^6$-(dimethyl)adenine, 2-(alkyl)guanine, 2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, N$^4$-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl)uracil, 5-(guanidiniumalkyl)uracil, 5-(1,3-diazole-1-alkyl)uracil, 5-(cyanoalkyl)uracil, 5-(dialkylaminoalkyl)uracil, 5-(dimethylaminoalkyl)uracil, 5-(halo)uracil, 5-(methoxy)uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, dihydrouracil, N$^3$-(methyl)uracil, 5-uracil (i.e., pseudouracil), 2-(thio)pseudouracil 4-(thio)pseudouracil, 2,4-(dithio) psuedouracil, 5-(alkyl)pseudouracil, 5-(methyl)pseudouracil, 5-(alkyl)-2-(thio)pseudouracil, 5-(methyl)-2-(thio) pseudouracil, 5-(alkyl)-4-(thio)pseudouracil, 5-(methyl)-4-(thio)pseudouracil, 5-(alkyl)-2,4-(dithio)pseudouracil, 5-(methyl)-2,4-(dithio)pseudouracil, 1-substituted pseudouracil, 1-substituted 2(thio)-pseudouracil, 1-substituted 4-(thio)pseudouracil, 1-substituted 2,4-(dithio)pseudouracil, 1-(aminocarbonylethylenyl)-pseudouracil, 1-(aminocarbonylethylenyl)-2(thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylamino-carbonylethylenyl)-2(thio)-pseudouracil, 1-(aminoalkylaminocarbonylethylenyl)-4-(thio) pseudouracil, 1-(aminoalkylaminocarbonylethylenyl)-2,4-(dithio)pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenzyl, tetracenyl, pentacenyl, difluorotolyl, 4-(fluoro)-6-(methyl)benzimidazole, 4-(methyl)benzimidazole, 6-(azo) thymine, 2-pyridinone, 5-nitroindole, 3-nitropyrrole, 6-(aza) pyrimidine, 2-(amino)purine, 2,6-(diamino)purine, 5-substituted pyrimidines, $N^2$-substituted purines, $N^6$-substituted purines, $O^6$-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof. Alternatively, substituted or modified analogs of any of the above bases and "universal bases" can be employed.

As used herein, a universal nucleobase is any modified or nucleobase that can base pair with all of the four naturally occurring nucleobases without substantially affecting the melting behavior, recognition by intracellular enzymes or activity of the oligonucleotide duplex. Some exemplary universal nucleobases include, but are not limited to, 2,4-difluorotoluene, nitropyrrolyl, nitroindolyl, 8-aza-7-deazaadenine, 4-fluoro-6-methylbenzimidazle, 4-methylbenzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylinolyl, 4,6-dimethylindolyl, phenyl, napthalenyl, anthracenyl, phenanthracenyl, pyrenyl, stilbenzyl, tetracenyl, pentacenyl, and structural derivatives thereof (see for example, Loakes, 2001, *Nucleic Acids Research*, 29, 2437-2447).

Further nucleobases include those disclosed in U.S. Pat. No. 3,687,808; those disclosed in International Application No. PCT/US09/038,425, filed Mar. 26, 2009; those disclosed in the Concise Encyclopedia Of Polymer Science And Engineering, pages 858-859, Kroschwitz, J. I., ed. John Wiley & Sons, 1990; those disclosed by English et al., Angewandte Chemie, International Edition, 1991, 30, 613; those disclosed in Modified Nucleosides in Biochemistry, Biotechnology and Medicine, Herdewijin, P.Ed. Wiley-VCH, 2008; and those disclosed by Sanghvi, Y. S., Chapter 15, dsRNA Research and Applications, pages 289-302, Crooke, S. T. and Lebleu, B., Eds., CRC Press, 1993. Contents of all of the above are herein incorporated by reference.

General References

The oligonucleotides used in accordance with this invention can be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3,2'-β-Methyloligoribonucleotides: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta*, 1995, 78, 486-504; Beaucage, S. L. and Iyer, R. P., Tetrahedron, 1992, 48, 2223-2311 and Beaucage, S. L. and Iyer, R. P., *Tetrahedron*, 1993, 49, 6123-6194, or references referred to therein. Modification described in WO 00/44895, WO01/75164, or WO02/44321 can be used herein. The disclosure of all publications, patents, and published patent applications listed herein are hereby incorporated by reference.

Phosphate Group References

The preparation of phosphinate oligonucleotides is described in U.S. Pat. No. 5,508,270. The preparation of alkyl phosphonate oligonucleotides is described in U.S. Pat. No. 4,469,863. The preparation of phosphoramidite oligonucleotides is described in U.S. Pat. No. 5,256,775 or 5,366,878. The preparation of phosphotriester oligonucleotides is described in U.S. Pat. No. 5,023,243. The preparation of boranophosphate oligonucleotide is described in U.S. Pat. Nos. 5,130,302 and 5,177,198. The preparation of 3'-Deoxy-3'-amino phosphoramidate oligonucleotides is described in U.S. Pat. No. 5,476,925. 3'-Deoxy-3'-methylenephosphonate oligonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

Sugar Group References

Modifications to the 2' modifications can be found in Verma, S. et al. Annu. Rev. Biochem. 1998, 67, 99-134 and all references therein. Specific modifications to the ribose can be found in the following references: 2'-fluoro (Kawasaki et. al., *J. Med. Chem.*, 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310).

Replacement of the Phosphate Group References

Methylenemethylimino linked oligonucleosides, also identified herein as MMI linked oligonucleosides, methylenedimethylhydrazo linked oligonucleosides, also identified herein as MDH linked oligonucleosides, and methylenecarbonylamino linked oligonucleosides, also identified herein as amide-3 linked oligonucleosides, and methyleneaminocarbonyl linked oligonucleosides, also identified herein as amide-4 linked oligonucleosides as well as mixed intersugar linkage compounds having, as for instance, alternating MMI and PO or PS linkages can be prepared as is described in U.S. Pat. Nos. 5,378,825, 5,386,023, 5,489,677 and in International Application Nos. PCT/US92/04294 and PCT/US92/04305 (published as WO 92/20822 WO and 92/20823, respectively). Formacetal and thioformacetal linked oligonucleosides can be prepared as is described in U.S. Pat. Nos. 5,264,562 and 5,264,564. Ethylene oxide linked oligonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 1 1972, 1991. Carbamate replacements are described in Stirchak, E. P. Nucleic Acids Res. 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They can also be prepared in accordance with U.S. Pat. No. 5,539,083.

Terminal Modification References

Terminal modifications are described in Manoharan, M. et al. *Antisense and Nucleic Acid Drug Development* 12, 103-128 (2002) and references therein.

Nucleobases References

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference in its entirety.

Placement of Modifications within an Oligonucleotide

As oligonucleotides are polymers of subunits or monomers, many of the modifications described herein can occur at a position which is repeated within an oligonucleotide, e.g., a modification of a nucleobase, a sugar, a phosphate moiety, or the non-bridging oxygen of a phosphate moiety. It is not necessary for all positions in a given oligonucleotide to be uniformly modified, and in fact more than one of the aforementioned modifications can be incorporated in a single oligonucleotide or even at a single nucleoside within an oligonucleotide.

In some cases the modification will occur at all of the subject positions in the oligonucleotide but in many, and in fact in most cases it will not. By way of example, a modification can occur at a 3' or 5' terminal position, can occur in the internal region, can occur in 3', 5' or both terminal regions, e.g. at a position on a terminal nucleotide or in the last 2, 3, 4, 5, 6, 7, 8, 9, or 10 nucleotides of an oligonucleotide. In some embodiments, the terminal nucleotide (e.g., 3'-terminal or preferably 5'-terminal) does not comprise a modification.

In some emodiments, the terminal nucleotide or the last 2, 3, 4, 5, 6, 7, 8, 9, or 10 nucleotides of at least one end of the oligonucleotide all comprise at least one modification. In some embodiments, the modification is same. In some emodiments, the terminal nucleotide or the last 2, 3, 4, 5, 6, 7, 8, 9, or 10 nucleotides at both ends of the oligonucleotide all comprise at least one modification. It is to be understood that type of modification and number of modified nucleotides on one end is independent of type of modification and number of modified nucleotides on the other end.

A modification can occur in a double strand region, a single strand region, or in both. A modification can occur in the double strand region of an oligonucleotide or can occur in a single strand region of an oligonucleotide. In some embodiments, a modification described herein does not occur in the region corresponding to the target cleavage site region. For example, a phosphorothioate modification at a non-bridging oxygen position can occur at one or both termini, can occur in a terminal regions, e.g., at a position on a terminal nucleotide or in the last 2, 3, 4, 5, 6, 7, 8, 9, or 10 nucleotides of a strand, or can occur in double strand and single strand regions, particularly at termini.

Some modifications can preferably be included on an oligonucleotide at a particular location, e.g., at an internal position of a strand, or on the 5' or 3' end of an oligonucleotide. A preferred location of a modification on an oligonucleotide, can confer preferred properties on the oligonucleotide. For example, preferred locations of particular modifications can confer optimum gene silencing properties, or increased resistance to endonuclease or exonuclease activity.

In some embodiments, the oligonucleotide comprises at least one (e.g., 1, 2, 3, 4, 5, 6, 7, 8, 9, or 10 or more), of 5'-5', 3'-3',3'-2', 2'-5',2'-3' or 2'-2' intersugar linkage. In some embodiments, the last nucleotide on the terminal end is linked via a 5'-5', 3'-3',3'-2', 2'-5',2'-3' or 2'-2' intersugar linkage to the rest of the oligonucleotide. In some preferred embodiments, the last nucleotide on both the terminal ends is linked via a 5'-5', 3'-3',3'-2', 2'-3' or 2'-2' intersugar linkage to the rest of the oligonucleotide. In some embodiments, at least one 5'-5', 3'-3',3'-2', 2'-5',2'-3' or 2'-2' intersugar linkage is a non-phosphodiester linkage.

5'-Pyrimidine-Purine-3' and 5'-Pyrimidine-Pyrimidine-3' Dinucleotide Motif

An oligonucleotide can comprise at least one (e.g., 1, 2, 3, 4, 5, 6, 7, 8, 9, or 10 more), 5'-pyrimidine-purine-3' (5'-PyPu-3') and/or 5'-pyrimidine-pyrimidine-3' (5'-PyPy-3') dinucleotide sequence motif, wherein the 5'-most pyrimidine ribose sugar is modified at the 2'-position. Preferred 2'-modifications include, but are not limited to, 2'-H, 2'-O-Me (2'-β-methyl), 2'-O-MOE (2'-O-methoxyethyl), 2'-F, 2'-O-[2-(methylamino)-2-oxoethyl] (2'-β-NMA), 2'-O—$CH_2CH_2N(CH_2CH_2NMe_2)_2$, 2'-S-methyl, 2'-O—$CH_2$-(4'-C) (LNA) and 2'-β-$CH_2CH_2$-(4'-C) (ENA). Double-stranded oligonucleotides including these modifications are particularly stabilized against endonuclease activity. In some embodiments, the 3' most nucleotide in the dinucleotide motif also comprises a ribose sugar which is modified at the 2'-position. When both nucleotides of the dinucleotide motif comprise ribose sugar with 2'-modification, the modification can be the same or different on the two nucleotides. In another embodiment, the 5' most pyrimidine in all occurrences of the dinucleotide motif in the oligonucleotide comprises a ribose sugar which is modified at the 2'-position. In yet another embodiment, both nucleotides in all occurrences of the dinucleotide motif comprise a ribose sugar comprising a 2'-modification. In yet another embodiment, the 5'-most pyrimidine in the dinucleotide motif is uridine. In yet still another embodiment, the 5'-most pyrimidine in the dinucleotide motif is cytidine.

In some embodiments, the oligonucleotide comprises at least one (e.g., 1, 2, 3, 4, 5, 6, 7, 8, 9, or 10 or more), 5'-PyPu-3' and/or 5'-PyPy-3' dinucleotide motif wherein the intersugar linkage between the two nucleotides is not a phosphodiester. In some embodiments, the intersugar linkage is a non-phosphodiester linkage described herein. Preferred non-phosphodiester linkages include, but are not limited to, phosphorothioate, phosphorodithioate, N-alkyl phosphoramidate, alkyl phosphonate (e.g., methyl phosphonate) and borano phosphonate. In some embodiments, the intersugar linkage between the two nucleotides in all occurrences of the dinucleotide motif is a non-phosphodiester linkage. In another embodiment, the 5'-most pyrimidine in the dinucleotide motif is uridine. In yet another embodiment, the 5'-most pyrimidine in the dinucleotide motif is cytidine.

In some embodiments, the oligonucleotide comprises at least one (e.g., 1, 2, 3, 4, 5, 6, 7, 8, 9, or 10 or more), 5'-PyPu-3' and/or 5'-PyPy-3' dinucleotide motif wherein at least one of the nucleotides comprises a nucleobase modification, e.g. a modified nucleobase or a nucleobase with one or more conjugated moieties. In some embodiments, the 5' most pyrimidine in the dinucleotide sequence motif comprises the nucleobase modification. In another embodiment, the 3' most nucleotide in the dinucleotide motif also comprises the nucleobase modification. In yet another embodiment, both nucleotides in the dinucleotide motif comprise a nucleobase modification. In some embodiments, at least one nucleotides in all occurrences of the dinucleotide motif comprises a nucleobase modification. In still another embodiment, the 5'-most pyrimidine in the dinucleotide motif is uridine. In yet still another embodiment, the 5'-most pyrimidine in the dinucleotide motif is cytidine.

In some embodiments, the oligonucleotide comprises at least one (e.g., 1, 2, 3, 4, 5, 6, 7, 8, 9, or 10 or more), 5'-PyPu-3' and/or 5'-PyPy-3' dinucleotide motif wherein the 5'-most pyrimidine ribose sugar is modified at the 2'-position and the oligonucleotide further comprises at least one of a non-phosphodiester intersugar linkage, a nucleobase modification or a 2' modification. In some embodiments, the 5'-most pyrimidines in all occurrences of the dinucleotide motif comprise a ribose sugar modified at the 2'-position, and the oligonucleotide further comprises at least one of a non-phosphodiester intersugar linkage, a nucleobase modification or a 2' modification. In further embodiments, the non-phosphodiester intersugar linkage, the nucleobase modification and/or the 2'-modification is comprised within the dinucleotide motif, e.g. the intersugar linkage between the two nucleosides of the dinucleotide motif is a non-phosphodiester intersugar linkage, one or both nucleosides comprise a nucleobase modification and/or the 3'-nucleoside of the motif comprises a 2'-modification. In some embodiments, the 5'-most pyrimidine in the dinucleotide motif is uridine. In another embodiment, the 5'-most pyrimidine in the dinucleotide motif is cytidine.

In some embodiments, the oligonucleotide comprises at least one (e.g., 1, 2, 3, 4, 5, 6, 7, 8, 9, or 10 or more), 5'-PyPu-3' and/or 5'-PyPy-3' dinucleotide motif, wherein the ribose sugar of the 5'-most pyrimidine is replaced by a non ribose moiety, e.g., a six membered ring. In some embodiments, the 5'-most pyrimidines all occurrences of the dinucleotide motif comprise a non ribose sugar, e.g. a six membered ring. In some embodiments, the 5'-most pyrimidine in the dinucleotide motif is uridine. In another embodiment, the 5'-most pyrimidine in the dinucleotide motif is cytidine.

In some embodiments, the oligonucleotide comprises at least 1, 2, 3, 4, 5, 6, 7, 8, 9, or 10, 5'-PyPu-3' and/or 5'-PyPy-3' dinucleotide motif wherein the $C^5$ position of the 5'-most pyrimidine is conjugated with a ligand, e.g. a cationic group, e.g. a cationic amino group. In some embodiments, the 5'-most pyrimidines all occurrences of dinucleotide motif are conjugated with a ligand, at the $C^5$ position, wherein each ligand is selected independently of other ligands. In another embodiment, the 5'-most pyrimidine in the dinucleotide motif is uridine. In yet another embodiment, the 5'-most pyrimidine in the dinucleotide motif is cytidine.

In some embodiments, the oligonucleotide comprises at least one (e.g., 1, 2, 3, 4, 5, 6, 7, 8, 9, or 10 or more), 5'-PyPu-3' dinucleotide wherein the $N^2$, $N^6$, and/or $C^8$ position of the purine is conjugated with a ligand, e.g. a cationic group, e.g. a cationic amino group. In some embodiments, the 3'-most purines in all occurrences of the dinucleotide motif are conjugated with a ligand at the $N^2$, $N^6$, and/or $C^8$ positions, wherein each ligand is selected independently of other ligands. In another embodiment, the 5'-most pyrimidine in the dinucleotide motif is uridine. In yet another embodiment, the 5'-most pyrimidine in the dinucleotide motif is cytidine.

In some embodiments, the oligonucleotide comprises at least one (e.g., 1, 2, 3, 4, 5, 6, 7, 8, 9, or 10 or more), 5'-PyPu-3' and/or 5'-PyPy-3' dinucleotide motif wherein both nucleotides comprise nucleobase modifications, e.g., the $C^5$ position of the pyrimidine and the $N^2$, $N^6$, and/or $C^8$ position of the purine is conjugated with a ligand, e.g. a cationic group, wherein each ligand is selected independently. In some embodiments, both nucleotides in all occurrences of the dinucleotide motif are conjugated with a ligand, wherein each ligand is selected independently of other ligands. In another embodiment, the 5'-most pyrimidine in the dinucleotide motif is uridine. In yet another embodiment, the 5'-most pyrimidine in the dinucleotide motif is cytidine.

In some embodiments, the oligonucleotide comprises at least one (e.g., 1, 2, 3, 4, 5, 6, 7, 8, 9, or 10 or more), 5'-PyPu-3' and/or 5'-PyPy-3' dinucleotide motif wherein at least one of the nucleotides comprises a nucleobase modification and neither nucleotide comprises a modification at the 2' position of the ribose sugar. In another embodiment, at least one nucleotide in all occurrences of the dinucleotide motif comprise a nucleobase modification and neither nucleotide comprises a modification at the 2' position of the ribose sugar. In yet another embodiment, both nucleotides in the dinucleotide motif comprise a nucleobase modification and neither nucleotide comprises a modification at the 2' position of the ribose sugar.

In some embodiments, the oligonucleotide comprises at least one (e.g., 1, 2, 3, 4, 5, 6, 7, 8, 9, or 10 or more), 5'-PyPu-3' and/or 5'-PyPy-3' dinucleotide motif wherein the intersugar linkage between the two nucleotides is not a phosphodiester and neither nucleotide comprises a modification at the 2' position of the ribose sugar. In some embodiments, the intersugar linkage is a non-phosphodiester linkage described herein. In some embodiments, the intersugar linkage between the two nucleotides in all occurrences of the dinucleotide motif is a non-phosphodiester linkage and neither nucleotide comprises a modification at the 2' position of the ribose sugar.

In some embodiments, the oligonucleotide comprises at least one (e.g., 1, 2, 3, 4, 5, 6, 7, 8, 9, or 10 or more), 5'-PyPu-3' and/or 5'-PyPy-3' dinucleotide motif wherein the 5'-most pyrimidine comprises a modification at the 2'-position, the intersugar linkage between the two nucleosides is a non-phosphodiester linkage and at least one of the nucleotides comprises a nucleobase modification. In some embodiments, the 5' most pyrimidine in the dinucleotide motif comprises the nucleobase modification. In another embodiment, the 3' most nucleotide in the dinucleotide motif comprises the nucleobase modification. In yet another embodiment, both the nucleotides in the dinucleotide motif comprise the nucleobase modification. In yet still another embodiment, the 5' most pyrimidine in all occurrences of the dinucleotide motif comprises a 2'-modified ribose sugar, intersugar linkage between the two nucleosides is a non-phosphodiester linkage and at least one of the nucleosides comprises a nucleobase modification.

In some embodiments, the oligonucleotide comprises at least one (e.g., 1, 2, 3, 4, 5, 6, 7, 8, 9, or 10 or more), 5'-PyPu-3' and/or 5'-PyPy-3' dinucleotide motif wherein the 3' most nucleoside comprises a modification at the 2'-position, intersugar linkage between the two nucleosides is a non-phosphodiester linkage and at least one of the nucleosides comprises a nucleobase modification. In some embodiments, the 5'-most nucleoside in the dinucleotide motif comprises the nucleobase modification. In another embodiment, the 3'-most nucleoside in the dinucleotide motif comprises the nucleobase modification. In yet another embodiment, both nucleosides in the dinucleotide comprise the nucleobase modification. In yet still another embodiment, the 3' most nucleoside in all occurrences of the dinucleotide motif comprises a 2'-modified ribose sugar, intersugar linkage between the two nucleotides is a non-phosphodiester linkage and at least one of the nucleosides comprises a nucleobase modification.

In some embodiments, oligonucleotide comprises a motif selected from the group consisting of: 2'-modified uridines in all occurrences of the sequence motif 5'-uridine-adenosine-3' (5'-UA-3'), 2'-modified uridines in all occurrences of the sequence motif 5'-uridine-guanosine-3' (5'-UG-3'), 2'-modified cytidines in all occurrences of the sequence motif 5'-cytidine-adenosine-3' (5'-CA-3'), 2'-modified cytidines in all occurrences of the sequence motif 5'-cytidine-Guanosine-3' (5'-CA-3'), 2'-modified 5'-most uridines in all occurrences of the sequence motif 5'-uridine-uridine-3' (5'-UU-3'), 2'-modified 5'-most cytidines in all occurrences of the sequence motif 5'-cytidine-cytidine-3' (5'-CC-3'), 2'-modified cytidines in all occurrences of the sequence motif 5'-cytidine-uridine-3' (5'-CU-3'), 2'-modified uridines in all occurrences of the sequence motif 5'-uridine-cytidine-3' (5'-UC-3'), and combinations thereof; and wherein the oligonucleotide further comprises at least one non-phosphodiester intersugar linkage, nucleobase modification and/or sugar modification, e.g. a 2' sugar modification. Preferably, the non-phosphodiester intersugar linkage, nucleobase modification and/or sugar modification is within the dinucleotide motif.

In some embodiments, the oligonucleotide comprises a 5'-purine-purine-3' (5'-PuPu-3') dinucleotide motif at the 5' and/or 3' terminal end, wherein both nucleoside sugars are modified, e.g., 2'-modified. In some embodiments, at least one of the purines is modified at the 2, 6, 7, 8, $N^2$ exocyclic, and/or $N^6$ exocyclic positions, or combinations thereof. In another embodiment, the intersugar linkage between the purines is a non-phosphodiester linkage.

In some embodiments, the 5' terminal nucleoside of the oligonucleotide comprises a sugar modification, e.g., a 2' modification, a 4' modification or an O4' modification, e.g., replacement of O4' with S, substituted N, NH or $CH_2$. In some embodiments, the 5' terminal nucleotide further comprises a modified nucleobase or nucleobase modification.

Overhangs

Double-stranded oligonucleotides having at least one single-stranded nucleotide overhang have unexpectedly superior inhibitory properties than their blunt-ended counterparts. As used herein, the term "overhang" refers to a double-stranded structure where at least one end of one strand is longer than the corresponding end of the other strand forming the double-stranded structure. Generally, the single-stranded overhang is located at the 3'-terminal end of the antisense strand or, alternatively, at the 3'-terminal end of the sense strand. The double-stranded oligonucleotide can also have a blunt end, generally located at the 5'-end of the antisense strand. Generally, the antisense strand of the double-stranded oligonucleotide has a single-stranded overhang at the 3'-end, and the 5'-end is blunt.

In some embodiments, at least one end of the double-stranded region has a single-stranded nucleotide overhang of 1 to 4, generally 1 or 2 nucleotides. In some embodiment, both ends of the double-stranded region have a single-stranded nucleotide overhang of 1 to 4, generally 1 or 2 nucleotides.

In some embodiments it is particularly preferred, e.g., to enhance stability, to include particular nucleobases in the single-stranded overhangs, or to include modified nucleotides or nucleotide surrogates, in single-strand overhangs. For example, it can be desirable to include purine nucleotides in overhangs. In some embodiments all or some of the bases in the single strand overhang will be modified, e.g., with a modification described herein. Modifications in the single-stranded overhangs can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence. In some embodiments, the single strand overhangs are asymmetrically modified with a modification described herein, e.g. a first single stand overhang comprises a modification that is not present in a second single strand overhang. In some embodiments, the overhang comprises at least one 5'-5', 3'-3', 3'-2',2'-5', 2'-3' or 2'-2' intersugar linkage. In some embodiments, the single stranded overhang is linked via a 3'-3', 3'-2',2'-5', 2'-3' or 2'-2' intersugar linkage to the rest of the oligonucleotide.

In some embodiments, the unpaired nucleotide adjacent to the terminal nucleotide base pair on the end of the double-stranded region is a purine. In some embodiments, the single-stranded overhang has the sequence 5'-GCNN-3', wherein N is independently for each occurrence, A, G, C, U, dT, dU or absent. In some embodiment, the single-stranded overhang has the sequence 5'-N,N-3', wherein N is a modified or unmodified nucleotide described herein. In one preferred embodiment, the single-stranded overhang has the sequence 5'-dTdT-3' (dT=deoxythymidine). In another preferred embodiment, the single-stranded overhang has the sequence 5'-dTdT-3' (dT=deoxy thymidine) and the internucleotide linkage between the dTs is a non-phosphodiester intersugar linkage.

In some embodiments, the antisense strand of the double-stranded oligonucleotide has 1-10 nucleotide single-stranded overhang at each of the 3' end and the 5' end over the sense strand. In another embodiment, the sense strand of the double-stranded oligonucleotide has 1-10 nucleotide single-stranded overhang at each of the 3' end and the 5' end over the antisense strand.

Mismatches

The antisense strand of the double-stranded oligonucleotide can contain one or more mismatches to the target sequence. In a preferred embodiment, the antisense strand contains no more than 3 mismatches. If the antisense strand contains mismatches to a target sequence, it is preferable that the area of mismatch not be located in the center of the region of complementarity between the antisense strand and the target sequence. If the antisense strand contains mismatches to the target sequence, it is preferable that the mismatch be restricted to 5 nucleotides from either end, for example 5, 4, 3, 2, or 1 nucleotide from either the 5' or 3' end of the region of complementarity between the antisense strand and the target sequence. Methods known in the art can be used to determine whether a double-stranded oligonucleotide containing a mismatch to a target sequence is effective in inhibiting the expression of the target gene.

In some embodiment, the sense-strand comprises a mismatch to the antisense strand. In some embodiments, the sense strand comprises no more than 1, 2, 3, 4 or 5 mismatches to the antisense strand. In preferred embodiments, the sense strand comprises no more than 3 mismatches to the antisense strand.

In some embodiments, the sense-strand comprises a mismatch to the antisense strand and the mismatch is within the 5 nucleotides from the 3'-end of the sense strand, for example 5, 4, 3, 2, or 1 nucleotide from the end of the region of complementarity between the sense and the antisense strands.

In some embodiments, the sense-strand comprises a mismatch to the antisense strand and the mismatch is located in the target cleavage site region. In some embodiments, the sense strand comprises a nucleobase modification, e.g. an optionally substituted natural or non-natural nucleobase, a universal nucleobase, in the target cleavage site region.

The "target cleavage site" herein means the intersugar linkage in the target gene, e.g. target mRNA, or the sense strand that is cleaved by the RISC mechanism by utilizing the RNAi agent. And the "target cleavage site region" comprises at least one or at least two nucleotides on 3', 5' or both sides of the cleavage site. Preferably, the target cleavage site region comprises two nucleotides on both sides of the cleavage site. For the sense strand, the target cleavage site is the intersugar linkage in the sense strand that would get cleaved if the sense strand itself was the target to be cleaved by the RNAi mechanism. The target cleavage site can be determined using methods known in the art, for example the 5'-RACE assay as detailed in Soutschek et al., Nature (2004) 432, 173-178. Without wishing to be bound by theory, the cleavage site region for a conical double stranded RNAi agent comprising two 21-nucleotides long strands (wherein the strands form a double stranded region of 19 consecutive nucleotide base pairs having 2-nucleotide single stranded overhangs at the 3'-ends), the cleavage site region corresponds to positions 9-12 from the 5'-end of the sense strand.

In some embodiments, at least one of antisense strand or target sequence strand has at least one stretch of 1-5 single-stranded nucleotides in the region of complementarity between the antisense strand and the target sequence. In some embodiments, both the antisense strand and the target sequence strand have at least one stretch of 1-5 (e.g., 1, 2, 3, 4, or 5) single-stranded nucleotides in the region of complementarity between the antisense strand and the target sequence. When both strands have a stretch of 1-5 (e.g., 1, 2, 3, 4, or 5) single-stranded nucleotides in the double stranded region, such single-stranded nucleotides can be opposite to each other (e.g., a stretch of mismatches) or they can be located such that the second strand has no single-stranded nucleotides opposite to the single-stranded oligonucleotides of the first strand and vice versa (e.g., a single-stranded loop). Location of the single-stranded nucleotides is chosen as to minimize any deleterious effect on the gene silencing activity of the antisense strand. In some embodiments, the single-stranded nucleotides are present within 8 nucleotides from either end, for example 8, 7, 6, 5, 4, 3, or 2 nucleotide from either the 5' or 3' end of the region of complementarity between the antisense strand and the target sequence. In some embodiments, the antisense strand comprises the stretch of single-stranded nucleotides and which nucleotides are located in the target cleavage region.

Consideration of the efficacy of RNAi agents with mismatches in inhibiting expression of the target gene is important, especially if the particular region of complementarity in the target gene is known to have polymorphic sequence variation within the population.

Multi-Targeting

Sequences that are different from each other at 1, 2, 3, 4 or 5 positions can be targeted by a single RNAi agent, e.g., double-stranded or single-stranded RNAi agent. As used in this context, the phrase "different from each other" refers to the target sequences having different nucleotides at that position. In these cases the RNAi agent strand that is complementary to the target sequences comprises universal nucleobases at positions complementary to where the target sequences are different from each other. For example, the antisense strand of the double-stranded RNAi agent comprises universal nucleobases at positions complementary to where the sequences to be targeted do not match each other.

These multi targeting RNAi agents can be used to alter the expression of different transcripts/alleles of a single gene, different iso forms of a single gene, different splice variants of a single gene, different transcripts of more than one gene, wild-type and mutated forms of a gene, or homolog of a gene in different species.

The double-stranded RNAi agents of the invention can also target more than one RNA region by having each strand targeting a sequence or part thereof independently. For example, a double-stranded RNAi agent can include a first and second sequence that are sufficiently complementary to each other to hybridize. The first sequence can be complementary to a first target sequence and the second sequence can be complementary to a second target sequence. The first and second sequences of the RNAi agent can be on different RNA strands, and the mismatch between the first and second sequences can be less than 50%, 40%, 30%, 20%, 10%, 5%, or 1%. The first and second sequences of the RNAi agent can be on the same RNA strand, and in a related embodiment more than 50%, 60%, 70%, 80%, 90%, 95%, or 1% of the RNAi agent can be in bimolecular form. The first and second sequences of the RNAi agent can be fully complementary to each other.

The first target sequence can be a first target gene and the second target sequence can be a second target gene, or the first and second target sequences can be different regions of a single target gene. The first and second sequences can differ by at least 1 nucleotide.

The first and second target sequences can be transcripts encoded by first and second sequence variants, e.g., first and second alleles, of a gene. The sequence variants can be mutations, or polymorphisms, for example. The first target sequence can include a nucleotide substitution, insertion, or deletion relative to the second target sequence, or the second target sequence can be a mutant or variant of the first target sequence. The first and second target sequences can comprise viral or human genes. The first and second target sequences can also be on variant transcripts of an oncogene or include different mutations of a tumor suppressor gene transcript. In addition, the first and second target sequences can correspond to hot-spots for genetic variation.

Terminal End Thermal Stability

The double stranded oligonucleotides can be optimized for RNA interference by increasing the propensity of the duplex to disassociate or melt (decreasing the free energy of duplex association), in the region of the 5' end of the antisense strand This can be accomplished, e.g., by the inclusion of modifications or modified nucleosides which increase the propensity of the duplex to disassociate or melt in the region of the 5' end of the antisense strand. It can also be accomplished by inclusion of modifications or modified nucleosides or attachment of a ligand that increases the propensity of the duplex to disassociate of melt in the region of the 5' end of the antisense strand. While not wishing to be bound by theory, the effect can be due to promoting the effect of an enzyme such as helicase, for example, promoting the effect of the enzyme in the proximity of the 5' end of the antisense strand.

Modifications which increase the tendency of the 5' end of the antisense strand in the duplex to dissociate can be used alone or in combination with other modifications described herein, e.g., with modifications which decrease the tendency of the 3' end of the antisense in the duplex to dissociate. Likewise, modifications which decrease the tendency of the 3' end of the antisense in the duplex to dissociate can be used alone or in combination with other modifications described herein, e.g., with modifications which increase the tendency of the 5' end of the antisense in the duplex to dissociate.

Nucleic acid base pairs can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; I:C is preferred over G:C (I=inosine); mismatches, e.g., non-canonical or other than canonical pairings are preferred over canonical (A:T, A:U, G:C) pairings; pairings which include a universal base are preferred over canonical pairings.

It is preferred that pairings which decrease the propensity to form a duplex are used at 1 or more of the positions in the duplex at the 5' end of the antisense strand. The terminal pair (the most 5' pair in terms of the antisense strand), and the subsequent 4 base pairing positions (going in the 3' direction in terms of the antisense strand) in the duplex are preferred for placement of modifications to decrease the propensity to form a duplex. More preferred are placements in the terminal most pair and the subsequent 3, 2, or 1 base pairings. It is preferred that at least 1, and more preferably 2, 3, 4, or 5 of the base pairs from the 5'-end of antisense strand in the duplex be chosen independently from the group of: A:U, G:U, I:C, mismatched pairs, e.g., non-canonical or other than canonical pairings or pairings which include a universal base. In a preferred embodiment at least one, at least 2, or at least 3 base-pairs include a universal base.

Modifications or changes which promote dissociation are preferably made in the sense strand, though in some embodiments, such modifications/changes will be made in the antisense strand.

Nucleic acid base pairs can also be ranked on the basis of their propensity to promote stability and inhibit dissociation or melting (e.g., on the free energy of association or dissociation of a particular pairing, the simplest approach is to examine the pairs on an individual pair basis, though next neighbor or similar analysis can also be used). In terms of promoting duplex stability: G:C is preferred over A:U, Watson-Crick matches (A:T, A:U, G:C) are preferred over non-canonical or other than canonical pairings, analogs that increase stability are preferred over Watson-Crick matches (A:T, A:U, G:C), e.g. 2-amino-A:U is preferred over A:U, 2-thio U or 5-Me-thio-U:A, are preferred over U:A, G-clamp (an analog of C having 4 hydrogen bonds):G is preferred over C:G, guanadinium-G-clamp:G is preferred over C:G, psuedo uridine:A, is preferred over U:A, sugar modifications, e.g., 2' modifications, e.g., 2'F, ENA, or LNA, which enhance binding are preferred over non-modified moieties and can be present on one or both strands to enhance stability of the duplex.

It is preferred that pairings which increase the propensity to form a duplex are used at 1 or more of the positions in the duplex at the 3' end of the antisense strand. The terminal pair (the most 3' pair in terms of the antisense strand), and the subsequent 4 base pairing positions (going in the 5' direction in terms of the antisense strand) in the duplex are preferred for placement of modifications to increase the propensity to form a duplex. More preferred are placements in the terminal most pair and the subsequent 3, 2, or 1 base pairings. It is preferred that at least 1, and more preferably 2, 3, 4, or 5 of the pairs of the recited regions be chosen independently from the group of: G:C, a pair having an analog that increases stability over Watson-Crick matches (A:T, A:U, G:C), 2-amino-A:U, 2-thio U or 5 Me-thio-U:A, G-clamp (an analog of C having 4 hydrogen bonds):G, guanadinium-G-clamp:G, psuedo uridine:A, a base pair in which one or both subunits have a sugar modification, e.g., a 2' modification, e.g., 2'F, ENA, or LNA, which enhance binding. In some embodiments, at least one, at least, at least 2, or at least 3, of the base pairs promote duplex stability.

In a preferred embodiment, at least one, at least 2, or at least 3, of the base pairs are a pair in which one or both subunits has a sugar modification, e.g., a 2' modification, e.g., 2'-O-methyl, 2'-O-Me (2'-O-methyl), 2'-O-MOE (2'-O-methoxyethyl), 2'-F, 2'-O—CH$_2$-(4'-C) (LNA) and 2'-O—CH$_2$CH$_2$-(4'-C) (ENA), which enhance binding.

G-clamps and guanidinium G-clamps are discussed in the following references: Holmes and Gait, "The Synthesis of 2'-O-Methyl G-Clamp Containing Oligonucleotides and Their Inhibition of the HIV-1 Tat-TAR Interaction," Nucleosides, Nucleotides & Nucleic Acids, 22:1259-1262, 2003; Holmes et al., "Steric inhibition of human immunodeficiency virus type-1 Tat-dependent trans-activation in vitro and in cells by oligonucleotides containing 2'-O-methyl G-clamp ribonucleoside analogues," Nucleic Acids Research, 31:2759-2768, 2003; Wilds, et al., "Structural basis for recognition of guanosine by a synthetic tricyclic cytosine analogue: Guanidinium G-clamp," Helvetica Chimica Acta, 86:966-978, 2003; Rajeev, et al., "High-Affinity Peptide Nucleic Acid Oligomers Containing Tricyclic Cytosine Analogues," Organic Letters, 4:4395-4398, 2002; Ausin, et al., "Synthesis of Amino- and Guanidino-G-Clamp PNA Monomers," Organic Letters, 4:4073-4075, 2002; Maier et al., "Nuclease resistance of oligonucleotides containing the tricyclic cytosine analogues phenoxazine and 9-(2-aminoethoxy)-phenoxazine ("G-clamp") and origins of their nuclease resistance properties," Biochemistry, 41:1323-7, 2002; Flanagan, et al., "A cytosine analog that confers enhanced potency to antisense oligonucleotides," PNAS, US, 96:3513-8, 1999.

As is discussed above, an oligonucleotide can be modified to both decrease the stability of the antisense 5' end of the duplex and increase the stability of the antisense 3' end of the duplex. This can be effected by combining one or more of the stability decreasing modifications in the antisense 5' end of the duplex with one or more of the stability increasing modifications in the antisense 3' end of the duplex.

Nuclease Stability

In vivo applications of oligonucleotides is limited due to presence of nucleases in the serum and/or blood. Thus in certain instances it is preferable to modify the 3', 5' or both ends of an oligonucleotide to make the oligonucleotide resistant against exonucleases. In some embodiments, the oligonucleotide comprises a cap structure at 3' (3'-cap), 5' (5'-cap) or both ends. In some embodiments, oligonucleotide comprises a 3'-cap. In another embodiment, oligonucleotide comprises a 5'-cap. In yet another embodiment, oligonucleotide comprises both a 3' cap and a 5' cap. It is to be understood that when an oligonucleotide comprises both a 3' cap and a 5' cap, such caps can be same or they can be different.

As used herein, "cap structure" refers to chemical modifications, which have been incorporated at either terminus of oligonucleotide. See for example U.S. Pat. No. 5,998,203 and International Patent Publication WO03/70918, contents of which are herein incorporated in their entireties. Without wishing to be bound by theory, the monomers of the invention can be used as caps.

Exemplary 5'-caps include, but are not limited to, ligands, 5'-5'-inverted nucleotide, 5'-5'-inverted abasic nucleotide residue, 2'-5' linkage, 5'-amino, 5'-amino-alkyl phosphate, 5'-hexylphosphate, 5'-aminohexyl phosphate, bridging and/or non-bridging 5'-phosphoramidate, bridging and/or non-bridging 5'-phosphorothioate and/or 5'-phosphorodithioate, bridging or non bridging 5'-methylphosphonate, non-phosphodiester intersugar linkage between the end two nucleotides, 4',5'-methylene nucleotide, I-(beta-D-erythrofuranosyl) nucleotide, 4'-thio nucleotide, carbocyclic nucleotide, 1,5-anhydrohexitol nucleotide, L-nucleotides, alpha-nucleotides, modified nucleobase nucleotide, phosphorodithioate linkage, threo-pentofuranosyl nucleotide, acyclic nucleotide, acyclic 3,4-dihydroxybutyl nucleotide, acyclic 3,5-dihydroxypentyl nucleotide, 5'-mercapto nucleotide and 5'-1,4-butanediolphosphate.

Exemplary 3'-caps include, but are not limited to, ligands, 3'-3'-inverted nucleotide, 3'-3'-inverted abasic nucleotide residue, 3'-2'-inverted nucleotide moiety, 3'-2'-inverted abasic moiety, 2'-5'-linkage, 3'-amino, 3'-amino-alkyl phosphate, 3'-hexylphosphate, 3'-aminohexyl phosphate, bridging and/or non-bridging 3'-phosphoramidate, bridging and/or non-bridging 3'-phosphorothioate and/or 3'-phosphorodithioate, bridging or non bridging 3'-methylphosphonate, non-phosphodiester intersugar linkage between the end two nucleotides, I-(beta-D-erythrofuranosyl) nucleotide, 4'-thio nucleotide, carbocyclic nucleotide, 1,5-anhydrohexitol nucleotide, L-nucleotides, alpha-nucleotides, modified nucleobase nucleotide, phosphorodithioate linkage, threo-pentofuranosyl nucleotide, acyclic nucleotide, acyclic 3,4-dihydroxybutyl nucleotide, acyclic 3,5-dihydroxypentyl nucleotide, and 3'-1,4-butanediol phosphate. For more details see Beaucage and Iyer, 1993, Tetrahedron 49, 1925, incorporated by reference herein.

Other 3' and/or 5' caps amenable to the invention are described in U.S. Provisional Application No. 61/223,665, filed Jul. 7, 2009, contents of which are herein incorporated in their entirety.

In some embodiments, a double-stranded oligonucleotide comprises, on at least one end of the duplex region, a G-C base pair at the terminal position of the duplex region (e.g., the last base pair of the duplex) or the four consecutive base from the duplex region end comprise at least two G-C base pairs. In some embodiments, both ends of duplex region comprise a terminal G-C base pair and/or the first four consecutive base pairs from the terminal end comprise at least two G-C base pairs. In some embodiments, the first base-paired nucleotide next to single-stranded overhang is a C.

Off-Target Effects

As used herein, the term "off-target" and the phrase "off-target effects" refer to any instance in which an oligonucleotide against a given target causes an unintended affect by interacting either directly or indirectly with another mRNA sequence, a DNA sequence or a cellular protein or other moiety. For example, an "off-target effect" may occur when there is a simultaneous degradation of other transcripts due to partial homology or complementarity between that other transcript and the sense and/or antisense strand of a double-stranded RNAi agent.

In the RNA interference pathway, both strands of the double-stranded RNAi agent have the potential to enter the RISC complex and reduce the gene expression of corresponding complementary sequences. Without wishing to be bound by theory, one way an unwanted off-target effect happens ins when the sense strand enters the RISC complex and reduces the gene expression of a complementary sequence which is not the desired target of the RNAi agent.

A number of strategies can be applied to reduce the off-target effects due to sense strand mediated RNA interference. The sense strand can be chemically modified so that it can no longer act in the RISC mediated cleavage of a target sequence. Without wishing to be bound by theory, such modifications minimize off-target RNAi effects due to sense strand.

In some embodiments, the sense strand does not have a free terminal 5'-OH group. In another embodiment, the sense strand does not have a 5'-phosphate group. In some embodiments, the 5'-OH of sense strand is modified so that it can not be phosphorylated, e.g. with a cap moiety. In some embodiments, the cap moiety comprises L-sugar nucleotide, an alpha nucleotide, a hydroxy protecting group, an alkyl, a cycloalkyl or a heterocycle. In some embodiments, the linkage between the 5' end of sense strand and a conjugate is a non-phosphodiester intersugar linkage. In a preferred embodiment, the linkage between the 5' end of sense strand and a conjugate does not have a phosphate group.

In some embodiments, the sense strand comprises at least one modified nucleotide in the target cleavage site region. Preferably, the modification include modification at 2' position of ribose sugar or nucleobase modification.

In some embodiments, ends of double-stranded oligonucleotide can be modified so that the end corresponding to 5'end of sense strand has a higher thermal stability as compared to the end corresponding 3' end of sense strand, as described above in the Terminal end thermal stability section above. Without wishing to be bound by theory, this allows preferential incorporation of the antisense strand into the RISC complex and reduces off-target effects of sense strand.

Asymmetric Modifications

Modifications described herein can be used to asymmetrically modified a double-stranded oligonucleotide. An asymmetrically modified double-stranded oligonucleotide is one in which one strand has a modification which is not present on the other strand. As such, an asymmetrical modification is a modification found on one strand but not on the other strand. Any modification, e.g., any modification described herein, can be present as an asymmetrical modification. An asymmetrical modification can confer any of the desired properties associated with a modification, e.g., those properties discussed herein. For example, an asymmetrical modification can confer resistance to degradation, an alteration in half life; target the oligonucleotide to a particular target, e.g., to a particular tissue; modulate, e.g., increase or decrease, the affinity of a strand for its complement or target sequence; or hinder or promote modification of a terminal moiety, e.g., modification by a kinase or other enzymes involved in the RISC mechanism pathway. The designation of a modification as having one property does not mean that it has no other property, e.g., a modification referred to as one which promotes stabilization might also enhance targeting. Asymmetrical modifications can include those in which only one strand is modified as well as those in which both are modified.

When the two strands of double-stranded oligonucleotide are linked together, e.g. a hairpin or a dumbbell, the two strands of the double stranded region can be also be asymmetrically modified. For example, first strand of the double-stranded region comprises at least one asymmetric modification that is not present in the second strand of the double stranded region or vice versa.

While not wishing to be bound by theory or any particular mechanistic model, it is believed that asymmetrical modification allows a double-stranded RNAi agent to be optimized in view of the different or "asymmetrical" functions of the sense and antisense strands. For example, both strands can be modified to increase nuclease resistance, however, since some changes can inhibit RISC activity, these changes can be chosen for the sense stand. In addition, since some modifications, e.g., a ligand, can add large bulky groups that, e.g., can interfere with the cleavage activity of the RISC complex, such modifications are preferably placed on the sense strand. Thus, ligands, especially bulky ones (e.g. cholesterol), are preferentially added to the sense strand. The ligand can be present at either (or both) the 5' or 3' end of the sense strand of a RNAi agent.

Each strand can include one or more asymmetrical modifications. By way of example: one strand can include a first asymmetrical modification which confers a first property on the oligonucleotide and the other strand can have a second asymmetrical modification which confers a second property on the oligonucleotide. For example, one strand, e.g., the sense strand can have a modification which targets the oligonucleotide to a tissue, and the other strand, e.g., the antisense strand, has a modification which promotes hybridization with the target gene sequence.

In some embodiments both strands can be modified to optimize the same property, e.g., to increase resistance to nucleolytic degradation, but different modifications are chosen for the sense and the antisense strands, because the modifications affect other properties as well.

Multiple asymmetric modifications can be introduced into either or both of the sense and antisense strand. A strand can have at least 1, 2, 3, 4, 5, 6, 7, 8, or more modifications and all or substantially all of the monomers, e.g., nucleotides of a strand can be asymmetrically modified.

In some embodiments, the asymmetric modifications are chosen so that only one of the two strands of double-stranded RNAi agent is effective in inducing RNAi Inhibiting the induction of RNAi by one strand can reduce the off target effects due to cleavage of a target sequence by that strand.

In preferred embodiments asymmetrical modifications which result in one or more of the following are used: modifications of the 5' end of the sense strand which inhibit kinase activation of the sense strand, including, e.g., attachments of ligands or the use modifications which protect against 5' exonucleolytic degradation; or modifications of either strand, but preferably the sense strand, which enhance binding between 5'-end of the sense and 3'-end of the antisense strand and thereby promote a "tight" structure at this end of the molecule.

The end region of the RNAi agent defined by the 3' end of the sense strand and the 5' end of the antisense strand is also important for function. This region can include the terminal 2, 3, or 4 paired nucleotides and any 3' overhang. Preferred embodiments include asymmetrical modifications of either strand, but preferably the sense strand, which decrease binding between 3'-end of the sense and 5'-end of the antisense strand and thereby promote an "open" structure at this end of the molecule. Such modifications include placing conjugates which target the molecule or modifications which promote nuclease resistance on the sense strand in this region. Modification of the antisense strand which inhibit kinase activation are avoided in preferred embodiments.

Particularly preferred asymmetric modification are modifications of 2'-OH of ribose sugar and modification (or replacement) of intersugar phosphodiester linkage. Other preferred asymmetric modifications include conjugation of ligands. Each strand can be conjugated with ligands that are different between the two strands.

In some embodiments, one strand has an asymmetrical 2'-modificaiton, e.g., a 2'-O-alkyl modification, and the other strand has an asymmetrical modification of the intersugar phosphodiester linkage. In some embodiments, one strand has an asymmetrical 2'-modification, e.g., a 2'-O-alkyl modification, and the other strand also has an asymmetrical 2'-modification that is different from the first strand's asymmetrical 2'-modification, e.g., 2'-fluoro modification.

In some embodiments, one strand is asymmetrically modified with 2'-O-alkyl, e.g. 2'-OMe modification and the second strand is asymmetrically modified with 2'-fluoro modification.

In some embodiments, one strand is asymmetrically modified with 2'-O-alkyl, e.g. 2'-OMe modification and the second strand is asymmetrically modified with intersugar linkage modification, e.g. a phosphorothioate modification.

In some embodiments, one strand is asymmetrically modified with 2'-fluoro modification and the second strand is asymmetrically modified with intersugar linkage modification, e.g. a phosphorothioate modification.

It is preferable to have RNAi agents wherein there are multiple 2'-O-alkyl, e.g., 2'-OMe modifications on the sense strand and multiple 2'-fluoro and/or multiple modified intersugar linkages on the antisense strand.

Modifications, e.g., those described herein, which modulate, e.g., increase or decrease, the affinity of a strand for its compliment or target, can be provided as asymmetrical modifications.

Chimeric Oligonucleotides

The present invention also includes oligonucleotides which are chimeric oligonucleotides. "Chimeric" oligonucleotides or "chimeras," in the context of this invention, are oligonucleotide which contain two or more chemically distinct regions, each made up of at least one monomer unit, i.e., a modified or unmodified nucleotide in the case of an oligonucleotide. Chimeric oligonucleotides can be described as having a particular motif. In some embodiments, the motifs include, but are not limited to, an alternating motif, a gapped motif, a hemimer motif, a uniformly fully modified motif and a positionally modified motif. As used herein, the phrase "chemically distinct region" refers to an oligonucleotide region which is different from other regions by having a modification that is not present elsewhere in the oligonucleotide or by not having a modification that is present elsewhere in the oligonucleotide. An oligonucleotide can comprise two or more chemically distinct regions. As used herein, a region that comprises no modifications is also considered chemically distinct.

A chemically distinct region can be repeated within an oligonucleotide. Thus, a pattern of chemically distinct regions in an oligonucleotide can be realized such that a first chemically distinct region is followed by one or more second chemically distinct regions. This sequence of chemically distinct regions can be repeated one or more times. Preferably, the sequence is repeated more than one time. Both strands of a double-stranded oligonucleotides can comprise these sequences. Each chemically distinct region can actually comprise as little as a single nucleotide. In some embodiments, each chemically distinct region comprises 1, 2, 3, 4, 5, 6, 7, 8, 9, 10, 11, 12, 13, 14, 15, 16, 17 or 18 nucleotides.

In some embodiments, alternating nucleotides comprise the same modification, e.g. all the odd number nucleotides in a strand have the same modification and/or all the even number nucleotides in a strand have the similar modification to the first strand. In some embodiments, all the odd number nucleotides in an oligonucleotide have the same modification and all the even numbered nucleotides have a modification that is not present in the odd number nucleotides and vice versa.

When both strands of a double-stranded oligonucleotide comprise the alternating modification patterns, nucleotides of one strand can be complementary in position to nucleotides of the second strand which are similarly modified. In an alternative embodiment, there is a phase shift between the patterns of modifications of the first strand, respectively, relative to the pattern of similar modifications of the second strand. Preferably, the shift is such that the similarly modified nucleotides of the first strand and second strand are not in complementary position to each other.

In some embodiments, the first strand has an alternating modification pattern wherein alternating nucleotides comprise a 2'-modification, e.g., 2'-O-Methyl modification. In some embodiments, the first strand comprises an alternating 2'-O-Methyl modification and the second strand comprises an alternating 2'-fluoro modification. In other embodiments, both strands of a double-stranded oligonucleotide comprise alternating 2'-O-methyl modifications.

When both strands of a double-stranded oligonucleotide comprise alternating 2'-O-methyl modifications, such 2'-modified nucleotides can be in complementary position in the duplex region. Alternatively, such 2'-modified nucleotides may not be in complementary positions in the duplex region.

In some embodiments, the oligonucleotide comprises two chemically distinct regions, wherein each region is 1-10 nucleotides in length.

In other embodiments, the oligonucleotide comprises three chemically distinct region. The middle region is about 5-15, (e.g., 5, 6, 7, 8, 9, 10, 11, 12, 13, 14 or 15) nucleotide in length and each flanking or wing region is independently 1-10 (e.g., 1, 2, 3, 4, 5, 6, 7, 8, 9 or 10) nucleotides in length. All three regions can have different modifications or the wing regions can be similarly modified to each other. In some embodiments, the wing regions are of equal length, e.g. 1, 2, 3, 4, 5, 6, 7, 8, 9 or 10 nucleotides long.

As used herein the term "alternating motif" refers to a an oligonucleotide comprising a contiguous sequence of linked monomer subunits wherein the monomer subunits have two different types of sugar groups that alternate for essentially the entire sequence of the oligonucleotide. Oligonucleotides having an alternating motif can be described by the formula: 5'-A(-L-B-L-A)n(-L-B)nn-3' where A and B are monomelic subunits that have different sugar groups, each L is an internucleoside linking group, n is from about 4 to about 12 and nn is 0 or 1. This permits alternating oligonucleotides from about 9 to about 26 monomer subunits in length. This length range is not meant to be limiting as longer and shorter oligonucleotides are also amenable to the present invention. In one embodiment, one of A and B is a 2'-modified nucleoside as provided herein.

As used herein, "type of modification" in reference to a nucleoside or a nucleoside of a "type" refers to the modification of a nucleoside and includes modified and unmodified nucleosides. Accordingly, unless otherwise indicated, a "nucleoside having a modification of a first type" may be an unmodified nucleoside.

As used herein, "type region" refers to a portion of an oligomeric compound wherein the nucleosides and internucleoside linkages within the region all comprise the same type of modifications; and the nucleosides and/or the internucleoside linkages of any neighboring portions include at least one different type of modification. As used herein the term "uniformly fully modified motif" refers to an oligonucleotide comprising a contiguous sequence of linked monomer subunits that each have the same type of sugar group. In one embodiment, the uniformly fully modified motif includes a contiguous sequence of nucleosides of the invention. In one embodiment, one or both of the 3' and 5'-ends of the contiguous sequence of the nucleosides provided herein, comprise terminal groups such as one or more unmodified nucleosides.

As used herein the term "hemimer motif" refers to an oligonucleotide having a short contiguous sequence of monomer subunits having one type of sugar group located at the 5' or the 3' end wherein the remainder of the monomer subunits have a different type of sugar group. In general, a hemimer is an oligomeric compound of uniform sugar groups further comprising a short region (1, 2, 3, 4 or about 5 monomelic subunits) having uniform but different sugar groups and located on either the 3' or the 5' end of the oligomeric compound. In one embodiment, the hemimer motif comprises a contiguous sequence of from about 10 to about 28 monomer subunits of one type with from 1 to 5 or from 2 to about 5 monomer subunits of a second type located at one of the termini. In one embodiment, a hemimer is a contiguous sequence of from about 8 to about 20 β-D-2'-deoxyribonucleosides having from 1-12 contiguous nucleosides of the invention located at one of the termini. In one embodiment, a hemimer is a contiguous sequence of from about 8 to about 20 β-D-2'-deoxyribonucleosides having from 1-5 contiguous nucleosides of the invention located at one of the termini. In one embodiment, a hemimer is a contiguous sequence of from about 12 to about 18 β-D-2'-deoxyribo-nucleosides having from 1-3 contiguous nucleosides of the invention located at one of the termini. In one embodiment, a hemimer is a contiguous sequence of from about 10 to about 14 β-D-2'-deoxyribonucleosides having from 1-3 contiguous nucleosides of the invention located at one of the termini.

As used herein the term "blockmer motif" refers to an oligonucleotide comprising an otherwise contiguous sequence of monomer subunits wherein the sugar groups of each monomer subunit is the same except for an interrupting internal block of contiguous monomer subunits having a different type of sugar group. A blockmer overlaps somewhat with a gapmer in the definition but typically only the monomer subunits in the block have non-naturally occurring sugar groups in a blockmer and only the monomer subunits in the external regions have non-naturally occurring sugar groups in a gapmer with the remainder of the monomer subunits in the blockmer or gapmer being β-D-2'-deoxyribonucleosides or β-D-ribonucleosides. In one embodiment, blockmer oligonucleotides are provided herein wherein all of the monomer subunits comprise non-naturally occurring sugar groups.

As used herein the term "positionally modified motif" is meant to include an otherwise contiguous sequence of monomer subunits having one type of sugar group that is interrupted with two or more regions of from 1 to about 5 contiguous monomer subunits having another type of sugar group. Each of the two or more regions of from 1 to about 5 contiguous monomer subunits are independently uniformly modified with respect to the type of sugar group. In one embodiment, each of the two or more regions have the same type of sugar group. In one embodiment, each of the two or more regions have a different type of sugar group. In one embodiment, positionally modified oligonucleotides are provided comprising a sequence of from 8 to 20 β-D-2'-deoxyribonucleosides that further includes two or three regions of from 2 to about 5 contiguous nucleosides of the invention. Positionally modified oligonucleotides are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein the sugar group of each monomer subunit within a particular region is the same. When the sugar groups of the external regions are the same the gapmer is a symmetric gapmer and when the sugar group used in the 5'-external region is different from the sugar group used in the 3'-external region, the gapmer is an asymmetric gapmer. In one embodiment, the external regions are small (each independently 1, 2, 3, 4 or about 5 monomer subunits) and the monomer subunits comprise non-naturally occurring sugar groups with the internal region comprising β-D-2'-deoxyribonucleosides. In one embodiment, the external regions each, independently, comprise from 1 to about 5 monomer subunits having non-naturally occurring sugar groups and the internal region comprises from 6 to 18 unmodified nucleosides. The internal region or the gap generally comprises β-D-2'-deoxyribo-nucleosides but can comprise non-naturally occurring sugar groups.

In one embodiment, the gapped oligonucleotides comprise an internal region of β-D-2'-deoxyribonucleosides with one of the external regions comprising nucleosides of the invention. In one embodiment, the gapped oligonucleotide comprise an internal region of β-D-2'-deoxyribonucleosides with both of the external regions comprising nucleosides of the invention. In one embodiment, the gapped oligonucleotide comprise an internal region of β-D-2'-deoxyribonucleosides with both of the external regions comprising nucleosides of the invention. In one embodiment, gapped oligonucleotides are provided herein wherein all of the monomer subunits comprise non-naturally occurring sugar groups. In one embodiment, gapped oligonucleotides are provided comprising one or two nucleosides of the invention at the 5'-end, two or three nucleosides of the invention at the 3'-end and an internal region of from 10 to 16 β-D-2'-deoxyribonucleosides. In one embodiment, gapped oligonucleotides are provided comprising one nucleoside of the invention at the 5'-end, two nucleosides of the invention at the 3'-end and an internal region of from 10 to 16 β-D-2'-deoxyribonucleosides. In one embodiment, gapped oligonucleotides are provided comprising two nucleosides of the invention at the 5'-end, two nucleosides of the invention at the 3'-end and an internal region of from 10 to 14 β-D-2'-deoxyribonucleosides. In one embodiment, gapped oligonucleotides are provided that are from about 10 to about 21 monomer subunits in length. In one embodiment, gapped oligonucleotides are provided that are from about 12 to about 16 monomer subunits in length. In one embodiment, gapped oligonucleotides are provided that are from about 12 to about 14 monomer subunits in length.

Certain 5'-Terminal Nucleosides

In certain embodiments, the 5'-terminal nucleoside of an oligonucleotides of the present invention comprises a phosphorous moiety at the 5'-end. In certain embodiments the 5'-terminal nucleoside comprises a 2'-modification. In certain such embodiments, the 2'-modification of the 5'-terminal nucleoside is a cationic modification. In certain embodiments, the 5'-terminal nucleoside comprises a 5'-modification. In certain embodiments, the 5'-terminal nucleoside comprises a 2'-modification and a 5'-modification. In certain embodiments, the 5'-terminal nucleoside is a monomer of formula (I), (II) or (III).

In certain embodiments, the 5'-terminal nucleoside is a 5'-stabilizing nucleoside. In certain embodiments, the modifications of the 5'-terminal nucleoside stabilize the 5'-phosphate. In certain embodiments, oligonucleotides comprising modifications of the 5'-terminal nucleoside are resistant to exonucleases. In certain embodiments, oligonucleotides comprising modifications of the 5'-terminal nucleoside have improved antisense properties. In certain such embodiments, oligonucleotides comprising modifications of the 5'-terminal nucleoside have improved association with members of the RISC pathway. In certain embodiments, oligonucleotides comprising modifications of the 5'-terminal nucleoside have improved affinity for Ago2.

In certain embodiments, the 5' terminal nucleoside is attached to a plurality of nucleosides by a modified linkage. In certain such embodiments, the 5' terminal nucleoside is a plurality of nucleosides by a phosphorothioate linkage.

Certain Alternating Regions

In certain embodiments, oligonucleotides of the present invention comprise one or more regions of alternating modifications. In certain embodiments, oligonucleotides comprise one or more regions of alternating nucleoside modifications. In certain embodiments, oligonucleotides comprise one or more regions of alternating linkage modifications. In certain embodiments, oligonucleotides comprise one or more regions of alternating nucleoside and linkage modifications.

In certain embodiments, oligonucleotides of the present invention comprise one or more regions of alternating 2'-F modified nucleosides and 2'-OMe modified nucleosides. In certain such embodiments, such regions of alternating 2'F modified and 2'OMe modified nucleosides also comprise alternating linkages. In certain such embodiments, the linkages at the 3' end of the 2'-F modified nucleosides are phosphorothioate linkages. In certain such embodiments, the linkages at the 3' end of the 2'OMe nucleosides are phosphodiester linkages. In certain embodiments, such alternating regions are:

(2'-F)—(PS)-(2'-OMe)-(PO)

In certain embodiments, oligomeric compounds comprise 2, 3, 4, 5, 6, 7, 8, 9, 10, or 11 such alternating regions. Such regions may be contiguous or may be interrupted by differently modified nucleosides or linkages.

In certain embodiments, one or more alternating regions in an alternating motif include more than a single nucleoside of a type. For example, oligomeric compounds of the present invention may include one or more regions of any of the following nucleoside motifs:

AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, BNA, DNA, MOE, and monomer of formula (I), (II) or (III).

In certain embodiments, A is DNA. In certain embodiments, B is 4'-CH$_2$O-2'-BNA. In certain embodiments, A is DNA and B is 4'-CH$_2$O-2'-BNA. In certain embodiments A is 4'-CH$_2$O-2'-BNA, B is DNA. In certain embodiments A is 4'-CH$_2$O-2'-BNA and B is DNA. In certain embodiments, A is 2'-F. In certain embodiments, B is 2'-OMe. In certain embodiments, A is 2'-F and B is 2'-OMe. In certain embodiments, A is 2'-OMe. In certain embodiments, B is 2'-F. In certain embodiments, A is 2'-OMe and B is 2'-F. In certain embodiments, A is DNA and B is 2'-OMe. In certain embodiments, A is 2'-OMe and B is DNA.

In certain embodiments, oligomeric compounds having such an alternating motif also comprise a 5' terminal nucleoside comprising a phosphate stabilizing modification. In certain embodiments, oligomeric compounds having such an alternating motif also comprise a 5' terminal nucleoside comprising a 2'-cationic modification. In certain embodiments, oligomeric compounds having such an alternating motif also comprise a 5' terminal monomer of formula (I), (II) or (III).

Two-Two-Three Motifs

In certain embodiments, oligonucleotides of the present invention comprise a region having a 2-2-3 motif. Such regions comprises the following motif:

5'-(E)$_w$-(A)-2-(B)$_x$-(A)$_2$-(C)$_y$-(A)-3-(D)$_z$ wherein: A is a first type of modified nucleoside;

B, C, D, and E are nucleosides that are differently modified than A, however, B, C, D, and E may have the same or different modifications as one another;

w and z are from 0 to 15;

x and y are from 1 to 15.

In certain embodiments, A is a 2'-OMe modified nucleoside. In certain embodiments, B, C, D, and E are all 2'-F modified nucleosides. In certain embodiments, A is a 2'-OMe modified nucleoside and B, C, D, and E are all 2'-F modified nucleosides.

In certain embodiments, the linkages of a 2-2-3 motif are all modified linkages. In certain embodiments, the linkages are all phosphorothioate linkages. In certain embodiments, the linkages at the 3'-end of each modification of the first type are phosphodiester.

In certain embodiments, Z is 0. In such embodiments, the region of three nucleosides of the first type are at the 3'-end of the oligonucleotide. In certain embodiments, such region is at the 3'-end of the oligomeric compound, with no additional groups attached to the 3' end of the region of three nucleosides of the first type. In certain embodiments, an oligomeric compound comprising an oligonucleotide where Z is 0, may comprise a terminal group attached to the 3'-terminal nucleoside. Such terminal groups may include additional nucleosides. Such additional nucleosides are typically non-hybridizing nucleosides.

In certain embodiments, Z is 1-3. In certain embodiments, Z is 2. In certain embodiments, the nucleosides of Z are 2'-MOE nucleosides. In certain embodiments, Z represents non-hybridizing nucleosides. To avoid confusion, it is noted that such non-hybridizing nucleosides might also be described as a 3'-terminal group with Z=0.

Combination Motifs

It is to be understood, that certain of the above described motifs and modifications may be combined. Since a motif may comprises only a few nucleosides, a particular oligonucleotide may comprise two or more motifs. By way of non-limiting example, in certain embodiments, oligomeric compounds may have nucleoside motifs as described in the table below. In the table below, the term "None" indicates that a particular feature is not present in the oligonucleotide. For example, "None" in the column labeled "5' motif/modification" indicates that the 5' end of the oligonucleotide comprises the first nucleoside of the central motif

| 5' motif/modification | Central Motif | 3'-motif |
| --- | --- | --- |
| Formula (I), (II) or (III) | Alternating | 2 MOE nucleosides |
| Formula (I), (II) or (III) | 2-2-3 motif | 2 MOE nucleosides |
| Formula (I), (II) or (III) | Uniform | 2 MOE nucleosides |
| Formula (I), (II) or (III) | Alternating | 2 MOE nucleosides |
| Formula (I), (II) or (III) | Alternating | 2 MOE A's |
| Formula (I), (II) or (III) | 2-2-3 motif | 2 MOE A's |
| Formula (I), (II) or (III) | Uniform | 2 MOE A's |
| Formula (I), (II) or (III) | Alternating | 2 MOE U's |
| Formula (I), (II) or (III) | 2-2-3 motif | 2 MOE U's |
| Formula (I), (II) or (III) | Uniform | 2 MOE U's |
| None | Alternating | 2 MOE nucleosides |
| None | 2-2-3 motif | 2 MOE nucleosides |
| None | Uniform | 2 MOE nucleosides |

Oligomeric compounds having any of the various nucleoside motifs described herein, may have any linkage motif. For example, the oligomeric compounds, including but not limited to those described in the above table, may have a linkage motif selected from non-limiting the table below:

| 5' most linkage | Central region | 3'-region |
| --- | --- | --- |
| PS | Alternating PO/PS | 6 PS |
| PS | Alternating PO/PS | 7 PS |
| PS | Alternating PO/PS | 8 PS |

As is apparent from the above, non-limiting tables, the lengths of the regions defined by a nucleoside motif and that of a linkage motif need not be the same. For example, the 3' region in the nucleoside motif table above is 2 nucleosides, while the 3'-region of the linkage motif table above is 6-8 nucleosides. Combining the tables results in an oligonucleotide having two 3'-terminal MOE nucleosides and six to eight 3'-terminal phosphorothioate linkages (so some of the linkages in the central region of the nucleoside motif are phosphorothioate as well). To further illustrate, and not to limit in any way, nucleoside motifs and sequence motifs are combined to show five non-limiting examples in the table below. The first column of the table lists nucleosides and linkages by position from N1 (the first nucleoside at the 5'-end) to N20 (the 20$^{th}$ position from the 5'-end). In certain embodiments, oligonucleotides of the present invention are longer than 20 nucleosides (the table is merely exemplary). Certain positions in the table recite the nucleoside or linkage "none" indicating that the oligonucleotide has no nucleoside at that position.

| Pos | A | B | C | D | E | F |
|---|---|---|---|---|---|---|
| N1 | Formula (I), (II) or (III) | Formula (I), (II) or (III) | Formula (I), (II) or (III) | Formula (I), (II) or (III) | Formula (I), (II) or (III) | 2'-F |
| L1 | PS | PS | PS | PS | PO | PO |
| N2 | 2'-F | 2'-F | 2'-F | 2'-OMe | MOE | 2'-OMe |
| L2 | PS | PS | PS | PO | PS | PO |
| N3 | 2'-OMe | 2'-F | 2'-F | 2'-F | 2'-F | 2'-F |
| L3 | PO | PS | PS | PS | PS | PS |
| N4 | 2'-F | 2'-F | 2'-F | 2'-OMe | 2'-F | 2'-OMe |
| L4 | PS | PS | PS | PO | PS | PO |
| N5 | 2'-OMe | 2'-F | 2'-F | 2'-F | 2'-OMe | 2'-F |
| L5 | PO | PS | PS | PS | PO | PS |
| N6 | 2'-F | 2'-OMe | 2'-F | 2'-OMe | 2'-OMe | 2'-OMe |
| L6 | PS | PO | PS | PO | PO | PO |
| N7 | 2'-OMe | 2'-OMe | 2'-F | 2'-F | 2'-OMe | 2'-F |
| L7 | PO | PO | PS | PS | PO | PS |
| N8 | 2'-F | 2'-F | 2'-F | 2'-OMe | 2'-F | 2'-OMe |
| L8 | PS | PS | PS | PO | PS | PO |
| N9 | 2'-OMe | 2'-F | 2'-F | 2'-F | 2'-F | 2'-F |
| L9 | PO | PS | PS | PS | PS | PS |
| N10 | 2'-F | 2'-OMe | 2'-F | 2'-OMe | 2'-OMe | 2'-OMe |
| L10 | PS | PO | PS | PO | PO | PO |
| N11 | 2'-OMe | 2'-OMe | 2'-F | 2'-F | 2'OMe | 2'-F |
| L11 | PO | PO | PS | PS | PO | PS |
| N12 | 2'-F | 2'-F | 2'-F | 2'-F | 2'-F | 2'-OMe |
| L12 | PS | PS | PS | PO | PS | PO |
| N13 | 2'-OMe | 2'-F | 2'-F | 2'-F | 2'-F | 2'-F |
| L13 | PO | PS | PS | PS | PS | PS |
| N14 | 2'-F | 2'-OMe | 2'-F | 2'-F | 2'-F | 2'-F |
| L14 | PS | PS | PS | PS | PS | PS |
| N15 | 2'-OMe | 2'OMe | 2'-F | 2'-F | 2'-MOE | 2'-F |
| L15 | PS | PS | PS | PS | PS | PS |
| N16 | 2'-F | 2'OMe | 2'-F | 2'-F | 2'-MOE | 2'-F |
| L16 | PS | PS | PS | PS | PS | PS |
| N17 | 2'-OMe | 2'-MOE U | 2'-F | 2'-F | 2'-MOE | 2'-F |
| L17 | PS | PS | PS | PS | None | PS |
| N18 | 2'-F | 2'-MOE U | 2'-F | 2'-OMe | None | MOE A |
| L18 | PS | None | PS | PS | None | PS |
| N19 | 2'-MOE U | None | 2'-MOE U | 2'-MOE A | None | MOE U |
| L19 | PS | None | PS | PS | None | None |
| N20 | 2'-MOE U | None | 2'-MOE U | 2'-MOE A | None | None |

In the above, non-limiting examples:

Column A represent an oligomeric compound consisting of 20 linked nucleosides, wherein the oligomeric compound comprises: a modified 5'-terminal nucleoside of Formula (I), (II) or (III); a region of alternating nucleosides; a region of alternating linkages; two 3'-terminal MOE nucleosides, each of which comprises a uracil base; and a region of six phosphorothioate linkages at the 3'-end.

Column B represents an oligomeric compound consisting of 18 linked nucleosides, wherein the oligomeric compound comprises: a modified 5'-terminal nucleoside of Formula (I), (II) or (III); a 2-2-3 motif wherein the modified nucleoside of the 2-2-3 motif are 2'O-Me and the remaining nucleosides are all 2'-F; two 3'-terminal MOE nucleosides, each of which comprises a uracil base; and a region of six phosphorothioate linkages at the 3'-end.

Column C represents an oligomeric compound consisting of 20 linked nucleosides, wherein the oligomeric compound comprises: a modified 5'-terminal nucleoside of Formula (I), (II) or (III); a region of uniformly modified 2'-F nucleosides; two 3'-terminal MOE nucleosides, each of which comprises a uracil base; and wherein each internucleoside linkage is a phosphorothioate linkage.

Column D represents an oligomeric compound consisting of 20 linked nucleosides, wherein the oligomeric compound comprises: a modified 5'-terminal nucleoside of Formula (I), (II) or (III); a region of alternating 2'-OMe/2'-F nucleosides; a region of uniform 2'F nucleosides; a region of alternating phosphorothioate/phosphodiester linkages; two 3'-terminal MOE nucleosides, each of which comprises an adenine base; and a region of six phosphorothioate linkages at the 3'-end.

Column E represents an oligomeric compound consisting of 17 linked nucleosides, wherein the oligomeric compound comprises: a modified 5'-terminal nucleoside of Formula (I), (II) or (III); a 2-2-3 motif wherein the modified nucleoside of the 2-2-3 motif are 2'F and the remaining nucleosides are all 2'-OMe; three 3'-terminal MOE nucleosides.

Column F represents an oligomeric compound consisting of 18 linked nucleosides, wherein the oligomeric compound comprises: a region of alternating 2'-OMe/2'-F nucleosides; a region of uniform 2'F nucleosides; a region of alternating phosphorothioate/phosphodiester linkages; two 3'-terminal MOE nucleosides, one of which comprises a uracil base and the other of which comprises an adenine base; and a region of six phosphorothioate linkages at the 3'-end.

The above examples are provided solely to illustrate how the described motifs may be used in combination and are not intended to limit the invention to the particular combinations or the particular modifications used in illustrating the combinations. Further, specific examples herein, including, but not limited to those in the above table are intended to encompass more generic embodiments. For example, column A in the above table exemplifies a region of alternating 2'-OMe and 2'-F nucleosides. Thus, that same disclosure also exemplifies a region of alternating different 2'-modifications. It also exemplifies a region of alternating 2'-O-alkyl and 2'-halogen nucleosides. It also exemplifies a region of alternating differently modified nucleosides. All of the examples throughout this specification contemplate such generic interpretation.

It is also noted that the lengths of oligomeric compounds, such as those exemplified in the above tables, can be easily manipulated by lengthening or shortening one or more of the described regions, without disrupting the motif.

In some embodiments, oligonucleotide comprises two or more chemically distinct regions and has a structure as described in International Application No. PCT/US09/038, 433, filed Mar. 26, 2009, contents of which are herein incorporated in their entirety.

Ligands

A wide variety of entities, e.g., ligands, can be coupled to the oligonucleotides described herein. Ligands can include naturally occurring molecules, or recombinant or synthetic molecules. Exemplary ligands include, but are not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG, e.g., PEG-2K, PEG-5K, PEG-10K, PEG-12K, PEG-15K, PEG-20K, PEG-40K), MPEG, [MPEG]$_2$, polyvinyl alcohol (PVA), polyurethane, poly(2-ethylacrylic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g., steroids, bile acids, cholesterol, cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent (e.g., a helical cell-permeation agent).

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic (also referred to herein as an oligopeptidomimetic) is a molecule capable of folding into a defined three-dimensional structure similar to a natural peptide. The peptide or peptidomimetic ligand can be about 5-50 amino acids long, e.g., about 5, 10, 15, 20, 25, 30, 35, 40, 45, or 50 amino acids long.

Exemplary amphipathic peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins.

As used herein, the term "endosomolytic ligand" refers to molecules having endosomolytic properties. Endosomolytic ligands promote the lysis of and/or transport of the composition of the invention, or its components, from the cellular compartments such as the endosome, lysosome, endoplasmic reticulum (ER), golgi apparatus, microtubule, peroxisome, or other vesicular bodies within the cell, to the cytoplasm of the cell. Some exemplary endosomolytic ligands include, but are not limited to, imidazoles, poly or oligoimidazoles, linear or branched polyethyleneimines (PEIs), linear and branched polyamines, e.g. spermine, cationic linear and branched polyamines, polycarboxylates, polycations, masked oligo or poly cations or anions, acetals, polyacetals, ketals/polyketals, orthoesters, linear or branched polymers with masked or unmasked cationic or anionic charges, dendrimers with masked or unmasked cationic or anionic charges, polyanionic peptides, polyanionic peptidomimetics, pH-sensitive peptides, natural and synthetic fusogenic lipids, natural and synthetic cationic lipids.

Exemplary endosomolytic/fusogenic peptides include, but are not limited to,

```
                                                  SEQ ID NO: 9
AALEALAEALEALAEALEALAEAAAAGGC (GALA);,

SEQ ID NO: 10
AALAEALAEALAEALAEALAEALAAAAGGC (EALA);,

SEQ ID NO: 11
ALEALAEALEALAEA;,

SEQ ID NO: 12
GLFEAIEGFIENGWEGMIWDYG (INF-7);,

SEQ ID NO: 13
GLFGAIAGFIENGWEGMIDGWYG (Inf HA-2);,

SEQ ID NO: 14
GLFEAIEGFIENGWEGMIDGWYGCGLFEAIEGFIENGWEGMIDGWYGC (diINF-7);,

SEQ ID NO: 15
GLFEAIEGFIENGWEGMIDGGCGLFEAIEGFIENGWEGMIDGGC (diINF-3);,

SEQ ID NO: 16
GLFGALAEALAEALAEHLAEALAEALEALAAGGSC (GLF);,

SEQ ID NO: 17
GLFEAIEGFIENGWEGLAEALAEALEALAAGGSC (GALA-INF3);,

SEQ ID NO: 18
GLF EAI EGFI ENGW EGnI DG K GLF EAI EGFI ENGW EGnI

DG (INF-5 n is norleucine);,

SEQ ID NO: 19
LFEALLELLESLWELLLEA (JTS-1);,

SEQ ID NO: 20
GLFKALLKLLKSLWKLLLKA (ppTG1);,

SEQ ID NO: 21
GLFRALLRLLRSLWRLLLRA (ppTG20);,

SEQ ID NO: 22
WEAKLAKALAKALAKHLAKALAKALKACEA (KALA);,

SEQ ID NO: 23
GLFFEAIAEFIEGGWEGLIEGC (HA);,

SEQ ID NO: 24
GIGAVLKVLTTGLPALISWIKRKRQQ (Melittin);,

SEQ ID NO: 25
H5WYG;,
and
                                                  SEQ ID NO: 26
CHK6HC.,
```

Without wishing to be bound by theory, fusogenic lipids fuse with and consequently destabilize a membrane. Fusogenic lipids usually have small head groups and unsaturated acyl chains. Exemplary fusogenic lipids include, but are not limited to, 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6,9,28,31-tetraen-19-ol (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl)ethanamine (also referred to as XTC herein).

Synthetic polymers with endosomolytic activity amenable to the present invention are described in U.S. Pat. App. Pub. Nos. 2009/0048410; 2009/0023890; 2008/0287630; 2008/0287628; 2008/0281044; 2008/0281041; 2008/0269450; 2007/0105804; 20070036865; and 2004/0198687, contents of which are hereby incorporated by reference in their entirety.

Exemplary cell permeation peptides include, but are not limited to,

RQIKIWFQNRRMKWKK (penetratin);, SEQ ID NO: 27

GRKKRRQRRRPPQC (Tat fragment 48-60);, SEQ ID NO: 28

GALFLGWLGAAGSTMGAWSQPKKKRKV (signal sequence based peptide);, SEQ ID NO: 29

LLIILRRRIRKQAHAHSK (PVEC);, SEQ ID NO: 30

GWTLNSAGYLLKINLKALAALAKKIL (transportan);, SEQ ID NO: 31

KLALKLALKALKAALKLA (amphiphilic model peptide);, SEQ ID NO: 32

RRRRRRRRR (Arg9);, SEQ ID NO: 33

KFFKFFKFFK (Bacterial cell wall permeating peptide);, SEQ ID NO: 34

LLGDFFRKSKEKIGKEFKRIVQRIKDFLRNLVPRTES (LL-37);, SEQ ID NO: 35

SWLSKTAKKLENSAKKRISEGIAIAIQGGPR (cecropin P1);, SEQ ID NO: 36

ACYCRIPACIAGERRYGTCIYQGRLWAFCC (α-defensin), SEQ ID NO: 37

DHYNCVSSGGQCLYSACPIFTKIQGTCYRGKAKCCK (β-defensin);, SEQ ID NO: 38

RRRPRPPYLPRPRPPPFFPPRLPPRIPPGFPPRFPPRFPGKR-NH2 (PR-39);, SEQ ID NO: 39

ILPWKWPWWPWRR-NH2 (indolicidin);, SEQ ID NO: 40

AAVALLPAVLLALLAP (RFGF);, SEQ ID NO: 41

AALLPVLLAAP (RFGF analogue);, and SEQ ID NO: 42

RKCRIVVIRVCR (bactenecin)., SEQ ID NO: 43

Exemplary cationic groups include, but are not limited to, protonated amino groups, derived from e.g., O-AMINE (AMINE=NH$_2$; alkylamino, dialkylamino, heterocyclyl, arylamino, diaryl amino, heteroaryl amino, or diheteroaryl amino, ethylene diamine, polyamino); aminoalkoxy, e.g., O(CH$_2$)$_n$AMINE, (e.g., AMINE=NH$_2$; alkylamino, dialkylamino, heterocyclyl, arylamino, diaryl amino, heteroaryl amino, or diheteroaryl amino, ethylene diamine, polyamino); amino (e.g. NH$_2$; alkylamino, dialkylamino, heterocyclyl, arylamino, diaryl amino, heteroaryl amino, diheteroaryl amino, or amino acid); and NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino).

As used herein the term "targeting ligand" refers to any molecule that provides an enhanced affinity for a selected target, e.g., a cell, cell type, tissue, organ, region of the body, or a compartment, e.g., a cellular, tissue or organ compartment. Some exemplary targeting ligands include, but are not limited to, antibodies, antigens, folates, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands.

Carbohydrate based targeting ligands include, but are not limited to, D-galactose, multivalent galactose, N-acetyl-D-galactose (GalNAc), multivalent GalNAc, e.g. GalNAc2 and GalNAc3; D-mannose, multivalent mannose, multivalent lactose, N-acetyl-galactosamine, N-acetyl-gulucosamine, multivalent fucose, glycosylated polyaminoacids and lectins. The term multivalent indicates that more than one monosaccharide unit is present. Such monosaccharide subunits can be linked to each other through glycosidic linkages or linked to a scaffold molecule.

A number of folate and folate analogs amenable to the present invention as ligands are described in U.S. Pat. Nos. 2,816,110; 5,410,104; 5,552,545; 6,335,434 and 7,128,893, contents of which are herein incorporated in their entireties by reference.

As used herein, the terms "PK modulating ligand" and "PK modulator" refers to molecules which can modulate the pharmacokinetics of the composition of the invention. Some exemplary PK modulator include, but are not limited to, lipophilic molecules, bile acids, sterols, phospholipid analogues, peptides, protein binding agents, vitamins, fatty acids, phenoxazine, aspirin, naproxen, ibuprofen, suprofen, ketoprofen, (S)-(+)-pranoprofen, carprofen, PEGs, biotin, and transthyretia-binding ligands (e.g., tetraiidothyroacetic acid, 2,4,6-triiodophenol and flufenamic acid). Oligonucleotides that comprise a number of phosphorothioate intersugar linkages are also known to bind to serum protein, thus short oligonucleotides, e.g. oligonucleotides of comprising from about 5 to 30 nucleotides (e.g., 5 to 25 nucleotides, preferably 5 to 20 nucleotides, e.g., 5, 6, 7, 8, 9, 10, 11, 12, 13, 14, 15, 16, 17, 18, 19, or 20 nucleotides), and that comprise a plurality of phosphorothioate linkages in the backbone are also amenable to the present invention as ligands (e.g. as PK modulating ligands). The PK modulating oligonucleotide can comprise at least 3, 4, 5, 6, 7, 8, 9, 10, 11, 12, 13, 14, 15 or more phosphorothioate and/or phosphorodithioate linkages. In some embodiments, all internucleotide linkages in PK modulating oligonucleotide are phosphorothioate and/or phosphorodithioates linkages. In addition, aptamers that bind serum components (e.g. serum proteins) are also amenable to the present invention as PK modulating ligands. Binding to serum components (e.g. serum proteins) can be predicted from albumin binding assays, such as those described in Oravcova, et al., Journal of Chromatography B (1996), 677: 1-27.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

In some embodiments, ligand on one strand of double-stranded oligonucleotide has affinity for a ligand on the second strand. In some embodiments, a ligand is covalently linked to both strands of a double-stranded oligonucleotide. As used herein, when a ligand is linked to more than oligonucleotide strand, point of attachment for an oligonucleotide can be an atom of the ligand self or an atom on a carrier molecule to which the ligand itself is attached.

Ligands can be coupled to the oligonucleotides at various places, for example, 3'-end, 5'-end, and/or at an internal position. When two or more ligands are present, the ligand can be on opposite ends of an oligonucleotide. In preferred embodiments, the ligand is attached to the oligonucleotides via an intervening tether/linker. The ligand or tethered ligand can be present on a monomer when said monomer is incorporated into the growing strand. In some embodiments, the ligand can be incorporated via coupling to a "precursor" monomer after said "precursor" monomer has been incorporated into the growing strand. For example, a monomer having, e.g., an amino-terminated tether (i.e., having no associated ligand), e.g., monomer-linker-NH$_2$ can be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction can be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded RNAi agent comprises a ligand conjugated to the sense strand. In other embodiments, a double-stranded RNAi agent comprises a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position.

In some embodiments, the 2-, 5-, and 6-positions of a pyrimidine nucleobase can be substituted with a conjugate moiety. When a ligand is conjugated to a nucleobase, the preferred position is one that does not interfere with hybridization, i.e., does not interfere with the hydrogen bonding interactions needed for base pairing.

Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligomeric compounds. Generally, an oligomeric compound is attached to a conjugate moiety by contacting a reactive group (e.g., OH, SH, amine, carboxyl, aldehyde, and the like) on the oligomeric compound with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118, 802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,149,782; 5,214,136; 5,245,022; 5,254, 469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,672,662; 5,688,941; 5,714,166; 6,153, 737; 6,172,208; 6,300,319; 6,335,434; 6,335,437; 6,395,437; 6,444,806; 6,486,308; 6,525,031; 6,528,631; 6,559,279; contents which are herein incorporated in their entireties by reference.

Ligand Carriers

In some embodiments, the ligands, e.g. endosomolytic ligands, targeting ligands or other ligands, are linked to a monomer which is then incorporated into the growing oligonucleotide strand during chemical synthesis. Such monomers are also referred to as carrier monomers herein. The carrier monomer is a cyclic group or acyclic group; preferably, the cyclic group is selected from the group consisting of pyrrolidinyl, pyrazolinyl, pyrazolidinyl, imidazolinyl, imidazolidinyl, piperidinyl, piperazinyl, [1,3]-dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone. In some embodiments, the cyclic carrier monomer is based on pyrrolidinyl such as 4-hydroxyproline or a derivative thereof.

Exemplary ligands and ligand conjugated monomers amenable to the invention are described in U.S. patent application Ser. No. 10/916,185, filed Aug. 10, 2004; Ser. No. 10/946,873, filed Sep. 21, 2004; Ser. No. 10/985,426, filed Nov. 9, 2004; Ser. No. 10/833,934, filed Aug. 3, 2007; Ser. No. 11/115,989 filed Apr. 27, 2005, Ser. No. 11/119,533, filed Apr. 29, 2005; Ser. No. 11/197,753, filed Aug. 4, 2005; Ser. No. 11/944,227, filed Nov. 21, 2007; Ser. No. 12/328,528, filed Dec. 4, 2008; and Ser. No. 12/328,537, filed Dec. 4, 2008, contents which are herein incorporated in their entireties by reference for all purposes. Ligands and ligand conjugated monomers amenable to the invention are also described in International Application Nos. PCT/US04/001461, filed Jan. 21, 2004; PCT/US04/010586, filed Apr. 5, 2004; PCT/US04/011255, filed Apr. 9, 2005; PCT/US05/014472, filed Apr. 27, 2005; PCT/US05/015305, filed Apr. 29, 2005; PCT/US05/027722, filed Aug. 4, 2005; PCT/US08/061,289, filed Apr. 23, 2008; PCT/US08/071,576, filed Jul. 30, 2008; PCT/US08/085,574, filed Dec. 4, 2008 and PCT/US09/40274, filed Apr. 10, 2009, contents which are herein incorporated in their entireties by reference for all purposes.

Linkers

In some embodiments, the covalent linkages between the oligonucleotide and other components, e.g. a ligand or a ligand carrying monomer can be mediated by a linker. This linker can be cleavable linker or non-cleavable linker, depending on the application. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In some embodiments, a cleavable linker can be used to release the oligonucleotide after transport to the desired target. The intended nature of the conjugation or coupling interaction, or the desired biological effect, will determine the choice of linker group.

As used herein, the term "linker" means an organic moiety that connects two parts of a compound. Linkers typically comprise a direct bond or an atom such as oxygen or sulfur, a unit such as $NR^1$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In some embodiments, the linker is $-[(P-Q-R)_q-X-(P'-Q'-R)_{q'}]-T-$, wherein:

P, R, T, P' and R' are each independently for each occurrence absent, CO, NH, O, S, OC(O), NHC(O), $CH_2$, $CH_2NH$, $CH_2O$; $NHCH(R^a)C(O)$, $-C(O)-CH(R^a)-NH-$, C(O)-(optionally substituted alkyl)-NH—, CH=N—O,

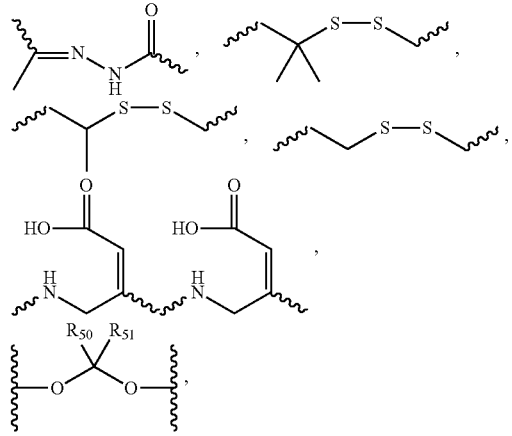

cyclyl, heterocyclyl, aryl or heteroaryl; $R_{50}$ and $R_{51}$ are independently alkyl, substituted alkyl, or $R_{50}$ and $R_{51}$ taken together to form a cyclic ring;

Q and Q' are each independently for each occurrence absent, $-(CH_2)_n-$, $-C(R^{100})(R^{200})(CH_2)_n-$, $-(CH_2)_nC(R^{100})(R_{200})-$, $-(CH_2CH_2O)_mCH_2CH_2-$, or $-(CH_2CH_2O)_mCH_2CH_2NH-$;

X is absent or a cleavable linking group;

$R^a$ is H or an amino acid side chain;

$R^{100}$ and $R^{200}$ are each independently for each occurrence H, $CH_3$, OH, SH or $N(R^X)_2$;

$R^X$ is independently for each occurrence H, methyl, ethyl, propyl, isopropyl, butyl or benzyl;

q, q' and q" are each independently for each occurrence 0-20 and wherein the repeating unit can be the same or different;

n is independently for each occurrence 1-20; and m is independently for each occurrence 0-50.

In some embodiments, the linker comprises at least one cleavable linking group.

In some embodiments, the linker is a branched linker. The branchpoint of the branched linker may be at least trivalent, but can be a tetravalent, pentavalent or hexavalent atom, or a group presenting such multiple valencies. In some embodiments, the branchpoint is, —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branchpoint is glycerol or derivative thereof.

Cleavable Linking Groups

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions)

Exemplary cleavable linking groups include, but are not limited to, redox cleavable linking groups (e.g., —S—S— and —C(R)$_2$—S—S—, wherein R is H or C$_1$-C$_6$ alkyl and at least one R is C$_1$-C$_6$ alkyl such as CH$_3$ or CH$_2$CH$_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched C$_1$-C$_{10}$ alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleaveable in an acidic environment with a pH of about 6.5 or lower (e.g., about 6.-, 5.5, 5.0, or lower), or by agents such as enzymes that acan act as a general acid.

Oligonucleotide Production

The oligonucleotide compounds of the invention can be prepared using solution-phase or solid-phase organic synthesis, or enzymatically by methods known in the art. Organic synthesis offers the advantage that the oligonucleotide strands comprising non-natural or modified nucleotides can be easily prepared. Any other means for such synthesis known in the art can additionally or alternatively be employed. It is also known to use similar techniques to prepare other oligonucleotides, such as the phosphorothioates, phosphorodithioates and alkylated derivatives. The double-stranded oligonucleotide compounds of the invention can be prepared using a two-step procedure. First, the individual strands of the double-stranded molecule are prepared separately. Then, the component strands are annealed.

Regardless of the method of synthesis, the oligonucleotide can be prepared in a solution (e.g., an aqueous and/or organic solution) that is appropriate for formulation. For example, the oligonucleotide preparation can be precipitated and redissolved in pure double-distilled water, and lyophilized. The dried oligonucleotide can then be resuspended in a solution appropriate for the intended formulation process.

In some embodiments, oligonucleotides of the invention are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

Teachings regarding the synthesis of particular modified oligonucleotides can be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having beta-lactam backbones; U.S. Pat. No. 5,571,902, drawn to methods and materials for the synthesis of oligonucleotides; U.S. Pat. No.

5,578,718, drawn to nucleosides having alkylthio groups, wherein such groups can be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, and 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

Methods of the Invention

One aspect of the present invention relates to a method of modulating the expression of a target gene in a cell. The method comprises: contacting a cell with a composition of the invention. In some embodiments, the method comprises further the step of allowing the cell to internalize the composition. In some embodiments, the method further comprises the step of providing a composition of the invention.

The method can be performed in a cell culture, e.g., in vitro or ex vivo, or in vivo, e.g., to treat a subject identified as being in need of treatment by a composition of the invention.

The term "contacting" or "contact" as used herein in connection with contacting a cell includes subjecting the cell to an appropriate culture media which comprises an oligonucleotide of the invention. Where the cell is in vivo, "contacting" or "contact" includes administering the oligonucleotide in a pharmaceutical composition to a subject via an appropriate administration route such that the oligonucleotide contacts the cell in vivo.

For in vivo methods, a therapeutically effective amount of a compound described herein can be administered to a subject. Methods of administering compounds to a subject are known in the art and easily available to one of skill in the art.

In some embodiments, the cell is a mammalian cell.

In yet another aspect, the invention provides a method for modulating the expression of the target gene in a subject. The method comprises: administering a composition featured in the invention to the subject such that expression of the target gene is modulated.

As used herein, the term "administer" refers to the placement of a composition into a subject by a method or route which results in at least partial localization of the composition at a desired site such that expression of the target gene is modulated. An oligonucleotide described herein can be administered by any appropriate route known in the art including, but not limited to oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

By "treatment", "prevention" or "amelioration" of a disease or disorder is meant delaying or preventing the onset of such a disease or disorder, reversing, alleviating, ameliorating, inhibiting, slowing down or stopping the progression, aggravation, deterioration or severity of a condition associated with such a disease or disorder. In one embodiment, the symptoms of a disease or disorder are alleviated by at least 5%, at least 10%, at least 20%, at least 30%, at least 40%, or at least 50%.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

In some embodiments of the methods described herein further comprise selecting a subject identified as being in need of treatment by an oligonucleotide or composition of the invention. A subject suffering from a disease or disorder can be selected based on the symptoms presented.

The oligonucleotide can be administrated to a subject in combination with a pharmaceutically active agent. Exemplary pharmaceutically active compound include, but are not limited to, those found in *Harrison's Principles of Internal Medicine*, 13$^{th}$ Edition, Eds. T. R. Harrison et al. McGraw-Hill N.Y., NY; Physicians Desk Reference, 50$^{th}$ Edition, 1997, Oradell N.J., Medical Economics Co.; Pharmacological Basis of Therapeutics, 8$^{th}$ Edition, Goodman and Gilman, 1990; and United States Pharmacopeia, The National Formulary, USP XII NF XVII, 1990, the complete contents of all of which are incorporated herein by reference.

The oligonucleotide and the pharmaceutically active agent may be administrated to the subject in the same pharmaceutical composition or in different pharmaceutical compositions (at the same time or at different times).

The amount of oligonucleotide which can be combined with a carrier material to produce a single dosage form will generally be that amount of the compound which produces a therapeutic effect. Generally out of one hundred percent, this amount will range from about 0.1% to 99% of oligonucleotide, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that oligonucleotide is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. Examples of dosing schedules are administration once a week, twice a week, three times a week, daily, twice daily, three times daily or four or more times daily.

Target Genes

By "gene" or "target gene" is meant, a nucleic acid that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus.

Target genes include genes promoting unwanted cell proliferation, growth factor gene, growth factor receptor gene, genes expressing kinases, an adaptor protein gene, a gene encoding a G protein super family molecule, a gene encoding a transcription factor, a gene which mediates angiogenesis, a viral gene, a gene required for viral replication, a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, a gene which mediates a neurological disease, an allene gene found in cells characterized by loss of heterozygosity, or one allege gene of a polymorphic gene.

Exemplary target genes include, but are not limited to, PDGF beta gene; Erb-B gene, Src gene; CRK gene; GRB2 gene; RAS gene; MEKK gene; JNK gene; RAF gene; Erk1/2 gene; PCNA(p21) gene; MYB gene; c-MYC gene; JUN gene; FOS gene; BCL-2 gene; Cyclin D gene; VEGF gene; EGFR gene; Cyclin A gene; Cyclin E gene; WNT-1 gene; beta-catenin gene; c-MET gene; PKC gene; NFKB gene; STAT3 gene; survivin gene; Her2/Neu gene; topoisomerase I gene; topoisomerase II alpha gene; p73 gene; p21(WAF1/CIP1) gene; p27(KIP1) gene; PPM1D gene; caveolin I gene; MIB I gene; MTAI gene; M68 gene; tumor suppressor genes; p53 gene; DN-p63 gene; pRb tumor suppressor gene; APC1 tumor suppressor gene; BRCA1 tumor suppressor gene; PTEN tumor suppressor gene; MLL fusion genes, e.g., MLL-AF9, BCR/ABL fusion gene; TEL/AML1 fusion gene; EWS/FLI1 fusion gene; TLS/FUS1 fusion gene; PAX3/FKHR fusion gene; AML1/ETO fusion gene; alpha v-integrin gene; Flt-1 receptor gene; tubulin gene; Human Papilloma Virus gene, a gene required for Human Papilloma Virus replication, Human Immunodeficiency Virus gene, a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis E Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Vericella zoster virus gene, a gene that is required for Vericella zoster virus replication, adenovirus gene, a gene that is required for adenovirus replication, yellow fever virus gene, a gene that is required for yellow fever virus replication, poliovirus gene, a gene that is required for poliovirus replication, poxvirus gene, a gene that is required for poxvirus replication, plasmodium gene, a gene that is required for plasmodium gene replication, *Mycobacterium ulcerans* gene, a gene that is required for *Mycobacterium ulcerans* replication, *Mycobacterium tuberculosis* gene, a gene that is required for *Mycobacterium tuberculosis* replication, *Mycobacterium leprae* gene, a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chlamydia pneumoniae* gene, a gene that is required for *Chlamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-1I gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, 1-309 gene, a gene to a component of an ion channel, a gene to a neurotransmitter receptor, a gene to a neurotransmitter ligand, amyloid-family gene, presenilin gene, HD gene, DRPLA gene, SCAT gene, SCA2 gene, MJD1 gene, CACNL1A4 gene, SCAT gene, SCA8 gene, allele gene found in loss of heterozygosity (LOH) cells, one allele gene of a polymorphic gene and combinations thereof.

The loss of heterozygosity (LOH) can result in hemizygosity for sequence, e.g., genes, in the area of LOH. This can result in a significant genetic difference between normal and disease-state cells, e.g., cancer cells, and provides a useful difference between normal and disease-state cells, e.g., cancer cells. This difference can arise because a gene or other sequence is heterozygous in duploid cells but is hemizygous in cells having LOH. The regions of LOH will often include a gene, the loss of which promotes unwanted proliferation, e.g., a tumor suppressor gene, and other sequences including, e.g., other genes, in some cases a gene which is essential for normal function, e.g., growth. Methods of the invention rely, in part, on the specific modulation of one allele of an essential gene with a composition of the invention.

Gene Expression Modulation

As used herein the term "modulate gene expression" means that expression of the gene, or level of RNA molecule or equivalent RNA molecules encoding one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

As used herein, gene expression modulation happens when the expression of the gene, or level of RNA molecule or equivalent RNA molecules encoding one or more proteins or protein subunits is at least 5%, 10%, 20%, 30%, 40%, 50%, 60%, 70%, 80%, 90%, 100%, 2-fold, 3-fold, 4-fold, 5-fold or more different from that observed in the absence of the modulator, e.g., RNAi agent. The % and/or fold difference can be calculated relative to the control or the non-control, for example, $$\% \text{ difference} = \frac{\left[\begin{array}{c}\text{expression with modulator} - \\ \text{expression without modulator}\end{array}\right]}{\text{expression without modulator}}$$

or $$\% \text{ difference} = \frac{\left[\begin{array}{c}\text{expression with modulator} - \\ \text{expression without modulator}\end{array}\right]}{\text{expression with modulator}}$$

As used herein, the term "inhibit", "down-regulate", or "reduce", means that the expression of the gene, or level of RNA molecules or equivalent RNA molecules encoding one or more proteins or protein subunits, or activity of one or more proteins or protein subunits, is reduced below that observed in the absence of modulator. The gene expression is down-regulated when expression of the gene, or level of RNA molecules or equivalent RNA molecules encoding one or more proteins or protein subunits, or activity of one or more proteins or protein subunits, is reduced at least 10% lower relative to a corresponding non-modulated control, and preferably at least 10%, 20%, 30%, 40%, 50%, 60%, 70%, 80%, 90%, 95%, 98%, 99% or most preferably, 100% (i.e., no gene expression).

As used herein, the term "increase" or "up-regulate", means that the expression of the gene, or level of RNA molecules or equivalent RNA molecules encoding one or more proteins or protein subunits, or activity of one or more proteins or protein subunits, is increased above that observed in the absence of modulator. The gene expression is up-regulated when expression of the gene, or level of RNA molecules or equivalent RNA molecules encoding one or more proteins or protein subunits, or activity of one or more proteins or protein subunits, is increased at least 10% relative to a corresponding non-modulated control, and preferably at least 10%, 20%, 30%, 40%, 50%, 60%, 70%, 80%, 90%, 95%, 98%, 100%, 1.1-fold, 1.25-fold, 1.5-fold, 1.75-fold, 2-fold, 3-fold, 4-fold, 5-fold, 10-fold, 50-fold, 100-fold or more.

Formulations

For ease of exposition the formulations, compositions and methods in this section are discussed largely with regard to RNAi agents. It may be understood, however, that these formulations, compositions and methods can be practiced with other oligonucleotides of the invention, e.g., antisense, antagomir, aptamer and ribozyme, and such practice is within the invention.

A formulated RNAi composition can assume a variety of states. In some examples, the composition is at least partially crystalline, uniformly crystalline, and/or anhydrous (e.g., less than 80, 50, 30, 20, or 10% water). In another example, the RNAi is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the RNAi composition is formulated in a manner that is compatible with the intended method of administration.

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An RNAi preparation can be formulated in combination with another agent, e.g., another therapeutic agent or an agent that stabilizes the RNAi agent, e.g., a protein that complex with RNAi agent to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the RNAi preparation includes another RNAi agent, e.g., a second RNAi that can mediated RNAi with respect to a second gene, or with respect to the same gene. Still other preparation can include at least 3, 5, ten, twenty, fifty, or a hundred or more different RNAi species. Such RNAi agents can mediate RNAi with respect to a similar number of different genes.

In one embodiment, the RNAi preparation includes at least a second therapeutic agent (e.g., an agent other than RNA or DNA). For example, an RNAi composition for the treatment of a viral disease, e.g., HIV, might include a known antiviral agent (e.g., a protease inhibitor or reverse transcriptase inhibitor). In another example, an RNAi agent composition for the treatment of a cancer might further comprise a chemotherapeutic agent.

Exemplary formulations are discussed below:

Liposomes

The oligonucleotides of the invention, e.g. antisense, antagomir, aptamer, ribozyme and RNAi agent can be formulated in liposomes. As used herein, a liposome is a structure having lipid-containing membranes enclosing an aqueous interior. Liposomes may have one or more lipid membranes. Liposomes may be characterized by membrane type and by size. Small unilamellar vesicles (SUVs) have a single membrane and typically range between 0.02 and 0.05 μm in diameter; large unilamellar vesicles (LUVS) are typically larger than 0.05 μm. Oligolamellar large vesicles and multilamellar vesicles have multiple, usually concentric, membrane layers and are typically larger than 0.1 μm. Liposomes with several nonconcentric membranes, i.e., several smaller vesicles contained within a larger vesicle, are termed multivesicular vesicles.

Liposomes may further include one or more additional lipids and/or other components such as cholesterol. Other lipids may be included in the liposome compositions for a variety of purposes, such as to prevent lipid oxidation, to stabilize the bilayer, to reduce aggregation during formation or to attach ligands onto the liposome surface. Any of a number of lipids may be present, including amphipathic, neutral, cationic, and anionic lipids. Such lipids can be used alone or in combination.

Additional components that may be present in a lipsomes include bilayer stabilizing components such as polyamide oligomers (see, e.g., U.S. Pat. No. 6,320,017), peptides, proteins, detergents, lipid-derivatives, such as PEG conjugated to phosphatidylethanolamine, PEG conjugated to phosphatidic acid, PEG conjugated to ceramides (see, U.S. Pat. No. 5,885,613), PEG conjugated dialkylamines and PEG conjugated 1,2-diacyloxypropan-3-amines.

Liposome can include components selected to reduce aggregation of lipid particles during formation, which may result from steric stabilization of particles which prevents charge-induced aggregation during formation. Suitable components that reduce aggregation include, but are not limited to, polyethylene glycol (PEG)-modified lipids, monosialoganglioside Gm1, and polyamide oligomers ("PAO") such as (described in U.S. Pat. No. 6,320,017). Exemplary suitable PEG-modified lipids include, but are not limited to, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Particularly preferred are PEG-modified diacylglycerols and dialkylglycerols. Other compounds with uncharged, hydrophilic, steric-barrier moieties, which prevent aggregation during formation, like PEG, Gm1, or ATTA, can also be coupled to lipids to reduce aggregation during formation. ATTA-lipids are described, e.g., in U.S. Pat. No. 6,320,017, and PEG-lipid conjugates are described, e.g., in U.S. Pat. Nos. 5,820,873, 5,534,499 and 5,885,613. Typically, the concentration of the lipid component selected to reduce aggregation is about 1 to 15% (by mole percent of lipids). It should be noted that aggregation preventing compounds do not necessarily require lipid conjugation to function properly. Free PEG or free ATTA in solution may be sufficient to prevent aggregation. If the liposomes are stable after formulation, the PEG or ATTA can be dialyzed away before administration to a subject.

Neutral lipids, when present in the liposome composition, can be any of a number of lipid species which exist either in an uncharged or neutral zwitterionic form at physiological pH. Such lipids include, for example diacylphosphatidylcholine, diacylphosphatidylethanolamine, ceramide, sphingomyelin, dihydrosphingomyelin, cephalin, and cerebrosides. The selection of neutral lipids for use in liposomes described herein is generally guided by consideration of, e.g., liposome size and stability of the liposomes in the bloodstream. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or may be isolated or synthesized by well-known techniques. In one group of embodiments, lipids containing saturated fatty acids with carbon chain lengths in the range of $C_{14}$ to $C_{22}$ are preferred. In another group of embodiments, lipids with mono or diunsaturated fatty acids with carbon chain lengths in the range of $C_{14}$ to $C_{22}$ are used. Additionally, lipids having mixtures of saturated and unsaturated fatty acid chains can be used. Preferably, the neutral lipids used in the present invention are DOPE, DSPC, POPC, DMPC, DPPC or any related phosphatidylcholine. The neutral lipids useful in the present invention may also be composed of sphingomyelin, dihydrosphingomyeline, or phospholipids with other head groups, such as serine and inositol.

The sterol component of the lipid mixture, when present, can be any of those sterols conventionally used in the field of liposome, lipid vesicle or lipid particle preparation. A preferred sterol is cholesterol.

Cationic lipids, when present in the liposome composition, can be any of a number of lipid species which carry a net positive charge at about physiological pH. Such lipids include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N', N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N, N-dimethyl-2,3-dioleyloxy)propylamine ("DODMA"), N-(1,2-dimyristyloxyprop-3-yl)-N, N-dimethyl-N-hydroxyethyl ammonium bromide ("DMRIE"), 5-carboxyspermylglycine diocaoleyamide ("DOGS"), and dipalmitoylphosphatidylethanolamine 5-carboxyspermyl-amide ("DPPES"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). Other cationic lipids suitable for lipid particle formation are described in WO98/39359, WO96/37194. Other cationic lipids suitable for liposome formation are described in U.S. Provisional applications No. 61/018, 616 (filed Jan. 2, 2008), No. 61/039,748 (filed Mar. 26, 2008), No. 61/047,087 (filed Apr. 22, 2008) and No. 61/051, 528 (filed May 21-2008), all of which are incorporated by reference in their entireties for all purposes.

Anionic lipids, when present in the liposome composition, can be any of a number of lipid species which carry a net negative charge at about physiological pH. Such lipids include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

"Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingo lipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingo lipids, glycosphingolipid families, diacylglycerols, and β-acyloxyacids, can also be used. Additionally, such amphipathic lipids can be readily mixed with other lipids, such as triglycerides and sterols.

Also suitable for inclusion in the liposome compostions of the present invention are programmable fusion lipids. Liposomes containing programmable fusion lipids have little tendency to fuse with cell membranes and deliver their payload until a given signal event occurs. This allows the liposome to distribute more evenly after injection into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the liposome membrane over time. By the time the liposome is suitably distributed in the body, it has lost sufficient cloaking agent so as to be fusogenic. With other signal events, it is desirable to choose a signal that is associated with the disease site or target cell, such as increased temperature at a site of inflammation.

A liposome can also include a targeting moiety, e.g., a targeting moiety that is specific to a cell type or tissue. Targeting of liposomes with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013,556; Zalipsky, *Bioconjugate Chemistry* 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton Fla. (1995). Other targeting moieties, such as ligands, cell surface receptors, glycoproteins, vitamins (e.g., riboflavin), aptamers and monoclonal antibodies, can also be used. The targeting moieties can include the entire protein or fragments thereof. Targeting mechanisms generally require that the targeting agents be positioned on the surface of the liposome in such a manner that the targeting moiety is available for interaction with the target, for example, a cell surface receptor.

In one approach, a targeting moiety, such as receptor binding ligand, for targeting the liposome is linked to the lipids forming the liposome. In another approach, the targeting moiety is attached to the distal ends of the PEG chains forming the hydrophilic polymer coating (Klibanov, et al., *Journal of Liposome Research* 2: 321-334 (1992); Kirpotin et al., *FEBS Letters* 388: 115-118 (1996)). A variety of different targeting agents and methods are known and available in the art, including those described, e.g., in Sapra, P. and Allen, T M, *Prog. Lipid Res.* 42(5):439-62 (2003); and Abra, R M et al., *J. Liposome Res.* 12:1-3, (2002). Other lipids conjugated with targeting moieties are described in U.S. provisional application No. 61/127,751 (filed May 14, 2008) and PCT application #PCT/US2007/080331 (filed Oct. 3, 2007), all of which are incorporated by reference in their entireties for all purposes.

A liposome composition of the invention can be prepared by a variety of methods that are known in the art. See e.g., U.S. Pat. Nos. 4,235,871, 4,897,355 and 5,171,678; published PCT applications WO 96/14057 and WO 96/37194; Feigner, P. L. et al., *Proc. Natl. Acad. Sci., USA* (1987) 8:7413-7417, Bangham, et al. *M. Mol. Biol.* (1965) 23:238, Olson, et al. *Biochim. Biophys. Acta* (1979) 557:9, Szoka, et al. *Proc. Natl. Acad. Sci.* (1978) 75: 4194, Mayhew, et al. *Biochim. Biophys. Acta* (1984) 775:169, Kim, et al. *Biochim. Biophys. Acta* (1983) 728:339, and Fukunaga, et al. *Endocrinol.* (1984) 115:757.

For example, a liposome composition of the invention can be prepared by first dissolving the lipid components of a liposome in a detergent so that micelles are formed with the lipid component. The detergent can have a high critical micelle concentration and maybe nonionic. Exemplary detergents include, but are not limited to, cholate, CHAPS, octylglucoside, deoxycholate and lauroyl sarcosine. The RNAi agent preparation e.g., an emulsion, is then added to the micelles that include the lipid components. After condensation, the detergent is removed, e.g., by dialysis, to yield a liposome containing the RNAi agent. If necessary a carrier compound that assists in condensation can be added during the condensation reaction, e.g., by controlled addition. For example, the carrier compound can be a polymer other than a nucleic acid (e.g., spermine or spermidine). To favor condensation, pH of the mixture can also be adjusted.

In another example, liposomes of the present invention may be prepared by diffusing a lipid derivatized with a hydrophilic polymer into preformed liposome, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the RNAi agent is first dispersed by sonication in a lysophosphatidylcholine or other low CMC surfactant (including polymer grafted lipids). The resulting micellar suspension of RNAi agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323.

Other suitable formulations for RNAi agents are described in PCT application #PCT/US2007/080331 (filed Oct. 3, 2007) and U.S. Provisional applications No. 61/018, 616 (filed Jan. 2, 2008), No. 61/039,748 (filed Mar. 26, 2008), No. 61/047,087 (filed Apr. 22, 2008) and No. 61/051, 528 (filed May 21-2008), No. 61/113,179 (filed Nov. 10, 2008) all of which are incorporated by reference in their entireties for all purposes.

Micelles and other Membranous Formulations

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

As defined herein, "micelles" are a particular type of molecular assembly in which amphipathic molecules are arranged in a spherical structure such that all hydrophobic portions on the molecules are directed inward, leaving the hydrophilic portions in contact with the surrounding aqueous phase. The converse arrangement exists if the environment is hydrophobic.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Exemplary amphiphilic carriers include, but are not limited to, lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, mono laurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-. di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Mixed micelle formulation suitable for delivery through transdermal membranes may be prepared by mixing an aqueous solution of the RNAi composition, an alkali metal $C_8$ to $C_{22}$ alkyl sulphate, and an amphiphilic carrier. The amphiphilic carrier may be added at the same time or after addition of the alkali metal alkyl sulphate. Mixed micelles will form with substantially any kind of mixing of the ingredients but vigorous mixing in order to provide smaller size micelles.

In one method a first micelle composition is prepared which contains the RNAi composition and at least the alkali metal alkyl sulphate. The first micelle composition is then mixed with at least three amphiphilic carriers to form a mixed micelle composition. In another method, the micelle composition is prepared by mixing the RNAi composition, the alkali metal alkyl sulphate and at least one of the amphiphilic carriers, followed by addition of the remaining micelle amphiphilic carriers, with vigorous mixing.

Phenol and/or m-cresol may be added to the mixed micelle composition to stabilize the formulation and protect against bacterial growth. Alternatively, phenol and/or m-cresol may be added with the amphiphilic carriers. An isotonic agent such as glycerin may also be added after formation of the mixed micelle composition.

For delivery of the micelle formulation as a spray, the formulation can be put into an aerosol dispenser and the dispenser is charged with a propellant, such as hydrogen-containing chlorofluorocarbons, hydrogen-containing fluorocarbons, dimethyl ether, diethyl ether and HFA 134a (1,1,1,2 tetrafluoroethane).

Emulsions

The oligonucleotides of the present invention may be prepared and formulated as emulsions. Emulsions are typically heterogenous systems of one liquid dispersed in another in the form of droplets (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: non-ionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials is also included in emulsion formulations and contributes to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of FLiPs are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (M0750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations of the present invention will facilitate the increased systemic absorption of dsRNAs and nucleic acids from the gastrointestinal tract, as well as improve the local cellular uptake of dsRNAs and nucleic acids.

Microemulsions of the present invention may also contain additional components and additives such as sorbitan monostearate (Grill 3), Labrasol, and penetration enhancers to improve the properties of the formulation and to enhance the absorption of the dsRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Lipid Particles

It has been shown that cholesterol-conjugated sRNA is bind to HDL and LDL lipoprotein particles which mediate cellular uptake upon binding to their respective receptors. Both high-density lipoproteins (HDL) and low density lipoproteins (LDL) play a critical role in cholesterol transport. HDL directs sRNAi delivery into liver, gut, kidney and steroidogenic organs, whereas LDL targets sRNAi primarily to liver (Wolfrum et al. Nature Biotechnology Vol. 25 (2007)). Thus in one aspect the invention provides formulated lipid particles (FLiPs) comprising (a) an oligonucleotide of the invention, e.g., antisense, antagomir, aptamer, ribozyme and an RNAi agent, where said oligonucleotide has been conjugated to a lipophile and (b) at least one lipid component, for example an emulsion, liposome, isolated lipoprotein, reconstituted lipoprotein or phospho lipid, to which the conjugated oligonucleotide has been aggregated, admixed or associated.

The stoichiometry of oligonucleotide to the lipid component may be 1:1. Alternatively the stoichiometry may be 1:many, many:1 or many:many, where many is greater than 2.

The FLiP may comprise triacylglycerol, phospho lipids, glycerol and one or several lipid-binding proteins aggregated, admixed or associated via a lipophilic linker molecule with a single- or double-stranded oligonucleotide, wherein said FLiP has an affinity to heart, lung and/or muscle tissue. Surprisingly, it has been found that due to said one or several lipid-binding proteins in combination with the above mentioned lipids, the affinity to heart, lung and/or muscle tissue is very specific. These FLiPs may therefore serve as carrier for oligonucleotides. Due to their affinity to heart, lung and muscle cells, they may specifically transport the oligonucleotides to these tissues. Therefore, the FLiPs according to the present invention may be used for many severe heart, lung and muscle diseases, for example myocarditis, ischemic heart disease, myopathies, cardiomyopathies, metabolic diseases, rhabdomyo sarcomas.

One suitable lipid component for FLiP is Intralipid. Intralipid® is a brand name for the first safe fat emulsion for human use. Intralipid® 20% (a 20% intravenous fat emulsion) is a sterile, non-pyrogenic fat emulsion prepared for intravenous administration as a source of calories and essential fatty acids. It is made up of 20% soybean oil, 1.2% egg yolk phospholipids, 2.25% glycerin, and water for injection. Intralipid® 10% is made up of 10% soybean oil, 1.2% egg yolk phospho lipids, 2.25% glycerin, and water for injection. It is further within the present invention that other suitable oils, such as safflower oil, may serve to produce the lipid component of the FLiP.

In one embodiment of the invention is a FLiP comprising a lipid particle comprising 15-25% triacylglycerol, about 1-2% phospholipids and 2-3% glycerol, and one or several lipid-binding proteins.

In another embodiment of the invention the lipid particle comprises about 20% triacylglycerol, about 1.2% phospholipids and about 2.25% glycerol, which corresponds to the total composition of Intralipid, and one or several lipid-binding proteins.

Another suitable lipid component for FLiPs is lipoproteins, for example isolated lipoproteins or more preferably reconstituted lipoproteins. Lipoproteins are particles that contain both proteins and lipids. The lipids or their derivatives may be covalently or non-covalently bound to the proteins. Exemplary lipoproteins include chylomicrons, VLDL (Very Low Density Lipoproteins), IDL (Intermediate Density Lipoproteins), LDL (Low Density Lipoproteins) and HDL (High Density Lipoproteins).

Methods of producing reconstituted lipoproteins have been described in scientific literature, for example see A. Jones, Experimental Lung Res. 6, 255-270 (1984), U.S. Pat. Nos. 4,643,988 and 5,128,318, PCT publication WO87/02062, Canadian patent #2,138,925. Other methods of producing reconstituted lipoproteins, especially for apolipoproteins A-I, A-II, A-IV, apoC and apoE have been described in A. Jonas, Methods in Enzymology 128, 553-582 (1986) and G. Franceschini et al. J. Biol. Chem., 260(30), 16321-25 (1985).

The most frequently used lipid for reconstitution is phosphatidyl choline, extracted either from eggs or soybeans. Other phospholipids are also used, also lipids such as triglycerides or cholesterol. For reconstitution the lipids are first dissolved in an organic solvent, which is subsequently evaporated under nitrogen. In this method the lipid is bound in a thin film to a glass wall. Afterwards the apolipoproteins and a detergent, normally sodium cholate, are added and mixed. The added sodium cholate causes a dispersion of the lipid. After a suitable incubation period, the mixture is dialyzed against large quantities of buffer for a longer period of time; the sodium cholate is thereby removed for the most part, and at the same time lipids and apolipoproteins spontaneously form themselves into lipoproteins or so-called reconstituted lipoproteins. As alternatives to dialysis, hydrophobic adsorbents are available which can adsorb detergents (Bio-Beads SM-2, Bio Rad; Amberlite XAD-2, Rohm & Haas) (E. A. Bonomo, J. B. Swaney, J. Lipid Res., 29, 380-384 (1988)), or the detergent can be removed by means of gel chromatography (Sephadex G-25, Pharmacia). Lipoproteins can also be produced without detergents, for example through incubation of an aqueous suspension of a suitable lipid with apolipoproteins, the addition of lipid which was dissolved in an organic solvent, to apolipoproteins, with or without additional heating of this mixture, or through treatment of an apoA-I-lipid-mixture with ultrasound. With these methods, starting, for example, with apoA-I and phosphatidyl choline, disk-shaped particles can be obtained which correspond to lipoproteins in their nascent state. Normally, following the incubation, unbound apolipoproteins and free lipid are separated by means of centrifugation or gel chromatography in order to isolate the homogeneous, reconstituted lipoproteins particles.

Phospholipids used for reconstituted lipoproteins can be of natural origin, such as egg yolk or soybean phospholipids, or synthetic or semisynthetic origin. The phospholipids can be partially purified or fractionated to comprise pure fractions or mixtures of phosphatidyl cholines, phosphatidyl ethanolamines, phosphatidyl inositols, phosphatidic acids, phosphatidyl serines, sphingomyelin or phosphatidyl glycerols. According to specific embodiments of the present invention it is preferred to select phospho lipids with defined fatty acid radicals, such as dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), and combinations thereof, and the like phosphatidyl cholines with defined acyl groups selected from naturally occurring fatty acids, generally having 8 to 22 carbon atoms. According to a specific embodiment of the present invention phosphatidyl cholines having only saturated fatty acid residues between 14 and 18 carbon atoms are preferred, and of those dipalmitoyl phosphatidyl choline is especially preferred.

Other phospho lipids suitable for reconstitution with lipoproteins include, e.g., phosphatidylcholine, phosphatidylglycerol, lecithin, b, g-dipalmitoyl-a-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, and the like. Non-phosphorus containing lipids may also be used in the liposomes of the compositions of the present invention. These include, e.g., stearylamine, docecylamine, acetyl palmitate, fatty acid amides, and the like.

Besides the phospho lipids, the lipoprotein may comprise, in various amounts at least one nonpolar component which can be selected among pharmaceutical acceptable oils (triglycerides) exemplified by the commonly employed vegetabilic oils such as soybean oil, safflower oil, olive oil, sesame oil, borage oil, castor oil and cottonseed oil or oils from other sources like mineral oils or marine oils including hydrogenated and/or fractionated triglycerides from such sources. Also medium chain triglycerides (MCT-oils, e.g. Miglyol®), and various synthetic or semisynthetic mono-, di- or triglycerides, such as the defined nonpolar lipids disclosed in WO 92/05571 may be used in the present invention as well as acetylated monoglycerides, or alkyl esters of fatty acids, such isopropyl myristate, ethyl oleate (see EP 0 353 267) or fatty acid alcohols, such as oleyl alcohol, cetyl alcohol or various nonpolar derivatives of cholesterol, such as cholesterol esters.

One or more complementary surface active agent can be added to the reconstituted lipoproteins, for example as complements to the characteristics of amphiphilic agent or to improve its lipid particle stabilizing capacity or enable an improved solubilization of the protein. Such complementary agents can be pharmaceutically acceptable non-ionic surfactants which preferably are alkylene oxide derivatives of an organic compound which contains one or more hydroxylic groups. For example ethoxylated and/or propoxylated alcohol or ester compounds or mixtures thereof are commonly available and are well known as such complements to those skilled in the art. Examples of such compounds are esters of sorbitol and fatty acids, such as sorbitan monopalmitate or sorbitan monopalmitate, oily sucrose esters, polyoxyethylene sorbitane fatty acid esters, polyoxyethylene sorbitol fatty acid esters, polyoxyethylene fatty acid esters, polyoxyethylene alkyl ethers, polyoxyethylene sterol ethers, polyoxyethylene-polypropoxy alkyl ethers, block polymers and cethyl ether, as well as polyoxyethylene castor oil or hydrogenated castor oil derivatives and polyglycerine fatty acid esters. Suitable non-ionic surfactants, include, but are not limited to various grades of Pluronic®, Poloxamer®, Span®, Tween®, Polysorbate®, Tyloxapol®, Emulphor® or Cremophor® and the like. The complementary surface active agents may also be of an ionic nature, such as bile duct agents, cholic acid or deoxycholic their salts and derivatives or free fatty acids, such as oleic acid, linoleic acid and others. Other ionic surface active agents are found among cationic lipids like C10-C24: alkylamines or alkanolamine and cationic cholesterol esters.

In the final FLiP, the oligonucleotide component is aggregated, associated or admixed with the lipid components via a lipophilic moiety. This aggregation, association or admixture may be at the surface of the final FLiP formulation. Alternatively, some integration of any of a portion or all of the lipophilic moiety may occur, extending into the lipid particle. Any lipophilic linker molecule that is able to bind oligonucleotides to lipids can be chosen. Examples include pyrrolidine and hydroxyprolinol.

The process for making the lipid particles comprises the steps of:
a) mixing a lipid components with one or several lipophile (e.g. cholesterol) conjugated oligonucleotides that may be chemically modified;
b) fractionating this mixture;
c) selecting the fraction with particles of 30-50 nm, preferably of about 40 nm in size.

Alternatively, the FLiP can be made by first isolating the lipid particles comprising triacylglycerol, phospholipids, glycerol and one or several lipid-binding proteins and then mixing the isolated particles with >2-fold molar excess of lipophile (e.g. cholesterol) conjugated oligonucleotide. The steps of fractionating and selecting the particles are deleted by this alternative process for making the FLiPs.

Other pharmacologically acceptable components can be added to the FLiPs when desired, such as antioxidants (exemplified by alpha-tocopherol) and solubilization adjuvants (exemplified by benzylalcohol).

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be ω-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Polymers

Hydrophilic polymers suitable for use in the formulations of the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG (750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In one embodiment, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and ω-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Surfactants

The above discussed formulation may also include one or more surfactants. Surfactants find wide application in formulations such as emulsions (including micro emulsions) and liposomes. The use of surfactants in drug products, formulations and in emulsions has been reviewed (Rieger, in "Pharmaceutical Dosage Forms," Marcel Dekker, Inc., New York, N.Y., 1988, p. 285). Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Nonionic surfactants include, but are not limited to, nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

Anionic surfactants include, but are not limited to, carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

Cationic surfactants include, but are not limited to, quaternary ammonium salts and ethoxylated amines. The quaternary ammonium salts are the most used members of this class.

Amphoteric surfactants include, but are not limited to, acrylic acid derivatives, substituted alkylamides, N-alkylbetaines and phosphatides.

A surfactant may also be selected from any suitable aliphatic, cycloaliphatic or aromatic surfactant, including but not limited to biocompatible lysophosphatidylcholines (LPCs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Penetration Enhancers

In one embodiment, the formulations of the present invention employ various penetration enhancers to affect the efficient delivery of RNAi agents to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Pharmaceutical Compositions

In another aspect, the present invention provides pharmaceutically acceptable compositions which comprise a therapeutically-effective amount of one or more of the oligonucleotides described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In one embodiment, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In one embodiment, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Formulations for ocular administration can include mucomimetics such as hyaluronic acid, chondroitin sulfate, hydroxypropyl methylcellulose or poly (vinyl alcohol), preservatives such as sorbic acid, EDTA or benzylchronium chloride, and the usual quantities of diluents and/or carriers.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" 0 and B books, Corvallis, Ore., U.S.A., 1977).

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims.

As used herein, the term "nucleoside" refers to a compound comprising a heterocyclic base moiety and a sugar moiety. Nucleosides include, but are not limited to, naturally occurring nucleosides (as found in DNA and RNA), abasic nucleosides, modified nucleosides, and sugar-modified nucleosides. Nucleosides may be modified with any of a variety of substituents.

As used herein, "sugar moiety" means a natural (furanosyl), a modified sugar moiety or a sugar surrogate.

As used herein, "modified sugar moiety" means a chemically-modified furanosyl sugar or a non-furanosyl sugar moiety. Also, embraced by this term are furanosyl sugar analogs and derivatives including bicyclic sugars, tetrahydropyrans, morpholinos, 2'-modified sugars, 4'-modified sugars, 5'-modified sugars, and 4'-substituted sugars.

As used herein the term "sugar surrogate" refers to a structure that is capable of replacing the furanose ring of a naturally occurring nucleoside. In certain embodiments, sugar surrogates are non-furanose (or 4'-substituted furanose) rings or ring systems or open systems. Such structures include simple changes relative to the natural furanose ring, such as a six membered ring or may be more complicated as is the case with the non-ring system used in peptide nucleic acid. Sugar surrogates includes without limitation morpholinos and cyclohexenyls and cyclohexitols. In most nucleosides having a sugar surrogate group the heterocyclic base moiety is generally maintained to permit hybridization.

As used herein, "nucleobase" refers to the heterocyclic base portion of a nucleoside. Nucleobases may be naturally occurring or may be modified and therefore include, but are not limited to adenine, cytosine, guanidine, uracil, thymidine and analogues thereof. In certain embodiments, a nucleobase may comprise any atom or group of atoms capable of hydrogen bonding to a base of another nucleic acid.

The term "duplex" includes a region of complementarity between two regions of two or more polynucleotides that comprise separate strands, such as a sense strand and an antisense strand, or between two regions of a single contiguous polynucleotide.

The phrase "first 5' terminal nucleotide" includes first 5' terminal antisense nucleotides and first 5' terminal antisense nucleotides. "First 5' terminal antisense nucleotide" refers to the nucleotide of the antisense strand that is located at the 5' most position of that strand with respect to the bases of the antisense strand that have corresponding complementary bases on the sense strand. Thus, in a double stranded polynucleotide that is made of two separate strands, it refers to the 5' most base other than bases that are part of any 5' overhang on the antisense strand. When the first 5' terminal antisense nucleotide is part of a hairpin molecule, the term "terminal" refers to the 5' most relative position within the antisense region and thus is the 5" most nucleotide of the antisense region. The phrase "first 5" terminal sense nucleotide" is defined in reference to the sense nucleotide. In molecules comprising two separate strands, it refers to the nucleotide of the sense strand that is located at the 5' most position of that strand with respect to the bases of the sense strand that have corresponding complementary bases on the antisense strand. Thus, in a double stranded polynucleotide that is made of two separate strands, it is the 5' most base other than bases that are part of any 5' overhang on the sense strand.

In one embodiment, an RNAi agent is "sufficiently complementary" to a target sequence, e.g., a target mRNA, such that the RNAi agent silences production of protein encoded by the target mRNA. In another embodiment, the RNAi agent is "exactly complementary" to a target sequence, e.g., the target RNA and the RNAi agent anneal, for example to form a hybrid made exclusively of Watson-Crick base pairs in the region of exact complementarity. A "sufficiently complementary" RNAi agent can include an internal region (e.g., of at least 10 nucleotides) that is exactly complementary to a target sequence. Moreover, In one embodiment, the RNAi agent specifically discriminates a single-nucleotide difference. In this case, the RNAi agent only mediates RNAi if exact complementary is found in the region (e.g., within 7 nucleotides of) the single-nucleotide difference.

The phrase "pharmaceutically acceptable carrier or diluent" includes compositions that facilitate the introduction of nucleic acid therapeutics such as siRNA, dsRNA, dsDNA, shRNA, microRNA, antimicroRNA, antagomir, antimir, antisense, aptamer or dsRNA/DNA hybrids into a cell and includes but is not limited to solvents or dispersants, coatings, anti-infective agents, isotonic agents, and agents that mediate absorption time or release of the inventive polynucleotides and double stranded polynucleotides. The phrase "pharmaceutically acceptable" includes approval by a regulatory agency of a government, for example, the U.S. federal government, a non-U.S. government, or a U.S. state government, or inclusion in a listing in the U.S. Pharmacopeia or any other generally recognized pharmacopeia for use in animals, including in humans.

The term "halo" refers to any radical of fluorine, chlorine, bromine or iodine.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as ($C_1$-$C_6$)alkanoyl (e.g., formyl, acetyl, propionyl, butyryl, valeryl, caproyl, t-butylacetyl, etc.), (C3-Ce)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "alkyl" refers to a saturatednon-aromatic hydrocarbon chain. Alkyls may be a straight chain or branched chain and contain the indicated number of carbon atoms For example, $C_1$-$C_{10}$ indicates that the group may have from 1 to 10 (inclusive) carbon atoms in it.

The term "alkenyl" refers to a non-aromatic hydrocarbon chain containing at least one carbon-cabon double bond. Alkenyls may be a straight chain or branched chain, containing the indicated number of carbon atoms For example, $C_2$-$C_{10}$ indicates that the group may have from 2 to 10 (inclusive) carbon atoms in it.

The term "alkynyl" refers to a non-aromatic hydrocarbon chain containing at least one carbon-cabon triple bond. Alkynyls may be a straight chain or branched chain, containing the indicated number of carbon atoms For example, $C_2$-$C_{10}$ indicates that the group may have from 2 to 10 (inclusive) carbon atoms in it.

The term "heteroalkyl" refers to a group comprising an alkyl and at least one heteroatom. In certain such embodiments, the heteroatom is selected from O, S, and N. Certain heteroalkyls are acylalkyls, in which one or more heteroatoms are within the alkyl chain. Certain heteroalkyls are non-acylalkyl heteroalkyls, in which the heteroatom is not within the alkyl chain. Examples of heteroalkyls include, but are not limited to: $CH_3C(=O)CH_2$—, $CH_3OCH_2CH_2$—, $CH_3NHCH_2$—, $CH_3SHCH_2$—, and the like. The terms "heteroalkenyl" and "heteroalkynyl" refer to groups comprising an alkenyl or alkynyl repectively and at least heteroatom.

The term "alkoxy" refers to an —O-alkyl radical. The term "alkylene" refers to a divalent alkyl (i.e., —R—). The term "alkylenedioxo" refers to a divalent species of the structure —O—R—O—, in which R represents an alkylene. The term "aminoalkyl" refers to an alkyl substituted with an amino. The term "mercapto" refers to an —SH radical. The term "thioalkoxy" refers to an —S-alkyl radical.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" or "heterocyclic" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an identified group at any atom of that group. Suitable substituents include, without limitation, halo, hydroxy, oxo, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, aryloxy, cyano, ureido or conjugate groups.

In many cases, protecting groups are used during preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p. 1) and various substituted sulfonylethyl carbamates exemplified by the Nsc group (Samukov et al., *Tetrahedron Lett.* 1994, 35, 7821; Verhart and Tesser, *Rec. Trav. Chim. Pays-Bas* 1987, 107, 621).

Additional amino-protecting groups include, but are not limited to, carbamate protecting groups, such as 2-trimethylsilylethoxycarbonyl (Teoc), 1-methyl-1-44-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the present invention.

Evaluation of Candidate Oligonucleotides

One can evaluate a candidate oligonucleotide, e.g., a modified RNA, for a selected property by exposing the agent or modified molecule and a control molecule to the appropriate conditions and evaluating for the presence of the selected property. For example, resistance to a degradent can be evaluated as follows. A candidate modified oligonucleotide (and a control molecule, usually the unmodified form) can be exposed to degradative conditions, e.g., exposed to a milieu, which includes a degradative agent, e.g., a nuclease. E.g., one can use a biological sample, e.g., one that is similar to a milieu, which might be encountered, in therapeutic use, e.g., blood or a cellular fraction, e.g., a cell-free homogenate or disrupted cells. The candidate and control could then be evaluated for resistance to degradation by any of a number of approaches. For example, the candidate and control could be labeled prior to exposure, with, e.g., a radioactive or enzymatic label, or a fluorescent label, such as Cy3 or Cy5. Control and oligonucleotide can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to silence gene expression. For example, a cell, e.g., a mammalian cell, such as a mouse or human cell, can be ω-transfected with a plasmid expressing a fluorescent protein, e.g., GFP, and a candidate oligonucleotide homologous to the transcript encoding the fluorescent protein (see, e.g., WO 00/44914). For example, a modified oligonucleotide homologous to the GFP mRNA can be assayed for the ability to inhibit GFP expression by monitoring for a decrease in cell fluorescence, as compared to a control cell, in which the transfection did not include the candidate dsiRNA, e.g., controls with no agent added and/or controls with a non-modified RNA added. Efficacy of the candidate agent on gene expression can be assessed by comparing cell fluorescence in the presence of the modified oligonucleotide and unmodified dssiRNA compounds.

In an alternative functional assay, a candidate oligonucleotide compound homologous to an endogenous mouse gene, for example, a maternally expressed gene, such as c-mos, can be injected into an immature mouse oocyte to assess the ability of the agent to inhibit gene expression in vivo (see, e.g., WO 01/36646). A phenotype of the oocyte, e.g., the ability to maintain arrest in metaphase II, can be monitored as an indicator that the agent is inhibiting expression. For example, cleavage of c-mos mRNA by an oligonucleotide would cause the oocyte to exit metaphase arrest and initiate parthenogenetic development (Colledge et al. Nature 370: 65-68, 1994; Hashimoto et al. Nature, 370:68-71, 1994). The effect of the oligonucleotide on target RNA levels can be verified by Northern blot to assay for a decrease in the level of target mRNA, or by Western blot to assay for a decrease in the level of target protein, as compared to a negative control. Controls can include cells in which with no agent is added.

Kits

In some aspects, the invention provides kits that include a suitable container containing an oligonucleotide formulation, e.g., pharmaceutical composition. In addition to the formulation, the kit can include informational material. The informational material can be descriptive, instructional, marketing or other material that relates to the methods described herein and/or the use of the compound for the methods described herein. For example, the informational material describes methods for administering the formulation to a subject. The kit can also include a delivery device.

In one embodiment, the informational material can include instructions to administer the formulation in a suitable manner, e.g., in a suitable dose, dosage form, or mode of administration (e.g., a dose, dosage form, or mode of administration described herein). In another embodiment, the informational material can include instructions for identifying a suitable subject, e.g., a human, e.g., an adult human. The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In some embodiments the individual components of the formulation can be provided in one container. Alternatively, it can be desirable to provide the components of the formulation separately in two or more containers, e.g., one container for an oligonucleotide preparation, and at least another for a carrier compound. The different components can be combined, e.g., according to instructions provided with the kit. The components can be combined according to a method described herein, e.g., to prepare and administer a pharmaceutical composition.

In addition to the formulation, the composition of the kit can include other ingredients, such as a solvent or buffer, a stabilizer or a preservative, and/or a second agent for treating a condition or disorder described herein. Alternatively, the other ingredients can be included in the kit, but in different compositions or containers than the formulation. In such embodiments, the kit can include instructions for admixing the formulation and the other ingredients, or for using the oligonucleotide together with the other ingredients.

The oligonucleotide formulation can be provided in any form, e.g., liquid, dried or lyophilized form. It is preferred that the formulation be substantially pure and/or sterile. When the formulation is provided in a liquid solution, the liquid solution preferably is an aqueous solution, with a sterile aqueous solution being preferred. When the formulation is provided as a dried form, reconstitution generally is by the addition of a suitable solvent. The solvent, e.g., sterile water or buffer, can optionally be provided in the kit.

In some embodiments, the kit contains separate containers, dividers or compartments for the formulation and informational material. For example, the formulation can be contained in a bottle, vial, or syringe, and the informational material can be contained in a plastic sleeve or packet. In other embodiments, the separate elements of the kit are contained within a single, undivided container. For example, the formulation is contained in a bottle, vial or syringe that has attached thereto the informational material in the form of a label.

In some embodiments, the kit includes a plurality, e.g., a pack, of individual containers, each containing one or more unit dosage forms of the formulation. For example, the kit includes a plurality of syringes, ampules, foil packets, or blister packs, each containing a single unit dose of the formulation. The containers of the kits can be air tight and/or waterproof.

EXAMPLES

The invention now being generally described, it will be more readily understood by reference to the following examples which are included merely for purposes of illustration of certain aspects and embodiments of the present invention, and are not intended to limit the invention.

The compounds of the inventions may be prepared by any process known to be applicable to the preparation of chemically-related compounds. Necessary starting materials may be obtained by standard procedures of organic chemistry. Alternatively necessary starting materials are obtainable by analogous procedures to those illustrated which are within the ordinary skill of a chemist. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Synthesis of GNA Nucleoside Building Blocks

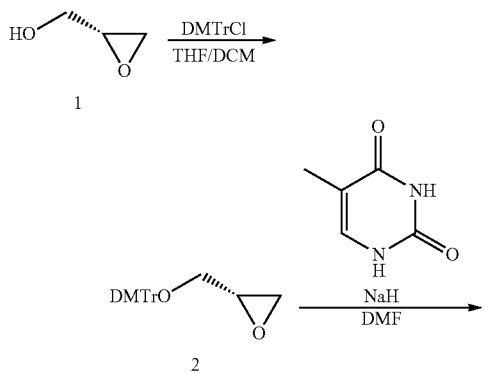

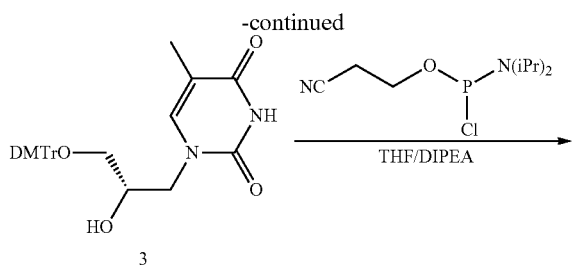

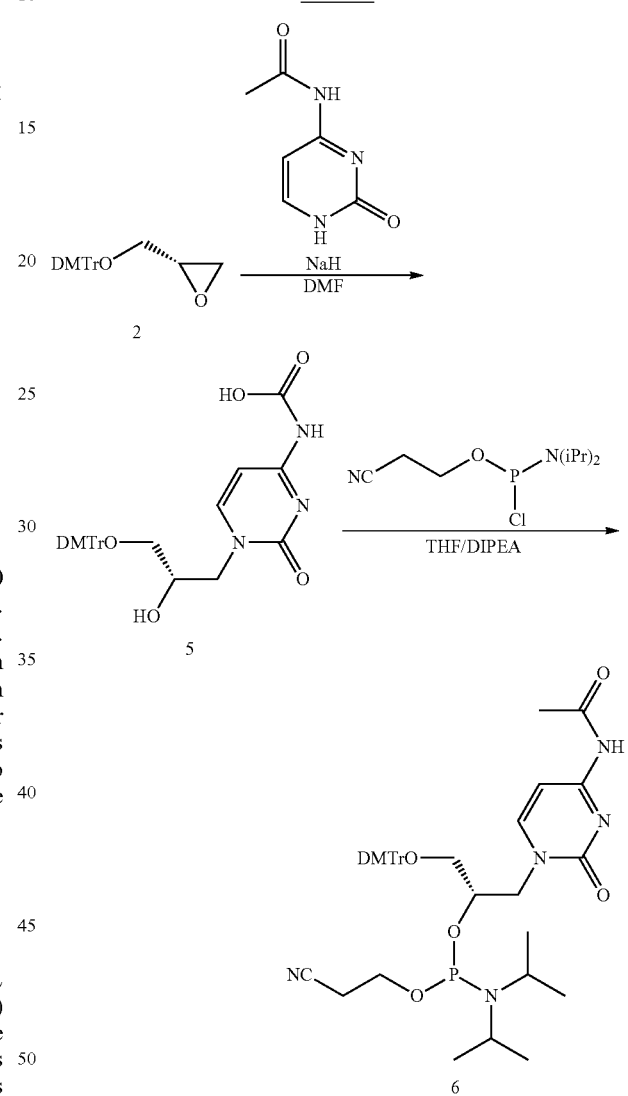

tion, the reaction mixture was filtered and evaporated to dryness to give a white foam. This was purified by column chromatography using a gradient of 7:3 hexanes/ethyl acetate with 1% TEA to 50:50 hexanes ethyl acetate with 1% TEA. The final compound 4 was obtained in 90% yield. $^{31}$P NMR (121 MHz, CD$_3$CN) 154.7, 154.2. ESI-TOF: calc. 702.3 (M$^+$) found 702.2 (M$^+$).

Synthesis of Thymine GNA phosphoramidite (according to Meggers, *Synthesis*, 2006)

(S)-2-((bis(4-methoxyphenyl)(phenyl)methoxy)methyl)oxirane (2)

A solution of (R)-(+)-glycidol 1 (64 mmol) and TEA (240 mmol) in DCM (200 mL) was prepared under dry nitrogen. This was followed by the addition of DMTrCl (83 mmol). The reaction mixture was then stirred 16 h. It was then poured into sat. aq. Sodium bicarbonate and was mixed with ethyl acetate. The organic layer was collected, dried over sodium sulfate, filtered and evaporated in vacuo. It was purified by column chromatography using a gradient up to 10:1 hexanes/EtOAc with 1% TEA to give 2 in quantitative yield.

(S)-1-(3-(bis(4-methoxyphenyl)(phenyl)methoxy)-2-hydroxypropyl)-5-methylpyrimidine-2,4(1H,3H)-dione (3)

Thymidine (14 mmol) was dried overnight in a 100 mL round bottom flask and then suspended in DMF (22 mL) under a nitrogen atmosphere. This was followed by the addition of NaH (3.3 mmol). The reaction mixture was allowed to stir for 2 h at room temperature. This was followed by the addition of 2 in DMF (22 mL). The reaction mixture was then heated to 110° C. and kept overnight. Upon completion of the reaction, it was evaporated to dryness and coevaporated with toluene and ethyl acetate. It was then purified by column chromatography using 1:2 hexanes/EtOAc to give 3 in 30% yield.

(S)-1-(3-(bis(4-methoxyphenyl)(phenyl)methoxy)-2-((bis(diisopropylamino)phosphino)oxy)propyl)-5-methylpyrimidine-2,4(1H,3H)-dione (4)

Compound 3 (5.2 mmol) was dissolved in THF (10 mL) under a dry nitrogen environment. This was followed by the addition of DIPEA (22 mmol) and the dropwise addition of O-cyanoethyldiisopropyl phosphorochlorodite (6.2 mmol). The reaction was allowed to proceed for 6 h. Upon comple- Synthesis of cytidine GNA phosphoramidite (according to Meggers, *Synthesis*, 2006)

(S)-(1-(3-(bis(4-methoxyphenyl)(phenyl)methoxy)-2-hydroxypropyl)-2-oxo-1,2-dihydropyrimidin-4-yl)carbamic acid (5)

N-acetyl Cytosine (14 mmol) is dried overnight in a 100 mL round bottom flask and then suspended in DMF (22 mL) under a nitrogen atmosphere. This is followed by the addition of NaH (3.3 mmol). The reaction mixture is allowed to stir for 2 h at room temperature. This is followed by the addition of 2 in DMF (22 mL). The reaction mixture is then heated to 110° C. and kept overnight. Upon completion of the reaction, it is evaporated to dryness and coevaporated with toluene and ethyl acetate. It is then purified by column chromatography to give 5.

(S)-1-(4-acetamido-2-oxopyrimidin-1(2H)-yl)-3-(bis(4-methoxyphenyl)(phenyl)methoxy)propan-2-yl (2-cyanoethyl) diisopropylphosphoramidite (6)

Compound 5 (5.2 mmol) is dissolved in THF (10 mL) under a dry nitrogen environment. This is followed by the addition of DIPEA (22 mmol) and the dropwise addition of O-cyanoethyldiisopropyl phosphorochlorodite (6.2 mmol). The reaction is allowed to proceed for 6 h. Upon completion, the reaction mixture is filtered and evaporated to dryness to give a white foam. This is purified by column chromatography to give 6.

under a nitrogen atmosphere. This is followed by the addition of NaH (3.3 mmol). The reaction mixture is allowed to stir for 2 h at room temperature. This is followed by the addition of 2 in DMF (22 mL). The reaction mixture is then heated to 110° C. and kept overnight. Upon completion of the reaction, it is evaporated to dryness and coevaporated with toluene and ethyl acetate. It is then purified by column chromatography to give 7.

(S,Z)-N'-(9-(3-(bis(4-methoxyphenyl)(phenyl)methoxy)-2-hydroxypropyl)-9H-purin-6-yl)-N,N-dimethylformimidamide (8)

Compound 7 (5.2 mmol) is dissolved in methanol (40 mL). This is followed by the addition of dimethyl formamidine dimethyl acetal (20 mmol) and stirring for 16 h. The reaction mixture is then evaporated to dryness and purified by column chromatography to give 8.

(S)-1-(bis(4-methoxyphenyl)(phenyl)methoxy)-3-(6-((Z)-((dimethylamino)methylene)amino)-9H-purin-9-yl)propan-2-yl (2-cyanoethyl) diisopropylphosphoramidite (9)

Compound 8 (5.2 mmol) is dissolved in THF (10 mL) under a dry nitrogen environment. This is followed by the addition of DIPEA (22 mmol) and the dropwise addition of β-cyanoethyldiisopropyl phosphorochlorodite (6.2 mmol). The reaction is allowed to proceed for 6 h. Upon completion, the reaction mixture is filtered and evaporated to dryness to give a white foam. This is purified by column chromatography to give 9.

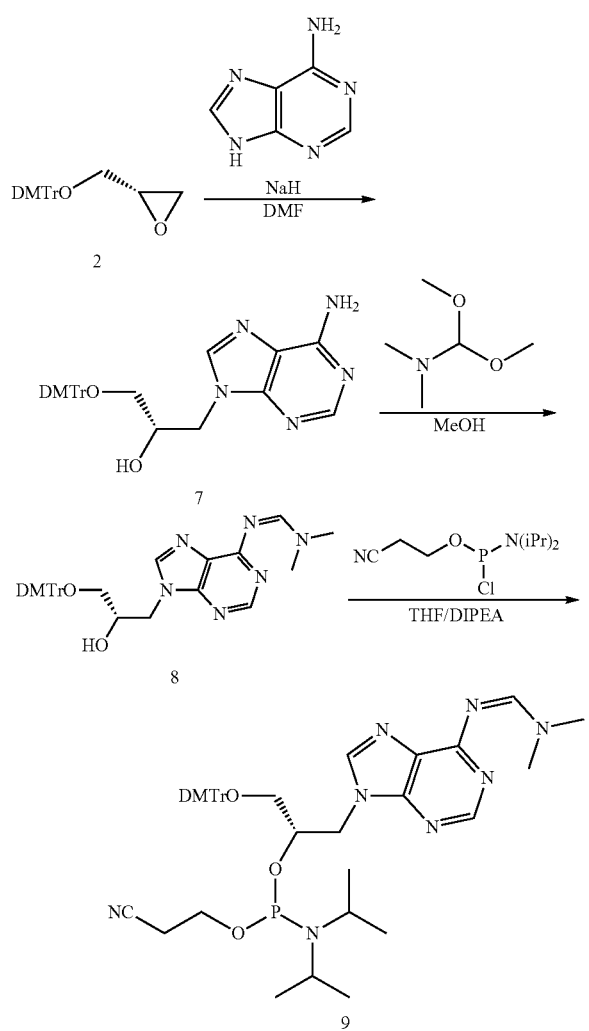

Synthesis of adenine GNA phosphoramidite (according to Meggers, *J. Org. Chem*, 2009)

(S)-1-(6-amino-9H-purin-9-yl)-3-(bis(4-methoxyphenyl)(phenyl)methoxy)propan-2-ol (7)

Adenosine (14 mmol) is dried overnight in a 100 mL round bottom flask and then suspended in DMF (22 mL)

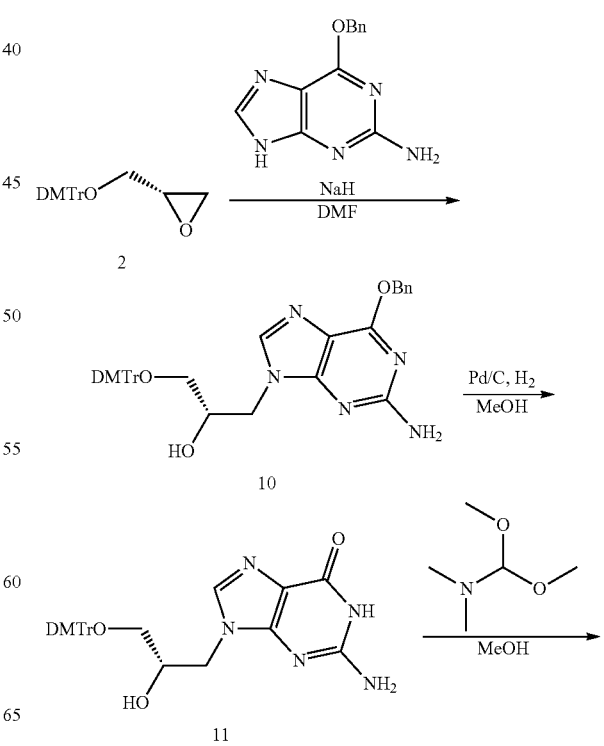

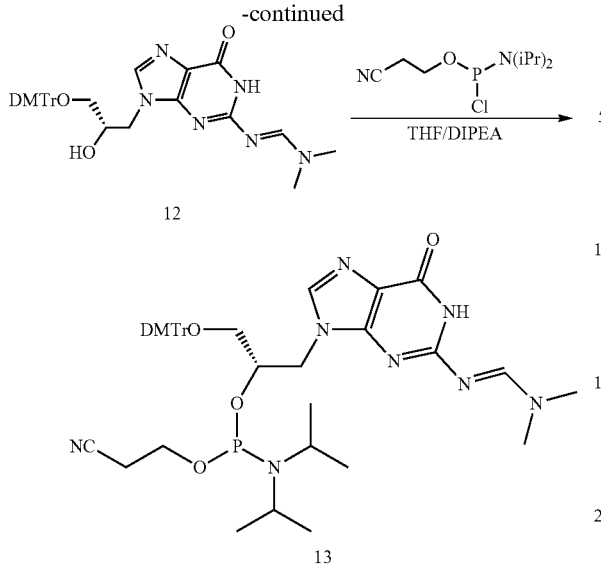

Synthesis of guanine GNA phosphoramidite (according to Meggers, *J. Org. Chem*, 2009)

(S)-1-(2-amino-6-(benzyloxy)-9H-purin-9-yl)-3-(bis(4-methoxyphenyl)(phenyl)methoxy)propan-2-ol (10)

O-6-benzyl guanosine (14 mmol) is dried overnight in a 100 mL round bottom flask and then suspended in DMF (22 mL) under a nitrogen atmosphere. This is followed by the addition of NaH (3.3 mmol). The reaction mixture is allowed to stir for 2 h at room temperature. This is followed by the addition of 2 in DMF (22 mL). The reaction mixture is then heated to 110° C. and kept overnight. Upon completion of the reaction, it is evaporated to dryness and coevaporated with toluene and ethyl acetate. It is then purified by column chromatography to give 10.

(S)-2-amino-9-(3-(bis(4-methoxyphenyl)(phenyl)methoxy)-2-hydroxypropyl)-1H-purin-6(9H)-one (11)

Compound 10 (14 mmol) is dissolved in methanol (50 mL). This is followed by the addition of 20% by weight 10% Pd/C. The reaction mixture is then purged with nitrogen and fitted with a balloon of hydrogen. The reaction is then stirred 3 h at room temperature at which point it is filtered over a pad of celite. The celite is washed with methanol and the pooled organic fractions are evaporated to dryness to give 11. This material is used without further purification.

(S,E)-N'-(9-(3-(bis(4-methoxyphenyl)(phenyl)methoxy)-2-hydroxypropyl)-6-oxo-6,9-dihydro-1H-purin-2-yl)-N,N-dimethylformimidamide (12)

Compound 11 (5.2 mmol) is dissolved in methanol (40 mL). This is followed by the addition of dimethyl formamidine dimethyl acetal (20 mmol) and stirring for 16 h. The reaction mixture is then evaporated to dryness and purified by column chromatography to give 12.

(S)-1-(bis(4-methoxyphenyl)(phenyl)methoxy)-3-(2-((E)-((dimethylamino)methylene)amino)-6-oxo-1H-purin-9(6H)-yl)propan-2-yl (2-cyanoethyl) diisopropylphosphoramidite (13)

Compound 12 (5.2 mmol) is dissolved in THF (10 mL) under a dry nitrogen environment. This is followed by the addition of DIPEA (22 mmol) and the dropwise addition of β-cyanoethyldiisopropyl phosphorochlorodite (6.2 mmol). The reaction is allowed to proceed for 6 h. Upon completion, the reaction mixture is filtered and evaporated to dryness to give a white foam. This is purified by column chromatography to give 13.

Example 2

Synthesis of GYNA Phosphoramidates (e.g. Guanosine GYNA Phosphoramidite)

Scheme 5.

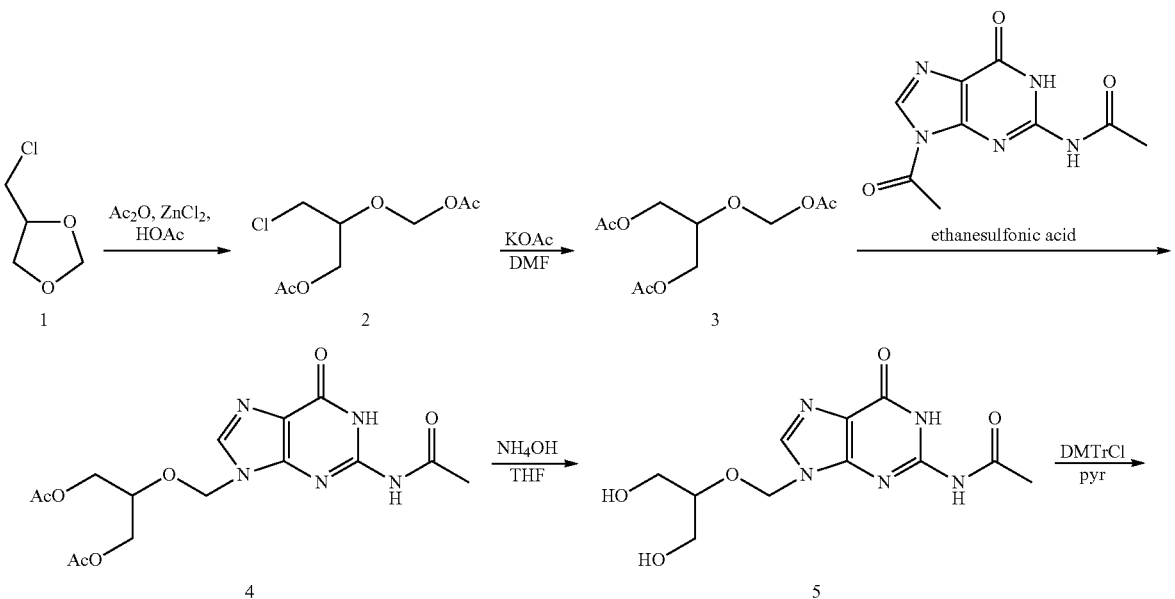

-continued

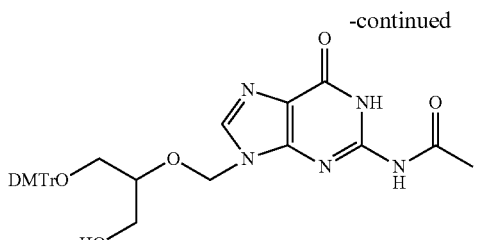
6

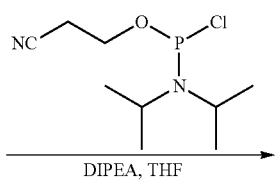

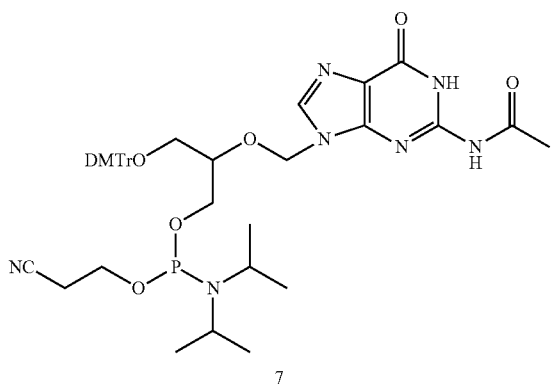
7

Synthesis of guanine GYNA phosphoramidite (according to Tolman, *PNAS*, 1983)

1-Chloro-2-acetoxymethoxy-3-acetoxypropane (2)

A mixture of 4-chloromethyl-1,3-dioxolane 1 (0.2 mol), acetic anhydride (0.63 mol), glacial acetic acid (0.12 mol), and ZnCl$_2$ (0.015 mol) is stirred under a nitrogen atmosphere in. The mixture is stirred for 2 hr at room temperature. The solvent is then removed under reduced pressure, and the oil is mixed with diethyl ether (100 ml), washed with saturated NaHCO$_3$ solution and water, dried (MgSO$_4$), filtered, and concentrated in vacuo. To give a mix of isomers. This material is then purified by column chromatography to give 2.

1,3-Diacetoxy-2-acetoxymethoxy propane (3)

Anhydrous potassium acetate (0.356 mol) is added to (0.156 mol) of 2 in DMF (250 mL), which is stirred with a mechanical stirrer. The suspension is heated to 150° C. and maintained there until the reaction is determined complete. The reaction mixture is then cooled to room temperature and diluted with ethyl acetate and washed with sat. aq. Sodium bicarbonate. The organic layer is dried over sodium sulfate, filtered and evaporated in vacuo. To give 3. It can be used in the next step without purification.

9-{[2-Acetoxy-1-(acetoxymethyl)ethoxy]methyl}-2-acetamidopurin-6-one (4)

A short-path distillation apparatus with a 500-ml distilling flask is charged with diacetylguanine (0.18 mol), III (49 g, 0.198 mol), and ethanesulfonic acid (0.0198 mol). The mixture is then heated at 165-170° C. under reduced pressure. After 0.5 hr, it is allowed to cool and is dissolved in dichloromethane (1 L) and filtered, and evaporated in vacuo. The residue is then purified by column chromatography to give 4.

N-(9-(((1,3-dihydroxypropan-2-yl)oxy) methyl)-6-oxo-6,9-dihydro-1H-purin-2-yl)acetamide (5)

Compound 4 (0.10 mol) is dissolved in methanol (200 mL). This solution is then cooled to 0° C. followed by the addition of ammonium hydroxide (20 mL). The reaction mixture is stirred for 30 min and then evaporated in vacuo. The resulting residue is then precipitated from ether to give 5.

N-(9-(((1-(bis(4-methoxyphenyl)(phenyl)methoxy)-3-hydroxypropan-2-yl)oxy)methyl)-6-oxo-6,9-dihydro-1H-purin-2-yl)acetamide (6)

Compound 5 (0.10 mol) is dissolved in pyridine (200 mL) under nitrogen atmosphere. This is followed by the addition of DMTrCl (0.105 mol). The reaction mixture is then stirred overnight. The solvent is then removed in vacuo and the residue is redissolved in ethyl acetate. It is washed with sat. aq. Bicarbonate, brine, and water. The organic layer is dried over magnesium sulfate, filtered, and evaporated in vacuo. The residue is then purified by column chromatography to give 6.

2-((2-acetamido-6-oxo-1H-purin-9(6H)-yl)methoxy)-3-(bis(4-methoxyphenyl)(phenyl)methoxy)propyl (2-cyanoethyl) diisopropylphosphoramidite (7)

Compound 6 (0.5 mol) is dissolved in THF (50 mL) under a dry nitrogen environment. This is followed by the addition of DIPEA (2 mol) and the dropwise addition of O-cyanoethyldiisopropyl phosphorochlorodite (0.505). The reaction is allowed to proceed until completion. Upon completion, it is quenched with 10 mL of 5% aq. Sodium bicarbonate and diluted with 250 mL of ethyl acetate. The organic layer is washed with 5% aq. Bicarbonate, brine, and water is filtered and evaporated to dryness. It is then purified by column chromatography to give 7.

Example 3: In Vitro RNAi Activity of Acyclic and Abasic Nucleoside Comprising Single-Stranded and Double-Stranded RNAi Agents

TABLE 1 ssRNA & siRNA activity at 1 nM in HeLa

| AS ID | SEQ ID NO: | Sequence(5'-3') | % KD | siRNA ID | % KD | Position |
|---|---|---|---|---|---|---|
| 447581 | 3 | P$_o$-T$_s$UfsgUfscUfscUfsgGfsuCfscUfsusAfscsUfsus(Aeos)(Aeo) | 87 | | | |
| A-53286 | 44 | P(Teos)UfsgUfscUfscUfsgGfsuCfscUfsusAfscsUfsus(Aeos)(Aeo) | 72 | AD-26396 | 87 | |
| A-63607 | 45 | PusUfsgUfscUfscUfsgGfsuCfscUfsusAfscsUfsus(Tgns)(Tgn) | 77 | AD-29348 | 89 | |
| A-63608 | 46 | PusUfsgUfscUfscUfsgGfsuCfscUfsusAfscsUfsus(Tgn)(Tgn) | 73 | AD-29349 | 87 | |
| A-63605 | 47 | P(Tgns)UfsgUfscUfscUfsgGfsuCfscUfsusAfscsUfsus(Aeos)(Aeo) | 54 | AD-29346 | 79 | N1 |
| A-63606 | 48 | P(Tgn)UfsgUfscUfscUfsgGfsuCfscUfsusAfscsUfsus(Aeos)(Aeo) | 63 | AD-29347 | 81 | N1 |
| A-63609 | 49 | Pus(Tgns)gUfscUfscUfsgGfsuCfscUfsusAfscsUfsus(Aeos)(Aeo) | 61 | AD-29350 | 43 | N2 |
| A-63610 | 50 | PusUfsg(Tgns)cUfscUfsgGfsuCfscUfsusAfscsUfsus(Aeos)(Aeo) | 72 | AD-29351 | 91 | N4 |
| A-63611 | 51 | PusUfsgUfsc(Tgns)cUfsgGfsuCfscUfsusAfscsUfsus(Aeos)(Aeo) | | | | |
| A-63612 | 52 | PusUfsgUfscUfsc(Tgns)gGfsuCfscUfsusAfscsUfsus(Aeos)(Aeo) | | | | |

TABLE 2 ssRNA & siRNA activity at 1 nM in HeLa

| AS ID | SEQ ID NO: | Sequence(5'-3') | % KD | siRNA ID | % KD | Position |
|---|---|---|---|---|---|---|
| 447581 | 3 | P$_o$-T$_s$UfsgUfscUfscUfsgGfsuCfscUfsusAfscsUfsus(Aeos)(Aeo) | 87 | | | |
| A-53286 | 44 | P(Teos)UfsgUfscUfscUfsgGfsuCfscUfsusAfscsUfsus(Aeos)(Aeo) | 72 | AD-26396 | 87 | |
| A-63830 | 53 | PusUfsgUfscUfscUfsgGfsuCfscUfsusAfscsUfsusY33sY33 | 49 | AD-29360 | 88 | |
| A-63831 | 53 | PusUfsgUfscUfscUfsgGfsuCfscUfsusAfscsUfsusY33Y33 | 54 | AD-29361 | 85 | |
| A-63828 | 54 | PY33sUfsgUfscUfscUfsgGfsuCfscUfsusAfscsUfsus(Aeos)(Aeo) | 60 | AD-29354 | 90 | N1 |
| A-63829 | 54 | PY33UfsgUfscUfscUfsgGfsuCfscUfsusAfscsUfsus(Aeos)(Aeo) | 75 | AD-29355 | 93 | N1 |
| A-63832 | 55 | PusY33sgUfscUfscUfsgGfsuCfscUfsusAfscsUfsus(Aeos)(Aeo) | 64 | AD-29356 | 91 | N2 |
| A-63833 | 56 | PusUfsgY33scUfscUfsgGfsuCfscUfsusAfscsUfsus(Aeos)(Aeo) | 77 | AD-29357 | 94 | N4 |
| A-63834 | 57 | PusUfsgUfscY33scUfsgGfsuCfscUfsusAfscsUfsus(Aeos)(Aeo) | 86 | AD-29358 | 96 | N6 |
| A-63835 | 58 | PusUfsgUfscUfscY33sgGfsuCfscUfsusAfscsUfsus(Aeos)(Aeo) | 67 | AD-29359 | 93 | N8 |

% KD: % KD refers to % knockdown.

Figure 3:
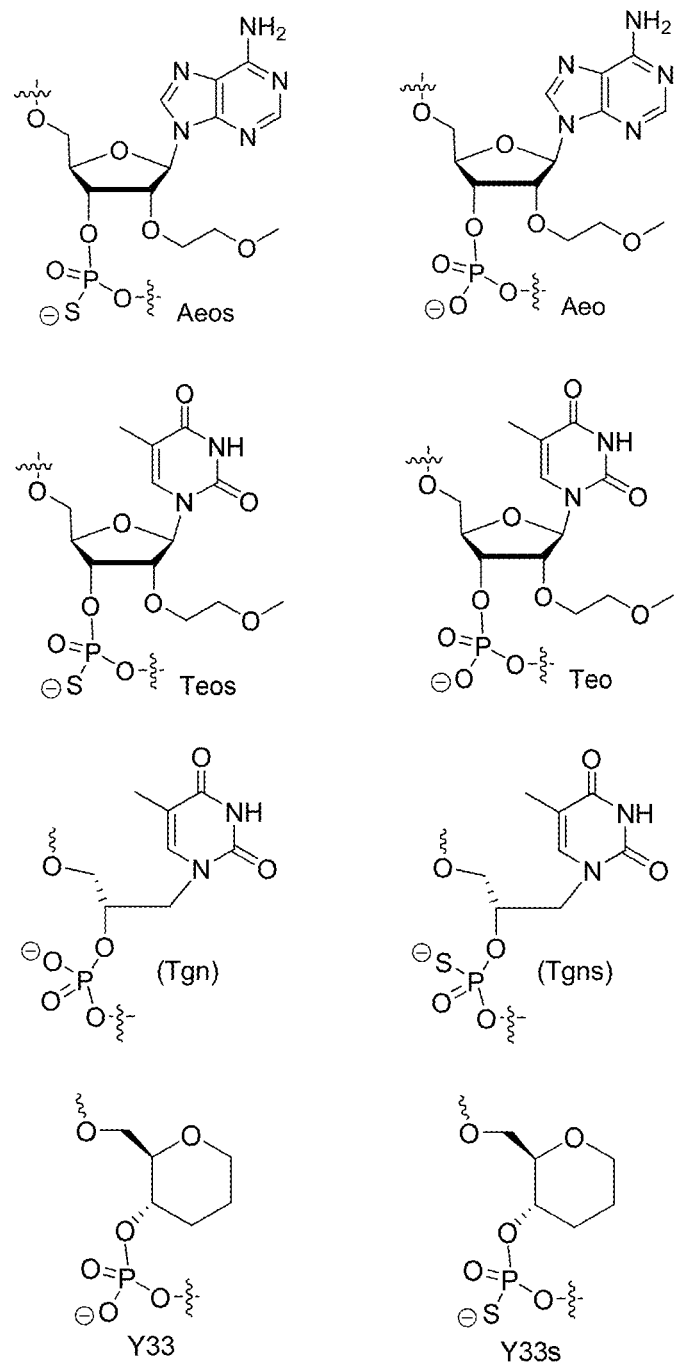
FIG. 3 shows schematic representations of some the monomers used for oligonucleotide synthesis.

In table 1 and 2, P is phosphate at 5'-end, lowercase letters a, c, g and u represents 2'-OMe A, C, G and U respectively, 's' stands for phosphorothioate, Af, Cf, Uf and Gf represents 2'-deoxy-2'-fluoro A, C, U and G respectively. T is ribo-T or 5-Methyl-riboU. Structures for Aeo, Aeos, Teo, Teso, Tgn, Tgns, Y33 and Y33s are shown in FIG. 3.

EQUIVALENTS

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

We claim:

1. An oligonucleotide comprising at least one monomer of formula (V):

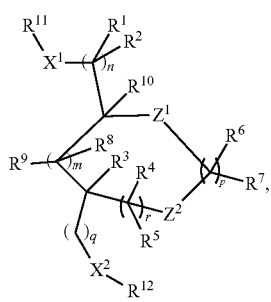

wherein the oligonucleotide is a double-stranded siRNA, a single-stranded siRNA, or a hairpin oligonucleotide, and wherein:

$X^1$ and $X^2$ are independently for each occurrence absent, O, S, or NR';

each of $R^1$, $R^2$, $R^3$, $R^4$, $R^5$, $R^6$, $R^7$, $R^8$, $R^9$ and $R^{10}$ is independently for each occurrence H, halo, $OR^{13}$, N(R')(R''), straight chain or branched chain alkyl, alkenyl, alkynyl, aryl, ω-amino alkyl, ω-hydroxy alkenyl, or ω-hydroxy alkynyl, each of which can be optionally substituted;

$R^{11}$ and $R^{12}$ are independently for each occurrence H,

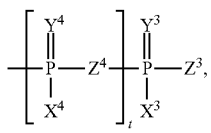

nucleoside, oligonucleotide,

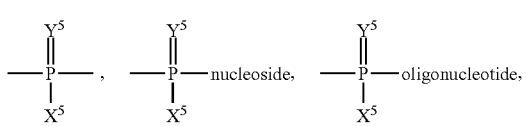

—O-oligonucleotide, —S-oligonucleotide, —S—S-oligonucleotide, —N(R')—C($Z^6$)-oligonucleotide, —C($Z^6$)—N(R')-oligonucleotide, —N(R')—C($Z^6$)$Z^6$-oligonucleotide, —$Z^6$C($Z^6$)—N(R')-oligonucleotide, N(R')C($Z^6$)N(R')-oligonucleotide

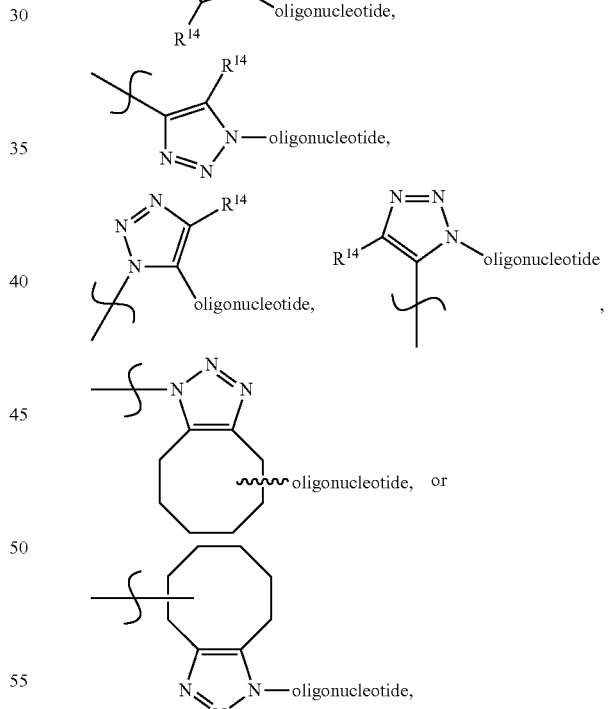

provided that at least one of $R^{11}$ and $R^{12}$ contains an oligonucleotide;

$R^{13}$ is independently for each occurrence H, straight chain or branched chain alkyl, alkenyl, alkynyl, aryl, aralkyl, ω-amino alkyl, or ω-hydroxy alkenyl, each of which can be optionally substituted;

$R^{14}$ is independently for each occurrence H, halo, $OR^{12}$, N(R')(R''), alkyl, alkenyl, alkynyl, aryl, heteroaryl, heterocyclyl, ω-amino alkyl, ω-hydroxy alkyl, or ω-hydroxy alkenyl, each of which can be optionally substituted;

$X^3$, $X^4$, $X^5$, and $Z^5$ are each independently for each occurrence H, O⁻, OM, $OR^{13}$, S⁻, $SR^{13}$, SM, N(R')(R"), $B(R^{13})_3$, $BH_3^-$, or Se;

$Z^1$ and $Z^2$ are each independently O, S, N(R'), $C(R^9)(R^{10})$, $C(R^9)(OR^{13})$, C(O), or C(S);

$Y^3$, $Y^4$, $Y^5$, and $Z^6$ are each independently for each occurrence O or S;

$Z^4$ is independently for each occurrence O, S, $CH_2$, or NR';

each of R' and R" is independently for each occurrence H, alkyl, alkenyl, alkynyl, aryl, ω-amino alkyl, ω-hydroxy alkyl, ω-hydroxy alkenyl, or o-hydroxy alkynyl, each of which can be optionally substituted;

each of m, n, p, q, and r is independently for each occurrence 0-1, provided that m+p+r=2;

t is 0-2; and

M is an organic or inorganic cation, wherein, in each occurrence, the optionally substituted group is independently selected from the group consisting of halo, hydroxy, oxo, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido.

2. The oligonucleotide of claim 1, wherein the monomer is of formula (V'):

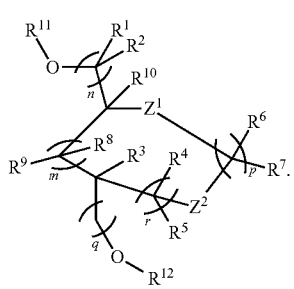

3. The oligonucleotide of claim 1, wherein at least one of $R^{11}$ or $R^{12}$ is

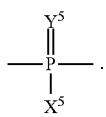

4. An oligonucleotide comprising at least one monomer of formula (VIII):

VIII

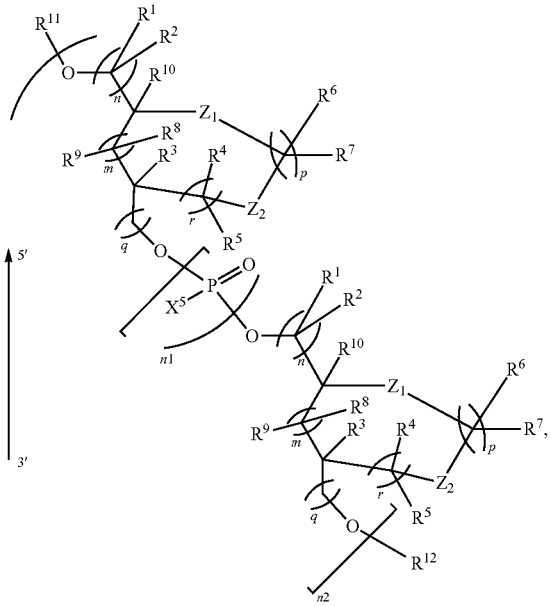

wherein the oligonucleotide is a double-stranded siRNA, a single-stranded siRNA, or a hairpin oligonucleotide, and wherein:

each of $R^1$, $R^2$, $R^3$, $R^4$, $R^5$, $R^6$, $R^7$, $R^8$, $R^9$ and $R^{10}$ is independently for each occurrence H, halo, $OR^{13}$, N(R')(R"), straight chain or branched chain alkyl, alkenyl, alkynyl, aryl, ω-amino alkyl, ω-hydroxy alkenyl, or ω-hydroxy alkynyl, each of which can be optionally substituted;

$R^{11}$ and $R^{12}$ are independently for each occurrence H,

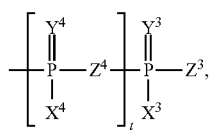

nucleoside, oligonucleotide

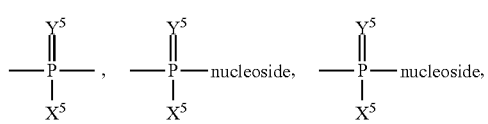

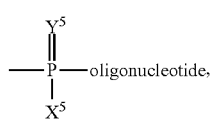

—O-oligonucleotide, —S-oligonucleotide, —S—S-oligonucleotide, —N(R')—C(Z$^6$)-oligonucleotide, —C(Z$^6$)—N(R')-oligonucleotide, —N(R')—C(Z$^6$)Z$^6$-oligonucleotide, —Z$^6$C(Z$^6$)—N(R')-oligonucleotide, N(R')C(Z$^6$)N(R')-oligonucleotide,

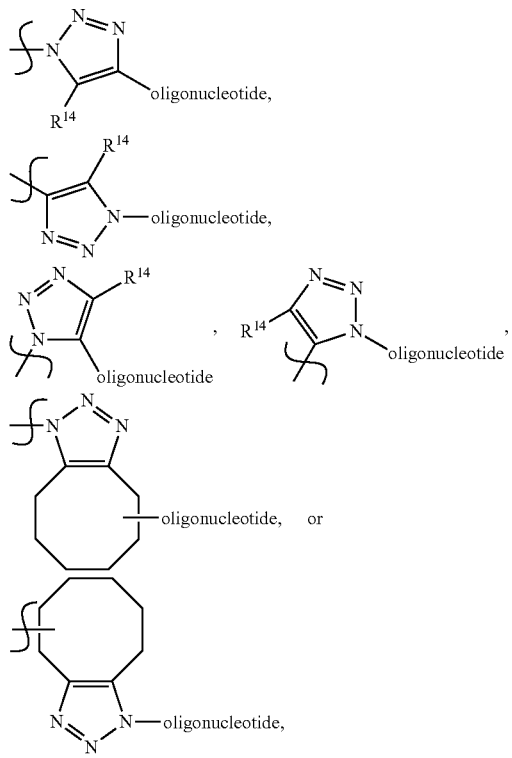

provided that at least one of R$^{11}$ and R$^{12}$ contains an oligonucleotide;

R$^{13}$ is independently for each occurrence H, straight chain or branched chain alkyl, alkenyl, alkynyl, aryl, aralkyl, ω-amino alkyl, or ω-hydroxy alkenyl, each of which can be optionally substituted;

R$^{14}$ is independently for each occurrence H, halo, OR$^2$, N(R')(R"), alkyl, alkenyl, alkynyl, aryl, heteroaryl, heterocyclyl, ω-amino alkyl, ω-hydroxy alkyl, or ω-hydroxy alkenyl, each of which can be optionally substituted;

X$^3$, X$^4$, X$^5$, and Z$^3$ are each independently for each occurrence H, O$^-$, OM, OR$^{13}$, S$^-$, SR$^{13}$, SM, N(R')(R"), B(R$^{13}$)$_3$, BH$_3^-$, or Se;

Z$^1$ and Z$^2$ are each independently O, S, N(R'), C(R$^9$)(R$^{10}$), C(R$^9$)(OR$^{13}$), C(O), or C(S);

Y$^3$, Y$^4$, Y$^5$, and Z$^6$ are each independently for each occurrence O or S;

Z$^4$ is independently for each occurrence O, S, CH$_2$, or NR';

each of R' and R" is independently for each occurrence H, alkyl, alkenyl, alkynyl, aryl, ω-amino alkyl, ω-hydroxy alkyl, ω-hydroxy alkenyl, or ω-hydroxy alkynyl, each of which can be optionally substituted;

each of m, n, p, q, and r is independently for each occurrence 0-1, provided that m+p+r=2;

n1 and n2 are each independently 0-49, provided that at least one of n1 and n2 is present, and when one of n1 and n2 is present, the other one is absent;

t is 0-2; and

M is an organic or inorganic cation, wherein, in each occurrence, the optionally substituted group is independently selected from the group consisting of halo, hydroxy, oxo, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido.

5. The oligonucleotide of claim 4, wherein n1 or n2 is 1-20.

6. The oligonucleotide of claim 1, wherein the monomer is at the 5'-end terminal position of the oligonucleotide.

7. The oligonucleotide of claim 1, wherein the monomer is at the 3'-end terminal position of the oligonucleotide.

8. The oligonucleotide of claim 1, wherein the monomer is at an internal position of the oligonucleotide.

9. The oligonucleotide of claim 1, wherein the monomer is at both the 5'- and 3'-end terminal position of the oligonucleotide.

10. The oligonucleotide of claim 1, wherein the monomer is present at the 5'-end terminal position and at least one internal position of the oligonucleotide.

11. The oligonucleotide of claim 1, wherein the monomer is present at the 3'-end terminal position and at least one internal position of the oligonucleotide.

12. The oligonucleotide of claim 1, wherein the monomer is present at the 5'-end and the 3'-end terminal position and at least one internal position of the oligonucleotide.

13. The oligonucleotide of claim 1, wherein the oligonucleotide comprises at least one non-phosphodiester internucleoside linkage.

14. The oligonucleotide of claim 1, wherein the oligonucleotide comprises at least one non-phosphodiester internucleoside linkage selected from the group consisting of phosphorothioate, phosphorodithioate, H-phosphonate, alkyl-phosphonate, phosphoramidate internucleoside linkages, and any combinations thereof.

15. The oligonucleotide of claim 1, wherein the oligonucleotide comprises at least one nucleobase modification.

16. The oligonucleotide of claim 1, wherein the oligonucleotide comprises at least one sugar modification.

17. The oligonucleotide of claim 1, wherein the oligonucleotide comprises at least one ligand conjugate.

18. The oligonucleotide of claim 1, wherein the oligonucleotide is a double-stranded siRNA comprising a first strand and a second strand.

19. The oligonucleotide of claim 1, wherein the oligonucleotide is a double-stranded siRNA comprising a first strand and a second strand, and wherein both strands of the double-stranded siRNA independently comprise at least one monomer of formula (V).

20. The oligonucleotide of claim 4, wherein the oligonucleotide is a double-stranded siRNA comprising a first strand and a second strand, and wherein both strands of the double-stranded siRNA independently comprise at least one monomer of formula (VIII).

21. The oligonucleotide of claim 18, wherein the first strand is a sense strand.

22. The oligonucleotide of claim 18, wherein the second strand is an antisense strand.

23. The oligonucleotide of claim 1, wherein the oligonucleotide is a single-stranded siRNA.

24. The oligonucleotide of claim 1, wherein the oligonucleotide is a hairpin oligonucleotide.

25. The oligonucleotide of claim 1, wherein the oligonucleotide comprises:
- 1-20 first-type regions, each first-type region independently comprising 1-20 contiguous nucleosides wherein each nucleoside of each first-type region comprises a first-type modification;
- 0-20 second-type regions, each second-type region independently comprising 1-20 contiguous nucleosides wherein each nucleoside of each second-type region comprises a second-type modification; and
- 0-20 third-type regions, each third-type region independently comprising 1-20 contiguous nucleosides wherein each nucleoside of each third-type region comprises a third-type modification,
- wherein the first-type modification, the second-type modification, and the third-type modification are each independently selected from the group consisting of 2'-F, 2'-OCH$_3$, 2'-O(CH$_2$)$_2$OCH$_3$, BNA, F-HNA, 2'-H and 2'-OH.

* * * * *